US011311726B2

(12) United States Patent
Vansickle et al.

(10) Patent No.: US 11,311,726 B2
(45) Date of Patent: Apr. 26, 2022

(54) NEUROMODULATION SYSTEM AND METHOD FOR TRANSITIONING BETWEEN PROGRAMMING MODES

(71) Applicant: Boston Scientific Neuromodulation Corporation, Valencia, CA (US)

(72) Inventors: Dennis Allen Vansickle, Lancaster, CA (US); Dongchul Lee, Agua Dulce, CA (US); Sridhar Kothandaraman, Valencia, CA (US); Que T. Doan, West Hills, CA (US); Changfang Zhu, Valencia, CA (US); Jordi Parramon, Valencia, CA (US); Justin Holley, Vejle (DK); Bradley L. Hershey, Carrollton, TX (US); Christopher E. Gillespie, Stevenson Ranch, CA (US); Rafael Carbunaru, Valley Village, CA (US); Nazim Wahab, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 414 days.

(21) Appl. No.: 16/275,892

(22) Filed: Feb. 14, 2019

(65) Prior Publication Data

US 2019/0184168 A1 Jun. 20, 2019

Related U.S. Application Data

(63) Continuation of application No. 14/214,752, filed on Mar. 15, 2014, now abandoned.
(Continued)

(51) Int. Cl.
*A61N 1/36* (2006.01)
*A61N 1/372* (2006.01)

(52) U.S. Cl.
CPC ..... *A61N 1/36071* (2013.01); *A61N 1/36185* (2013.01); *A61N 1/37247* (2013.01)

(58) Field of Classification Search
CPC ............ A61N 1/36071; A61N 1/36185; A61N 1/37247
See application file for complete search history.

(56) References Cited

U.S. PATENT DOCUMENTS 5,948,007 A 9/1999 Starkebaum et al.
6,181,969 B1 1/2001 Gord
(Continued)

FOREIGN PATENT DOCUMENTS

AU 2014233252 B2 7/2017
AU 2017204544 B2 1/2019
(Continued)

OTHER PUBLICATIONS

"U.S. Appl. No. 14/214,752, Advisory Action dated Feb. 16, 2017", 10 pgs.
(Continued)

*Primary Examiner* — William J Levicky
(74) *Attorney, Agent, or Firm* — Schwegman Lundberg & Woessner, P.A.

(57) ABSTRACT

An external control device, neuromodulation system, and method of providing therapy to a patient using an implantable neuromodulator implanted within the patient. Electrical modulation energy is delivered from the neuromodulator to the patient in accordance with the pre-existing modulation program when in one of the super-threshold delivery mode and the sub-threshold delivery mode. Operation of the neuromodulator is switched to the other of the super-threshold delivery mode and the sub-threshold delivery mode. A new modulation program may be derived from a pre-existing modulation program, and the neuromodulator may
(Continued)

deliver the electrical modulation energy to the patient in accordance with the pre-existing modulation program during the other of the super-threshold delivery mode and the sub-threshold delivery mode.

18 Claims, 17 Drawing Sheets

Related U.S. Application Data

(60) Provisional application No. 61/801,917, filed on Mar. 15, 2013.

(56) References Cited

U.S. PATENT DOCUMENTS

| | | | |
|---|---|---|---|
| 6,516,227 B1 | 2/2003 | Meadows et al. |
| 6,609,029 B1 | 8/2003 | Mann et al. |
| 6,609,032 B1 | 8/2003 | Woods et al. |
| 6,675,046 B2 | 1/2004 | Holsheimer |
| 6,741,892 B1 | 5/2004 | Meadows et al. |
| 6,895,280 B2 | 5/2005 | Meadows et al. |
| 6,993,384 B2 | 1/2006 | Bradley et al. |
| 7,244,150 B1 | 7/2007 | Brase et al. |
| 7,317,948 B1 | 1/2008 | King et al. |
| 7,321,797 B2 | 1/2008 | Blamey et al. |
| 7,333,857 B2 | 2/2008 | Campbell |
| 7,359,751 B1 | 4/2008 | Erickson et al. |
| 7,539,538 B2 | 5/2009 | Parramon et al. |
| 7,650,184 B2 | 1/2010 | Walter |
| 7,672,734 B2 | 3/2010 | Anderson et al. |
| 7,761,165 B1 | 7/2010 | He et al. |
| 7,761,166 B2 | 7/2010 | Gerber et al. |
| 7,783,353 B2 | 8/2010 | Libbus et al. |
| 7,949,395 B2 | 5/2011 | Kuzma |
| 7,974,706 B2 | 7/2011 | Moffitt et al. |
| 7,979,133 B2 | 7/2011 | Feler et al. |
| 8,019,439 B2 | 9/2011 | Kuzma et al. |
| 8,170,675 B2 | 5/2012 | Alataris et al. |
| 8,175,710 B2 | 5/2012 | He |
| 8,209,021 B2 | 6/2012 | Alataris et al. |
| 8,224,436 B2 | 7/2012 | Libbus et al. |
| 8,224,450 B2 | 7/2012 | Brase |
| 8,224,453 B2 | 7/2012 | De Ridder |
| 8,255,057 B2 | 8/2012 | Fang et al. |
| 8,285,389 B2 | 10/2012 | Libbus et al. |
| 8,355,792 B2 | 1/2013 | Alataris et al. |
| 8,355,797 B2 | 1/2013 | Caparso et al. |
| 8,359,102 B2 | 1/2013 | Alataris et al. |
| 8,359,103 B2 | 1/2013 | Alataris et al. |
| 8,364,278 B2 | 1/2013 | Pianca et al. |
| 8,380,318 B2 | 2/2013 | Kishawi et al. |
| 8,396,559 B2 | 3/2013 | Alataris et al. |
| 8,401,640 B2 | 3/2013 | Zhao et al. |
| 8,406,876 B2 | 3/2013 | McCabe et al. |
| 8,412,345 B2 | 4/2013 | Moffitt |
| 8,423,147 B2 | 4/2013 | Alataris et al. |
| 8,455,716 B2 | 6/2013 | Huang et al. |
| 8,473,061 B2 | 6/2013 | Moffitt et al. |
| 8,504,147 B2 | 8/2013 | Deem et al. |
| 8,527,042 B2 | 9/2013 | Libbus et al. |
| 8,571,665 B2 | 10/2013 | Moffitt et al. |
| 8,615,300 B2 | 12/2013 | Feler et al. |
| 8,649,874 B2 | 2/2014 | Alataris et al. |
| 8,660,653 B2 | 2/2014 | Kothandaraman |
| 8,670,831 B2 | 3/2014 | Wacnik et al. |
| 8,676,329 B2 | 3/2014 | Wacnik et al. |
| 8,676,331 B2 | 3/2014 | Parker |
| 8,700,178 B2 | 4/2014 | Anderson |
| 8,731,675 B2 | 5/2014 | Ranu et al. |
| 8,751,009 B2 | 6/2014 | Wacnik |
| 8,792,993 B2 | 7/2014 | Pianca et al. |
| 8,874,211 B2 | 10/2014 | Libbus et al. |
| 8,880,170 B2 | 11/2014 | Bradley et al. |
| 8,909,350 B2 | 12/2014 | Lee |
| 8,923,981 B2 | 12/2014 | Grill, Jr. et al. |
| 9,002,459 B2 | 4/2015 | Lee et al. |
| 9,095,712 B2 | 8/2015 | Lee |
| 9,186,522 B2 | 11/2015 | Ternes |
| 9,220,900 B2 | 12/2015 | Libbus et al. |
| 9,265,948 B2 | 2/2016 | Libbus et al. |
| 9,630,012 B2 | 4/2017 | Carroll |
| 9,694,183 B2 | 7/2017 | Grandhe et al. |
| 9,744,365 B2 | 8/2017 | Davis et al. |
| 9,950,173 B2 | 4/2018 | Doan |
| 9,993,646 B2 | 6/2018 | Parramon et al. |
| 10,029,102 B2 | 7/2018 | Doan et al. |
| 10,039,930 B2 | 8/2018 | Vallejo et al. |
| 10,226,626 B2 | 3/2019 | Alataris et al. |
| 10,780,274 B2 | 9/2020 | Parramon et al. |
| 2003/0120323 A1* | 6/2003 | Meadows .......... A61N 1/36071 607/46 |
| 2003/0139781 A1 | 7/2003 | Bradley et al. |
| 2004/0215286 A1 | 10/2004 | Stypulkowski |
| 2005/0267546 A1 | 12/2005 | Parramon et al. |
| 2006/0200205 A1 | 9/2006 | Haller |
| 2006/0259099 A1 | 11/2006 | Goetz et al. |
| 2007/0100377 A1 | 5/2007 | Armstrong et al. |
| 2007/0150036 A1 | 6/2007 | Anderson |
| 2007/0168004 A1 | 7/2007 | Walter |
| 2007/0168007 A1 | 7/2007 | Kuzma et al. |
| 2007/0203521 A1 | 8/2007 | Dobak et al. |
| 2008/0021504 A1 | 1/2008 | McCabe et al. |
| 2008/0188909 A1 | 8/2008 | Bradley |
| 2008/0294211 A1 | 11/2008 | Moffitt |
| 2009/0204173 A1 | 8/2009 | Fang et al. |
| 2009/0281596 A1 | 11/2009 | King et al. |
| 2010/0010566 A1 | 1/2010 | Thacker et al. |
| 2010/0023070 A1 | 1/2010 | Moffitt et al. |
| 2010/0057162 A1* | 3/2010 | Moffitt .............. A61N 1/36071 607/46 |
| 2010/0121408 A1 | 5/2010 | Imran et al. |
| 2010/0121409 A1 | 5/2010 | Kothandaraman et al. |
| 2010/0191307 A1 | 7/2010 | Fang et al. |
| 2010/0198300 A1 | 8/2010 | Smith |
| 2010/0249875 A1 | 9/2010 | Kishawi et al. |
| 2010/0268298 A1 | 10/2010 | Moffitt et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274317 A1 | 10/2010 | Parker et al. |
| 2010/0274318 A1 | 10/2010 | Walker et al. |
| 2010/0274326 A1 | 10/2010 | Chitre et al. |
| 2010/0280440 A1 | 11/2010 | Skelton et al. |
| 2011/0005069 A1 | 1/2011 | Pianca |
| 2011/0009923 A1 | 1/2011 | Lee |
| 2011/0054568 A1 | 3/2011 | Lane et al. |
| 2011/0071593 A1 | 3/2011 | Parker et al. |
| 2011/0078900 A1 | 4/2011 | Pianca et al. |
| 2011/0106215 A1 | 5/2011 | Moffitt |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0137370 A1 | 6/2011 | Gross et al. |
| 2011/0238129 A1 | 9/2011 | Moffitt |
| 2011/0264156 A1 | 10/2011 | Mukherjee et al. |
| 2012/0016378 A1 | 1/2012 | Pianca et al. |
| 2012/0016448 A1 | 1/2012 | Lee |
| 2012/0041511 A1 | 2/2012 | Lee |
| 2012/0041518 A1 | 2/2012 | Kim et al. |
| 2012/0046710 A1 | 2/2012 | DiGiore et al. |
| 2012/0059446 A1 | 3/2012 | Wallace et al. |
| 2012/0071949 A1 | 3/2012 | Pianca et al. |
| 2012/0083709 A1 | 4/2012 | Parker et al. |
| 2012/0089200 A1 | 4/2012 | Ranu et al. |
| 2012/0095524 A1 | 4/2012 | Nelson et al. |
| 2012/0165911 A1 | 6/2012 | Pianca |
| 2012/0197336 A1 | 8/2012 | Su |
| 2012/0197375 A1 | 8/2012 | Pianca et al. |
| 2012/0203304 A1 | 8/2012 | Alataris et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |

(56) References Cited

U.S. PATENT DOCUMENTS

| | | |
|---|---|---|
| 2012/0239109 A1 | 9/2012 | Lee |
| 2012/0253422 A1 | 10/2012 | Thacker et al. |
| 2012/0265279 A1 | 10/2012 | Zhu et al. |
| 2012/0283797 A1 | 11/2012 | De Ridder |
| 2012/0290041 A1 | 11/2012 | Kim et al. |
| 2013/0041425 A1 | 2/2013 | Fang et al. |
| 2013/0066331 A1 | 3/2013 | Chitre et al. |
| 2013/0066411 A1 | 3/2013 | Thacker et al. |
| 2013/0073007 A1 | 3/2013 | Parker et al. |
| 2013/0116752 A1 | 5/2013 | Parker et al. |
| 2013/0131760 A1 | 5/2013 | Rao et al. |
| 2013/0158628 A1 | 6/2013 | Kothandaraman |
| 2013/0158630 A1 | 6/2013 | Lee |
| 2013/0197424 A1 | 8/2013 | Bedenbaugh |
| 2013/0197602 A1 | 8/2013 | Pianca et al. |
| 2013/0268021 A1 | 10/2013 | Moffitt |
| 2013/0282078 A1* | 10/2013 | Wacnik ............ A61N 1/36071 607/59 |
| 2013/0296975 A1 | 11/2013 | Lee et al. |
| 2014/0039587 A1 | 2/2014 | Romero |
| 2014/0081349 A1 | 3/2014 | Lee et al. |
| 2014/0163660 A1 | 6/2014 | Fang et al. |
| 2014/0243926 A1 | 8/2014 | Carcieri |
| 2014/0249599 A1 | 9/2014 | Kaula et al. |
| 2014/0277267 A1 | 9/2014 | Vansickle et al. |
| 2014/0277281 A1 | 9/2014 | Grandhe |
| 2014/0343622 A1 | 11/2014 | Alataris et al. |
| 2014/0035821 A1 | 12/2014 | Howard |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0364919 A1 | 12/2014 | Doan |
| 2014/0379043 A1 | 12/2014 | Howard |
| 2015/0018898 A1 | 1/2015 | Tass |
| 2015/0018915 A1 | 1/2015 | Leven |
| 2015/0032181 A1 | 1/2015 | Baynham et al. |
| 2015/0045864 A1 | 2/2015 | Howard |
| 2015/0051681 A1 | 2/2015 | Hershey |
| 2015/0066120 A1 | 3/2015 | Govea |
| 2015/0134031 A1 | 5/2015 | Moffitt et al. |
| 2015/0151113 A1 | 6/2015 | Govea et al. |
| 2015/0209587 A1 | 7/2015 | Lee et al. |
| 2015/0328461 A1 | 11/2015 | Charlesworth et al. |
| 2016/0082256 A1 | 3/2016 | Moffitt et al. |
| 2017/0128729 A1 | 5/2017 | Netoff et al. |
| 2017/0281948 A1 | 10/2017 | Grandhe |
| 2018/0050204 A1 | 2/2018 | Parramon et al. |
| 2018/0193653 A1 | 7/2018 | Bokil |
| 2018/0221668 A1 | 8/2018 | Doan |
| 2019/0184167 A1 | 6/2019 | Vansickle et al. |
| 2020/0368529 A1 | 11/2020 | Parramon et al. |

FOREIGN PATENT DOCUMENTS

| | | |
|---|---|---|
| CN | 101516436 A | 8/2009 |
| CN | 105163802 A | 12/2015 |
| CN | 105209111 A | 12/2015 |
| CN | 105163802 B | 8/2017 |
| CN | 105209111 B | 9/2017 |
| CN | 107551402 A | 1/2018 |
| CN | 107551402 B | 6/2021 |
| CN | 113368397 A | 9/2021 |
| DE | 102012002437 A1 | 8/2013 |
| EP | 2207587 | 5/2009 |
| EP | 2968932 B1 | 10/2017 |
| EP | 2968933 B1 | 6/2019 |
| EP | 3583979 A1 | 12/2019 |
| EP | 3583979 B1 | 4/2021 |
| JP | 2011502586 A | 1/2011 |
| JP | 2016512758 A | 5/2016 |
| WO | WO-2005087314 A1 | 9/2005 |
| WO | WO-2006029257 A2 | 3/2006 |
| WO | WO-2006135791 A2 | 12/2006 |
| WO | WO-2009061813 A1 | 5/2009 |
| WO | WO-2009061813 A9 | 5/2009 |
| WO | WO-2010069317 A1 | 6/2010 |
| WO | WO-2014145222 A2 | 9/2014 |
| WO | WO-2014145222 A3 | 9/2014 |
| WO | WO-2014197564 A1 | 12/2014 |
| WO | WO-2018039117 A1 | 3/2018 |

OTHER PUBLICATIONS

"U.S. Appl. No. 14/214,752, Advisory Action dated Jun. 7, 2016", 5 pgs.

"U.S. Appl. No. 14/214,752, Appeal Brief filed Apr. 27, 2017", 48 pgs.

"U.S. Appl. No. 14/214,752, Appeal Decision dated Dec. 14, 2018", 14 pgs.

"U.S. Appl. No. 14/214,752, Applicant's Summary of Examiner Interview filed Apr. 27, 2017", 1 pg.

"U.S. Appl. No. 14/214,752, Examiner Interview Summary dated Jan. 22, 2019", 3 pgs.

"U.S. Appl. No. 14/214,752, Examiner Interview Summary dated Feb. 7, 2017", 4 pgs.

"U.S. Appl. No. 14/214,752, Final Office Action dated Apr. 1, 2016", 22 pgs.

"U.S. Appl. No. 14/214,752, Final Office Action dated Dec. 5, 2016", 36 pgs.

"U.S. Appl. No. 14/214,752, Non Final Office Action dated Sep. 1, 2016", 35 pgs.

"U.S. Appl. No. 14/214,752, Non Final Office Action dated Dec. 11, 2015", 16 pgs.

"U.S. Appl. No. 14/214,752, Preliminary Amendment filed Mar. 15, 2014", 43 pgs.

"U.S. Appl. No. 14/214,752, Response filed Feb. 6, 2017 to Final Office Action dated Dec. 5, 2016", 21 pgs.

"U.S. Appl. No. 14/214,752, Response filed Mar. 11, 2016 to Non Final Office Action dated Dec. 11, 2015", 12 pgs.

"U.S. Appl. No. 14/214,752, Response filed Jun. 1, 2016 to Final Office Action dated Apr. 1, 2016", 18 pgs.

"U.S. Appl. No. 14/214,752, Response filed Nov. 16, 2015 to Restriction Requirement dated Sep. 15, 2015", 8 pgs.

"U.S. Appl. No. 14/214,752, Restriction Requirement dated Sep. 15, 2015", 7 pgs.

"U.S. Appl. No. 14/214,752, Response filed Nov. 14, 2016 to Non Final Office Action dated Sep. 1, 2016", 19 pgs.

"Canadian Application Serial No. 2,906,940, Office Action dated Aug. 2, 2016", 5 pgs.

"Chinese Application Serial No. 201480026970.7, Office Action dated Jul. 6, 2016", With English Translation, 31 pgs.

"International Application Serial No. PCT/US2014/029945, International Preliminary Report on Patentability dated Sep. 24, 2015", 9 pgs.

"International Application Serial No. PCT/US2014/029945, International Search Report dated Nov. 13, 2014", 8 pgs.

"International Application Serial No. PCT/US2014/029945, Invitation to Pay Additional Fees and Partial Search Report dated Jun. 11, 2014", 5 pgs.

"International Application Serial No. PCT/US2014/029945, Written Opinion dated Nov. 13, 2014", 7 pgs.

"U.S. Appl. No. 14/199,845, Advisory Action dated Dec. 24, 2015", 3 pgs.

"U.S. Appl. No. 14/199,845, Examiner Interview Summary dated Feb. 1, 2017", 3 pgs.

"U.S. Appl. No. 14/199,845, Final Office Action dated Sep. 29, 2016", 12 pgs.

"U.S. Appl. No. 14/199,845, Final Office Action dated Oct. 15, 2015", 14 pgs.

"U.S. Appl. No. 14/199,845, Non Final Office Action dated Mar. 12, 2015", 11 pgs.

"U.S. Appl. No. 14/199,845, Non Final Office Action dated Mar. 23, 2016", 12 pgs.

"U.S. Appl. No. 14/199,845, Notice of Allowance dated Mar. 3, 2017", 8 pgs.

(56) References Cited

OTHER PUBLICATIONS

"U.S. Appl. No. 14/199,845, Preliminary Amendment filed Mar. 6, 2014", 6 pgs.
"U.S. Appl. No. 14/199,845, Response filed Jan. 30, 2017 to Final Office Action dated Sep. 29, 2016", 9 pgs.
"U.S. Appl. No. 14/199,845, Response filed Jun. 22, 2016 to Non Final Office Action dated Mar. 23, 2016", 9 pgs.
"U.S. Appl. No. 14/199,845, Response filed Jul. 10, 2015 to Non Final Office Action dated Mar. 12, 2015", 10 pgs.
"U.S. Appl. No. 14/199,845, Response filed Dec. 15, 2015 to Final Office Action dated Oct. 15, 2015", 10 pgs.
"U.S. Appl. No. 14/214,752, Non Final Office Action dated Mar. 26, 2019", 17 pgs.
"U.S. Appl. No. 14/295,735, Non Final Office Action dated Mar. 29, 2017", 15 pgs.
"U.S. Appl. No. 14/295,735, Notice of Allowance dated Dec. 12, 2017", 9 pgs.
"U.S. Appl. No. 14/295,735, Response filed Oct. 27, 2016 to Restriction Requirement dated Aug. 29, 2016", 10 pgs.
"U.S. Appl. No. 14/295,735, Restriction Requirement dated Aug. 29, 2016", 7 pgs.
"U.S. Appl. No. 14/296,735, Response filed Jun. 26, 2017 to Non Final Office Action dated Mar. 29, 2017", 10 pgs.
"U.S. Appl. No. 15/629,968, Examiner Interview Summary dated Mar. 25, 2019", 4 pgs.
"U.S. Appl. No. 15/629,968, Final Office Action dated Jul. 13, 2018", 12 pgs.
"U.S. Appl. No. 15/629,968, Non Final Office Action dated Jan. 8, 2018", 12 pgs.
"U.S. Appl. No. 15/629,968, Non Final Office Action dated Mar. 6, 2019", 11 pgs.
"U.S. Appl. No. 15/629,968, Preliminary Amendment filed Jun. 26, 2017", 7 pgs.
"U.S. Appl. No. 15/629,968, Response filed Mar. 22, 2018 to Non Final Office Action dated Jan. 8, 2018", 10 pgs.
"U.S. Appl. No. 15/629,968, Response filed Oct. 15, 2018 to Final Office Action dated Jul. 13, 2018", 11 pgs.
"U.S. Appl. No. 15/681,765, Amendment Under 37 CFR 1.114 filed Apr. 13, 2020", 6 pgs.
"U.S. Appl. No. 15/681,765, Final Office Action dated Sep. 16, 2019", 11 pgs.
"U.S. Appl. No. 15/681,765, Non Final Office Action dated Mar. 19, 2019", 11 pgs.
"U.S. Appl. No. 15/681,765, Notice of Allowance dated Jan. 13, 2020", 9 pgs.
"U.S. Appl. No. 15/681,765, Notice of Allowance dated May 5, 2020", 6 pgs.
"U.S. Appl. No. 15/681,765, Response filed Dec. 18, 2019 to Final Office Action dated Sep. 16, 2019", 8 pgs.
"U.S. Appl. No. 15/681,765, Response filed Jun. 19, 2019 to Non-Final Office Action dated Mar. 19, 2019", 8 pgs.
"U.S. Appl. No. 15/865,805, Non Final Office Action dated Oct. 22, 2019", 10 pgs.
"U.S. Appl. No. 15/865,805, Notice of Allowance dated Mar. 24, 2020", 5 pgs.
"U.S. Appl. No. 15/865,805, Response filed Jan. 23, 2020 to Non Final Office Action dated Oct. 22, 2019", 9 pgs.
"U.S. Appl. No. 15/865,805, Response filed Sep. 23, 2019 to Restriction Requirement dated Jul. 25, 2019", 8 pgs.
"U.S. Appl. No. 15/865,805, Restriction Requirement dated Jul. 25, 2019", 9 pgs.
"U.S. Appl. No. 15/945,028, Non Final Office Action dated Apr. 6, 2020", 7 pgs.
"U.S. Appl. No. 15/945,028, Response filed Feb. 4, 2020 to Restriction Requirement dated Nov. 18, 2019", 6 pgs.
"U.S. Appl. No. 15/945,028, Restriction Requirement dated Nov. 18, 2019", 7 pgs.
"U.S. Appl. No. 16/275,730, Non Final Office Action dated Jun. 8, 2021", 17 pgs.

"U.S. Appl. No. 16/275,730, Preliminary Amendment filed Mar. 7, 2019", 11 pgs.
"U.S. Appl. No. 16/275,730, Response filed Sep. 2, 2021 to Non Final Office Action dated Jun. 8, 2021", 16 pgs.
"Australian Application Serial No. Response filed Mar. 2, 2017 to Examiners Report dated May 2, 2016", 25 pgs.
"Australian Application Serial No. 2014233252, Response filed Feb. 28, 2017 to First Examiners Report dated Jun. 22, 2016", 9 pgs.
"Australian Application Serial No. 2014237683, Subsequent Examiners Report dated Apr. 12, 2017", 8 pgs.
"Australian Application Serial No. 2017204544, First Examination Report dated Nov. 29, 2017", 5 pgs.
"Australian Application Serial No. 2017204544, Response filed Sep. 11, 2018 to Subsequent Examiners Report dated May 4, 2018", 64 pgs.
"Australian Application Serial No. 2017204544, Subsequent Examiners Report dated May 4, 2018", 6 pgs.
"Australian Application Serial No. 2017204544, Voluntary Amendment filed Jul. 17, 2017", 8 pgs.
"Australian Application Serial No. 2018274915, First Examination Report dated Feb. 25, 2020", 3 pgs.
"Australian Application Serial No. 2018274915, Response Filed Jun. 25, 2020 to First Examination Report dated Feb. 25, 2020", 19 pgs.
"Australian Application Serial No. 2018274915, Response filed Nov. 30, 2020 to Subsequent Examiners Report dated Jul. 15, 2020", 18 pgs.
"Australian Application Serial No. 2018274915, Subsequent Examiners Report dated Jul. 15, 2020", 4 pgs.
"Canadian Application Serial No. 2,906,940, Office Action dated Jun. 20, 2017", 4 pgs.
"Canadian Application Serial No. 2,906,940, Response filed Feb. 2, 2017 to Office Action dated Aug. 2, 2016", 20 pgs.
"Chinese Application Serial No. 201480023976.9, Office Action dated Jun. 1, 2016", With English Translation, 18 pgs.
"Chinese Application Serial No. 201480023976.9, Office Action dated Dec. 30, 2016", With English translation, 12 pgs.
"Chinese Application Serial No. 201480023976.9, Response filed Mar. 10, 2017 to Office Action dated Dec. 30, 2016", w/ claims in English, 9 pgs.
"Chinese Application Serial No. 201480023976.9, Response filed Oct. 12, 2016 to Office Action dated Jun. 1, 2016", With English claims, 14 pgs.
"Chinese Application Serial No. 201480026970.7, Office Action dated Jan. 12, 2017", (with English translation), 11 pgs.
"Chinese Application Serial No. 201480026970.7, Office Action dated May 5, 2017", w/ brief summary from agent's letter, 4 pgs.
"Chinese Application Serial No. 201480026970.7, Response filed Mar. 24, 2017 to Office Action dated Jan. 12, 2017", w/ Claims in English, 17 pgs.
"Chinese Application Serial No. 201480026970.7, Response filed Jun. 28, 2017 to Office Action dated May 5, 2017", w/claims in English, 17 pgs.
"Chinese Application Serial No. 201480026970.7, Response filed Nov. 21, 2016 to Office Action dated Jul. 6, 2016", w/ claims in English, 134 pgs.
"Chinese Application Serial No. 201710757674.X, Office Action dated May 6, 2020", w/ English translation, 34 pgs.
"Chinese Application Serial No. 201710757674.X, Response filed Sep. 9, 2020 to Office Action dated May 6, 2020", w/ English claims, 33 pgs.
"European Application Serial No. 14715815.8, Communication Pursuant to Article 94(3) EPC dated May 8, 2017", 7 pgs.
"European Application Serial No. 14715815.8, Response filed Oct. 16, 2017 to Communication Pursuant to Article 94(3) EPC dated May 8, 2017", 12 pgs.
"European Application Serial No. 18712707.1, Response to Communication Pursuant to Rules 161 and 162 filed Mar. 17, 2020", 13 pgs.
"European Application Serial No. 19179413.0, Extended European Search Report dated Nov. 8, 2019", 7 pgs.

(56) References Cited

OTHER PUBLICATIONS

"European Application Serial No. 19179413.0, Response filed Jun. 24, 2020 to Extended European Search Report dated Nov. 8, 2019", 14 pgs.
"European Application Serial No. 21169424.5, Extended European Search Report dated Aug. 11, 2021", 7 pgs.
"International Application Serial No. PCT/US2014/021397, International Preliminary Report on Patentability dated Sep. 24, 2015", 9 pgs.
"International Application Serial No. PCT/US2014/021397, International Search Report dated Jun. 10, 2014", 4 pgs.
"International Application Serial No. PCT/US2014/40860, International Preliminary Report on Patentability dated Dec. 17, 2015", 8 pgs.
"International Application Serial No. PCT/US2014/40860, International Search Report dated Oct. 9, 2014", 3 pgs.
"International Application Serial No. PCT/US2014/40860, Written Opinion dated Oct. 9, 2014", 6 pgs.
"International Application Serial No. PCT/US2017/047784, International Preliminary Report on Patentability dated Mar. 7, 2019", 9 pgs.
"International Application Serial No. PCT/US2017/047784, International Search Report dated Jan. 23, 2018", 8 pgs.
"International Application Serial No. PCT/US2017/047784, Invitation to Pay Additional Fees and Partial Search Report dated Nov. 3, 2017", 11 pgs.
"International Application Serial No. PCT/US2017/047784, Written Opinion dated Jan. 23, 2018", 7 pgs.
"International Application Serial No. PCT/US2018/012930, International Preliminary Report on Patentability dated Jul. 25, 2019", 7 pgs.
"International Application Serial No. PCT/US2018/012930, International Search Report dated Jun. 26, 2018", 4 pgs.
"International Application Serial No. PCT/US2018/012930, Written Opinion dated Jun. 26, 2018", 7 pgs.
"Japanese Application Serial No. 2016-503289, Examiners Decision of Final Refusal dated Jan. 9, 2018", (English Translation), 5 pgs.
"Japanese Application Serial No. 2016-503289, Office Action dated Jun. 5, 2017", with English translation, 7 pgs.
"Japanese Application Serial No. 2016-503289, Response filed Nov. 2, 2017 to Office Action dated Jun. 5, 2017", w/ claims in English, 9 pgs.
Blum, David, et al., "Systems and Methods for Closed-Loop Determination of Stimulation Parameter Settings for an Electrical Simulation System", U.S. Appl. No. 62/408,620, filed Oct. 14, 2016, 76 pgs.
Carcieri, Stephen, "Neurostimulation System and Method for Automatically Adjusting Stimulation and Reducing Energy Requirements Using Evoked Action Potential", U.S. Appl. No. 61/768,295, filed Feb. 22, 2013.
Dayan, Peter, et al., "Theoretical Neuroscience", Chapter 7 (MIT Press 2001) 54 pages.
De Hemptinne, Coralie, et al., "Exaggerated phase-amplitude coupling in the primary motor cortex in Parkinson disease", PNAS, vol. 110, No. 12, (Mar. 19, 2013), 4780-4785.
Gerstner, Wulfram, et al., "Spiking Neuron Models, Single Neurons, Populations, Plasticity", Chapter 4 (Cambridge University Press), 66 pages 2002.
Hammond, Constance, "Pathological synchronization in Parkinson's disease: networks, models and treatments", Trends in Neuroscience, vol. 30, No. 7, (May 25, 2007), 357-364.
Lee, Dongchul, "Method for Selectively Modulating Nerve Endings in Spinal Cord", U.S. Appl. No. 61/703,195, filed Sep. 19, 2012.
Lee, Dongchul, et al., "Method for Selectively Modulating Neural Elements in the Dorsal Horn", U.S. Appl. No. 13/843,102, filed Mar. 15, 2013, 28 pgs.
Lee, Dongchul, et al., "Neurostimulation System for Defining a Generalized Ideal Multipole Configuration", U.S. Appl. No. 61/452,965, filed Mar. 15, 2011.
Rao, Prakash, et al., "Technique for Linking Electrodes Together During Programming of Neurostimulation System", U.S. Appl. No. 61/561,760, filed Nov. 18, 2011.
Steinke, G. Karl, et al., "Systems and Methods for Making and Using Improved Contact Arrays for Electrical Stimulation Systems", U.S. Appl. No. 62/113,291, filed Feb. 6, 2015.
Tass, P.A., "Desynchronization by Means of a Coordinated Reset of Neural Sub-Populations", Progress of Theoretical Physics Supplement, No. 150, 281-296 (2003).
Tort, Adriano, et al., "Measuring Phase-Amplitude Coupling Between Neuronal Oscillations of Different Frequencies", J Neurophysiol 104, (2010), 1195-1210.
Vansickle, Dennis Allen, et al., "Neuromodulation System and Method for Transitioning Between Programming Modes", U.S. Appl. No. 14/214,752, filed Mar. 15, 2014, 159 pgs.
Vansickle, Dennis Allen, "Systems and Methods for Delivering Sub-Threshold Therapy to a Patient", U.S. Appl. No. 61/801,917, filed Mar. 15, 2013.
Zhang, T.C., et al., "Modeling effects of spinal cord stimulation on wide-dynamic range dorsal horn neurons: influence of stimulation frequency and GABAergic inhibition", J Neurophysiol 112: 552-567, 2014.

* cited by examiner

FIG. 13

NEUROMODULATION SYSTEM AND METHOD FOR TRANSITIONING BETWEEN PROGRAMMING MODES

RELATED APPLICATION DATA

The present application is a continuation of U.S. application Ser. No. 14/214,752, filed Mar. 15, 2013, which claims the benefit under 35 U.S.C. § 119 to U.S. provisional patent application Ser. No. 61/801,917, filed Mar. 15, 2013. The foregoing application is hereby incorporated by reference into the present application in its entirety.

FIELD OF THE INVENTION

The present inventions relate to tissue modulation systems, and more particularly, to programmable neuromodulation systems.

BACKGROUND OF THE INVENTION

Implantable neuromodulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neuromodulation systems typically include one or more electrode carrying neuromodulation leads, which are implanted at the desired modulation site, and an implantable neuromodulation device (e.g., an implantable pulse generator (IPG)) implanted remotely from the modulation site, but coupled either directly to the neuromodulation lead(s) or indirectly to the neuromodulation leads) via a lead extension. The neuromodulation system may further comprise a handheld external control device (e.g., a remote control (RC)) to remotely instruct the neuromodulator to generate electrical pulses in accordance with selected modulation parameters.

Implantable neuromodulation devices are active devices requiring energy for operation, and thus, the neuromodulation system oftentimes include an external charger to recharge a neuromodulation device, so that a surgical procedure to replace a power depleted neuromodulation device can be avoided. To wirelessly convey energy between the external charger and the implanted neuromodulation device, the charger typically includes an alternating current (AC) charging coil that supplies energy to a similar charging coil located in or on the neuromodulation device. The energy received by the charging coil located on the neuromodulation device can then be stored in a rechargeable battery within the neuromodulation device, which can then be used to power the electronic componentry on-demand. Depending on the settings, the neuromodulation device may need to be recharged every 1-30 days.

Electrical modulation energy may be delivered from the neuromodulation device to the electrodes in the form of an electrical pulsed waveform. Thus, electrical modulation energy may be controllably delivered to the electrodes to modulate neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, width, and rate of the electrical pulses provided through the electrode array. Each electrode configuration, along with the electrical pulse parameters, can be referred to as a "modulation parameter set."

With some neuromodulation systems, and in particular, those with independently controlled current or voltage sources, the distribution of the current to the electrodes (including the case of the neuromodulation device, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode configurations).

As briefly discussed above, an external control device can be used to instruct the neuromodulation device to generate electrical pulses in accordance with the selected modulation parameters. Typically, the modulation parameters programmed into the neuromodulation device can be adjusted by manipulating controls on the external control device to modify the electrical modulation energy delivered by the neuromodulation device system to the patient. Thus, in accordance with the modulation parameters programmed by the external control device, electrical pulses can be delivered from the neuromodulation device to the electrode(s) to modulate a volume of tissue in accordance with a set of modulation parameters and provide the desired efficacious therapy to the patient. The best modulation parameter set will typically be one that delivers electrical energy to the volume of tissue that must be modulate in order to provide the therapeutic benefit (e.g., treatment of pain), while minimizing the volume of non-target tissue that is modulated.

However, the number of electrodes available, combined with the ability to generate a variety of complex electrical pulses, presents a huge selection of modulation parameter sets to the clinician or patient. For example, if the neuromodulation system to be programmed has an array of sixteen electrodes, millions of modulation parameter sets may be available for programming into the neuromodulation system. Today, neuromodulation system may have up to thirty-two electrodes, thereby exponentially increasing the number of modulation parameters sets available for programming.

To facilitate such selection, the clinician generally programs the neuromodulation device through a computerized programming system. This programming system can be a self-contained hardware/software system, or can be defined predominantly by software running on a standard personal computer (PC). The PC or custom hardware may actively control the characteristics of the electrical pulses generated by the neuromodulation device to allow the optimum modulation parameters to be determined based on patient feedback or other means and to subsequently program the neuromodulation device with the optimum modulation parameter set or sets. The computerized programming system may be operated by a clinician attending the patient in several scenarios.

For example, in order to achieve an effective result from conventional SCS, the lead or leads must be placed in a location, such that the electrical modulation (and in this case, electrical stimulation) will cause paresthesia. The paresthesia induced by the stimulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy. When leads are implanted within the patient, the computerized programming system, in the context of an operating room (OR) mapping procedure, may be used to instruct the neuromodulation device to apply electrical stimulation to test placement of the leads and/or electrodes, thereby assuring that the leads and/or electrodes are implanted in effective locations within the patient.

Once the leads are correctly positioned, a fitting procedure, which may be referred to as a navigation session, may be performed using the computerized programming system to program the external control device, and if applicable the neuromodulation device, with a set of modulation parameters that best addresses the painful site. Thus, the navigation session may be used to pinpoint the volume of activation (VOA) or areas correlating to the pain. Such programming ability is particularly advantageous for targeting the tissue during implantation, or after implantation should the leads gradually or unexpectedly move that would otherwise relocate the stimulation energy away from the target site. By reprogramming the neuromodulation device (typically by independently varying the stimulation energy on the electrodes), the volume of activation (VOA) can often be moved back to the effective pain site without having to re-operate on the patient in order to reposition the lead and its electrode array. When adjusting the volume of activation (VOA) relative to the tissue, it is desirable to make small changes in the proportions of current, so that changes in the spatial recruitment of nerve fibers will be perceived by the patient as being smooth and continuous and to have incremental targeting capability.

One known computerized programming system for SCS is called the Bionic Navigator®, available from Boston Scientific Neuromodulation Corporation. The Bionic Navigator® is a software package that operates on a suitable PC and allows clinicians to program modulation parameters into an external handheld programmer (referred to as a remote control). Each set of modulation parameters, including fractionalized current distribution to the electrodes (as percentage cathodic current, percentage anodic current, or off), may be stored in both the Bionic Navigator® and the remote control and combined into a stimulation program that can then be used to stimulate multiple regions within the patient.

To determine the modulation parameters to be programmed, the Bionic Navigator® may be operated by a clinician in one of three modes: (a) a manual programming mode to manually select the cathodic current and anodic current flowing through the electrodes; (b) an electronic trolling ("e-troll") mode to quickly sweep the electrode array using a limited number of electrode configurations to gradually move a cathode in bipolar stimulation; and (c) a Navigation programming mode to fine tune and optimize stimulation coverage for patient comfort using a wide number of electrode configurations. These three modes allow the clinician to determine the most efficient modulation parameter sets for a given patient.

In the manual programming mode, the clinician directly selects individual electrodes and the current magnitude and polarity to be applied to each selected electrode. In the e-troll and navigation programming modes, the Bionic Navigator® semi-automatically transitions between different electrode configurations to electrically "steer" the current along the implanted leads in real-time (e.g., using a joystick or joystick-like controls) in a systematic manner, thereby allowing the clinician to determine the most efficacious modulation parameter sets that can then be stored and eventually combined into stimulation programs. In the context of SCS, current steeling is typically either performed in a rostro-caudal direction (i.e., along the axis of the spinal cord) or a medial-lateral direction (i.e., perpendicular to the axis of the spinal cord).

The e-troll and navigation programming modes differ in part in the way in which the clinician changes electrode configurations from one configuration to another. The e-troll programming mode utilizes a technique known as "panning", which shifts a pre-defined electrode configuration down the sequence of electrodes without changing the basic form of the electrode configuration. The navigation programming mode utilizes a technique known as "weaving," which moves the anode or anodes around the cathode, while slowly progressing the cathode down the sequence of electrodes. The e-troll and navigation programming modes may have different clinical uses (e.g., finding the "sweet spot" in the case of panning, or shaping the electrical field around the cathode in the case of weaving).

In one novel current steering method, described in U.S. patent application Ser. No. 12/938,282, entitled "System and Method for Mapping Arbitrary Electric Fields to Pre-existing Lead Electrodes," which is expressly incorporated herein by reference, a stimulation target in the form of a virtual pole (e.g., a virtual bipole or tripole) is defined and the modulation parameters, including the fractionalized current values on each of the electrodes, are computationally determined in a manner that emulates these virtual poles. It can be appreciated that current steering can be implemented by moving the virtual poles about the leads, such that the appropriate fractionalized current values for the electrodes are computed for each of the various positions of the virtual pole. As a result, the current steering can be implemented using an arbitrary number and arrangement of electrodes, thereby solving the afore-described problems.

The virtual bipole or tripole can be determined using a simplified virtual tri pole consisting of a cathode, and an upper (or rostral) anode and lower (or caudal) electrode located on a longitudinal axis from the cathode. The virtual tripole may be defined using three values consisting of (1) location of the cathode relative to the electrodes; (2) a focus, which is the distance between the cathode and the anode(s); and (3) a percentage of current on the upper cathode. This technique is described in U.S. Provisional Patent Application Ser. No. 61/452,965, entitled "Neurostimulation System for Defining a Generalized Virtual Multipole," which is expressly incorporated herein by reference.

Although alternative or artifactual sensations are usually tolerated relative to the sensation of pain, patients sometimes report these sensations to be uncomfortable, and therefore, they can be considered an adverse side-effect to neuromodulation therapy in some cases. Because the perception of paresthesia has been used as an indicator that the applied electrical energy is, in fact, alleviating the pain experienced by the patient, the amplitude of the applied electrical energy is generally adjusted to a level that causes the perception of paresthesia. 1t has been shown that the delivery of sub-threshold electrical energy (e.g., high-rate pulsed electrical energy and/or low pulse width electrical energy) can be effective in providing neuromodulation therapy for chronic pain without causing paresthesia.

However, because there is a lack of paresthesia that may otherwise indicate that the activated electrodes are properly located relative to the targeted tissue site, it is difficult to immediately determine if the delivered sub-threshold neuromodulation therapy is optimized in terms of both providing efficacious therapy and minimizing energy consumption. Furthermore, if the implanted neuromodulation lead(s) migrate relative to the target tissue site to be modulated, it is possible that the sub-threshold neuromodulation may fall outside of the effective therapeutic range (either below the therapeutic range if the coupling efficiency between the neuromodulation lead(s) and target tissue site decreases, resulting in a lack of efficacious therapy, or above the therapeutic range if the coupling efficiency between the neuromodulation lead(s) and the target tissue site increases, resulting in the perception of paresthesia or inefficient energy consumption).

There, thus, remains a need to provide a neuromodulation system that is capable of compensating for the migration of neuromodulation lead(s) during sub-threshold neuromodulation therapy.

Another issue is that a patient receiving sub-threshold therapy may not notice when the battery of the implanted neuromodulation device has depleted, and because the sub-threshold therapy is not accompanied by paresthesia, the patient may not immediately realize that he or she is no longer receiving therapy. There, thus, remains a need to alert a patient when the battery of an implanted neuromodulation is almost depleted.

Conventional computerized programming systems typically have one or more programming modes intended to achieve a singular therapeutic effect (e.g., either super-threshold neuromodulation therapy (e.g., therapy accompanied by paresthesia) or sub-threshold neuromodulation therapy (e.g., therapy not accompanied by paresthesia). To this end, a particular computer programming system will typically limit the modulation parameters with which a neuromodulation device can be programmed. For example, a computerized programming system designed for super-threshold neuromodulation may limit the modulation parameters to those known to result in super-threshold neuromodulation therapy, whereas a computerized programming system designed for subthreshold neuromodulation may limit the modulation parameters to those known to result in sub-threshold neuromodulation therapy. To the extent that a particular computer programming system has one or more programming modes that are capable of providing multiple therapeutic effects (e.g., both super-threshold neuromodulation therapy and sub-threshold neuromodulation therapy), there is no known computer programming system that transitions between multiple programming modes that have been optimized to respectively achieve multiple therapeutic effects.

There, thus, remains a need to provide a computer programming system capable of transitioning between multiple programming modes designed to achieve different therapeutic results, such as super-threshold therapy and sub-threshold therapy.

Furthermore, while it is possible, using conventional computerized programming systems, to program a neuromodulator and the accompanying with both super-threshold modulation programs and sub-threshold modulation programs, this requires an extensive programming or reprogramming fitting session to determine the optimum modulation programs, typically requiring the presence of a clinician. Furthermore, assuming that the neuromodulator and the accompanying handheld external control device have been programmed to selectively deliver super-threshold neuromodulation therapy or sub-threshold neuromodulation therapy, the user may still be required to navigate through a series of steps (e.g., via menus) to switch between the super-threshold and sub-threshold modulation programs. There, thus remains a need to provide the user with a more efficient means for switching between super-threshold modulation therapy and sub-threshold modulation therapy.

Furthermore, while super-threshold neuromodulation and sub-threshold neuromodulation may provide different mechanisms for providing therapy to a patient, under the assumption that a patient needs only one or the other of these therapies, neuromodulation systems have typically been programmed to take advantage of only one of these therapies at any given time. There, thus, remains a need deliver super-threshold modulation energy and sub-threshold modulation therapy in a synergistic fashion.

SUMMARY OF THE INVENTION

In accordance with one aspect of the present inventions, an external control device for programming an implantable neuromodulator coupled to an electrode array is provided. The external control device comprises a user interface including a programming selection control element configured for allowing a user to select one of a first programming mode (e.g., a semi-automated programming mode) having a first limit on a modulation parameter and a second programming mode (e.g., a semi-automated programming mode) having a second limit on the modulation parameter different from the first limit. In one embodiment, the modulation parameter is a pulse rate, in which case, the first limit may be, e.g., an upper limit value less than 1500 Hz, and the second limit may be, e.g., a lower limit value greater than 1500 Hz. In another embodiment, the modulation parameter is a pulse width, in which case, the first limit may be, e.g., a lower limit value greater than 100 μs, and the second limit may be, e.g., an upper limit value less than 100 μs. In still another embodiment, the modulation parameter is an electrode combination (e.g., a fractionalized electrode combination), in which case, the first limit may be, e.g., a range of electrode combinations having only anodic electrodes as primary modulating electrodes, and the second limit may be, e.g., a range of electrode combinations having only cathodic electrodes as primary modulating electrodes, or the first limit may be, e.g., a range of monopolar electrode combinations, and the second limit may be, e.g., a range of multipolar electrode combinations.

The external control device further comprises controller/processor circuitry configured for allowing a user to program the neuromodulator in the first programming mode, and allowing the user to program the neuromodulator in the second programming mode in response to actuation of the programming selection control element. The external control device may further comprise telemetry circuitry, in which case, the controller/processor circuitry may be configured for programming the neuromodulator via the telemetry circuitry. The external control device may further comprise a housing containing the user interface and the controller/processor circuitry.

In one embodiment, the controller/processor circuitry may be configured for defining a virtual multipole relative to the electrode array when programming the neuromodulator in the first programming mode, and computing amplitude values for the electrode array that emulate the virtual multipole, wherein the first modulation parameter set includes the computed amplitude values. Each of the first and second programming modes may be a semi-automated programming mode configured for panning the virtual multipole across the electrode array.

In another embodiment, the controller/processor circuitry may be configured for defining a series of modulation parameter sets during the programming of the neuromodulator in the first programming mode, and instructing the neuromodulator to convey electrical energy to the electrode array in accordance with the series of modulation parameter sets in a manner that displaces a locus of a resulting electrical field relative to the electrode array. In this case, the controller/processor circuitry, in response to the actuation of the programming selection control element, may be configured for deriving another modulation parameter set from the last modulation parameter set of the series of modulation parameter sets, and instructing the neuromodulator to convey electrical energy to the electrode array in accordance with the other modulation parameter set during the programming of the neuromodulation to device in the second programming mode. The controller/processor circuitry may further be configured for deriving the other modulation parameter set in a manner that causes an electrical field resulting from the conveyance of the electrical energy to the electrode array in accordance with the other modulation parameter set to have a locus that is the same as the locus of the electrical field resulting from the conveyance of the electrical energy to the electrode array in accordance with the last modulation parameter set.

In accordance with a second aspect of the present inventions, a method of operating an implantable neuromodulator coupled to an electrode array implanted adjacent tissue (e.g., spinal cord tissue) of a patient having a medical condition (e.g., chronic pain) is provided. The neuromodulator may be implanted within the patient. The method comprises conveying electrical modulation energy to tissue of the patient in accordance with a series of modulation parameter sets, thereby gradually displacing the locus of the resulting electrical field relative to the tissue, such that a plurality of different loci of the resulting electrical field can be respectively associated with the series of modulation parameter sets. The method further comprises causing the patient to perceive paresthesia in response to the conveyance of the electrical modulation energy to the tissue in accordance with at least one of the modulation parameter sets, identifying one of the at least one modulation parameter sets based on the perceived paresthesia, and deriving another modulation parameter set from the identified modulation parameter set.

In one method, the identified modulation parameter set and the other modulation parameter set define different pulse rates, in which case, the identified modulation parameter set may, e.g., define a pulse rate less than 1500 Hz, and the other modulation parameter set may, e.g., define a pulse rate greater than 1500 Hz. In another method, the identified modulation parameter set and the other modulation parameter set define different pulse widths, in which case, the identified modulation parameter set may, e.g., define a pulse width greater than 100 and the other modulation parameter set may, e.g., define a pulse width less than 100 µs. In still another method, the identified modulation parameter set and the other modulation parameter set define different electrode combinations (e.g., different fractionalized electrode combinations), in which case, the identified modulation parameter set may, e.g., be a monopolar electrode combination, and the other modulation parameter set may, e.g., be a multipolar electrode combination.

The method further comprises conveying electrical modulation energy to the tissue of the patient in accordance with the other modulation parameter set, thereby creating an electrical field having a locus relative to the tissue that is the same as the locus of the electrical field associated with the identified modulation parameter set, and without causing the patient to perceive paresthesia. The neuromodulator may be programmed with the other modulation parameter set. In one method, the medical condition affects a body region of the patient, in which case, the electrical modulation energy conveyed to the tissue in accordance with the identified modulation parameter set may cause the patient to perceive the paresthesia in the body region.

The method may optionally comprise defining a series of virtual poles relative to the electrode array (e.g., by panning a virtual pole across the electrode array), computing amplitude values for electrode combinations that respectively emulate the series of virtual poles, such that the series of modulation parameter sets respectively define the electrode combinations, defining another virtual pole relative to the electrode array, and computing amplitude values for another electrode combination that emulates the other virtual pole, such that the other modulation parameter set defines the other electrode combination.

In accordance with a third aspect of the present inventions, an external control device for programming an implantable neuromodulator coupled to an electrode array implanted within a patient is provided. The external control device comprises a user interface including a control element, and telemetry circuitry configured for communicating with the neuromodulator. The external control device further comprises controller/processor circuitry configured for, in response to an event (e.g., a user action of a second control element on the user interface, a signal indicating migration of the implanted electrode array within the patient, or a temporal occurrence), directing the neuromodulator via the telemetry circuitry to deliver electrical modulation energy to the electrode array at incrementally increasing amplitude values. In one embodiment, the user interface includes a second control element, and the event is a user actuation of the second control element.

The controller/processor circuitry is further configured for automatically computing, in response to the actuation of the control element, a decreased amplitude value as a function of one of the incrementally increased amplitude values e.g., the last incrementally increased amplitude value), and directing the neuromodulator via the telemetry circuitry to deliver electrical modulation energy to the electrode array at the computed amplitude value. In one embodiment, the computed function is a percentage (e.g., in the range of 30%-70%, and more specifically, in the range of 40%-60%) of the one incrementally increased amplitude value. In another embodiment, the computed function is a difference between the one incrementally increased amplitude value and a constant. The external control device may further comprise a housing containing the user interface, the telemetry circuitry, and the controller/processor circuitry. If the electrical modulation energy comprises an electrical pulse train, each of the incrementally increased amplitude values and the computed amplitude value may be a pulse amplitude value.

In accordance with a fourth aspect of the present inventions, a neuromodulation system is provided. The neuromodulation system comprises an electrode array, and an implantable neuromodulator (which may be implantable) coupled to the electrode array. The neuromodulation system further comprises an external control device configured for, in response to an event (e.g., another user input, a signal indicating migration of the implanted electrode array within the patient, or a temporal occurrence), directing the neuromodulator to deliver electrical modulation energy to the electrode array at incrementally increasing amplitude values, automatically computing a decreased amplitude value as a function of one of the incrementally increased amplitude values (e.g., the last incrementally increased amplitude value), and directing the neuromodulator to deliver electrical modulation energy to the electrode array at the computed amplitude value. In one embodiment, the computed function is a percentage (e.g., in the range of 30%-70%, and more specifically, in the range of 40%-60%) of the one incrementally increased amplitude value. In another embodiment, the computed function is a difference between the one incrementally increased amplitude value and a constant. In an optional embodiment, the neuromodulation system further comprises a sensor configured for measuring a physiological parameter indicating super-threshold stimulation of neural tissue. If the electrical modulation energy comprises an electrical pulse train, each of the incrementally increased amplitude values and the computed amplitude value may be a pulse amplitude value.

In accordance with a fifth aspect of the present inventions, a method of providing therapy to a patient is provided. The method comprises delivering electrical modulation energy to a target tissue site of the patient at a programmed amplitude value, thereby providing therapy to the patient without the perception of paresthesia. The method further comprises delivering electrical modulation energy to the patient at a series of incrementally increasing amplitude values relative to the programmed amplitude value until the patient perceives paresthesia. If the patient suffers from chronic pain in a body region, the paresthesia may be perceived by the patient in the body region.

The method further comprises automatically computing a decreased amplitude value as a function of one of the series of incrementally increased amplitude values (e.g., the last incrementally increased amplitude value) at which the delivered electrical modulation caused the patient to perceive the paresthesia, and delivering electrical modulation energy to the target tissue site of the patient at the computed amplitude value, thereby providing therapy to the patient without the perception of paresthesia. In one method, the computed function is a percentage (e.g., in the range of 30%-70%, and more specifically, in the range of 40%-60%) of the one incrementally increased amplitude value. In another method, the computed function is a difference between the one incrementally increased amplitude value and a constant.

If the delivered electrical modulation energy comprises an electrical pulse train, each of the programmed amplitude value, incrementally increased amplitude value, and computed amplitude value may be a pulse amplitude value. In one method, the electrical modulation energy is delivered from at least one electrode implanted in the patient to the target tissue site at the programmed amplitude value, the electrode(s) migrates relative to the target tissue site when the electrical modulation energy is delivered to the target tissue site at the programmed amplitude value, and the series of amplitude values are generated after the at least one electrode migrates relative to the target tissue site.

In accordance with a sixth aspect of the present inventions, an external control device for programming an implantable neuromodulator coupled to an electrode array implanted within a patient is provided. The neuromodulator is configured for being operated in a super-threshold, such that the neuromodulator delivers electrical modulation energy configured for providing super-threshold therapy to the patient (e.g., at a pulse rate less than 1500 Hz, and more specifically, less than 500 Hz; or at a pulse width greater than 100 µs, and more specifically greater than 200 µs), and a sub-threshold delivery mode, such that the neuromodulator delivers electrical modulation energy configured for providing sub-threshold therapy to the patient (e.g., at a pulse rate greater than 1500 Hz, and more specifically, greater than 2500 Hz; or at a pulse width less than 100 µs, and more specifically less than 50 µs). The neuromodulator may optionally be configured for being operated in a hybrid delivery mode, such that the neuromodulator delivers electrical modulation energy configured for providing both super-threshold therapy and sub-threshold therapy to the patient.

The external control device comprises a user interface including a control element, telemetry circuitry configured for communicating with the neuromodulator, and controller/processor circuitry configured for, in response to a single actuation of the control element, directing the neuromodulator via the telemetry circuitry to switch between the super-threshold delivery mode and the sub-threshold delivery mode. If the neuromodulator is configured for being operated in a hybrid delivery mode, the controller/processor circuitry may be further configured for, in response to another single actuation of the control element, directing the neuromodulator via the telemetry circuitry to switch between one or both of the super-threshold delivery mode and the sub-threshold delivery mode, and the hybrid delivery mode. The external control device may further comprise a housing containing the user interface, the telemetry circuitry, and the controller/processor circuitry.

In one embodiment, the controller/processor circuitry is configured for, in response to a toggling actuation of the control element, directing the neuromodulator to switch back and forth between the super-threshold delivery mode and the sub-threshold delivery mode. In another embodiment, the controller/processor circuitry is configured for, in response to the single actuation of the control element, selecting between a pre-existing super-threshold modulation program and a pre-existing sub-threshold modulation program, for directing the neuromodulator to operate in the super-threshold delivery mode in order to deliver the electrical modulation energy in accordance with the super-threshold modulation program, and for directing the neuromodulator to operate in the sub-threshold delivery mode in order to deliver the electrical modulation energy in accordance with the sub-threshold modulation program. In still another embodiment, the controller/processor is configured for, in response to the single actuation of the control element, deriving a new modulation program from a pre-existing modulation program, for directing the neuromodulator to operate in the super-threshold delivery mode in order to deliver the electrical modulation energy in accordance with one of the new modulation program and the pre-existing modulation program, and for directing the neuromodulator to operate in the sub-threshold delivery mode in order to deliver the electrical modulation energy in accordance with the other of the new modulation program and the pre-existing modulation program.

In accordance with a seventh aspect of the present inventions, a neuromodulation system is provided. The neuromodulation system comprises an electrode array, and an implantable neuromodulator coupled to the electrode array. The neuromodulator is configured for being selectively placed between a super-threshold delivery mode that delivers electrical modulation energy to the electrode array configured for providing super-threshold therapy to a patient (e.g., at a pulse rate less than 1500 Hz, and more specifically, less than 500 Hz; or at a pulse width greater than 100 µs, and more specifically greater than 200 µs), and a sub-threshold delivery mode that delivers electrical modulation energy to the electrode array configured for providing sub-threshold therapy to the patient (e.g., at a pulse rate greater than 1500 Hz, and more specifically, greater than 2500 Hz; or at a pulse width less than 100 µs, and more specifically less than 50 µs). The neuromodulator may optionally be configured for being operated in a hybrid delivery mode, such that the neuromodulator delivers electrical modulation energy configured for providing both super-threshold therapy and sub-threshold therapy to the patient.

The neuromodulation system further comprises an external control device configured for, in response to a single user actuation of a control element, directing the neuromodulator to switch between the super-threshold delivery mode and the sub-threshold delivery mode. If the neuromodulator is configured for being operated in a hybrid delivery mode, the external control device may be further configured for, in response to another single actuation of the control element, directing the neuromodulator to switch between one or both of the super-threshold delivery mode and the sub-threshold delivery mode, and the hybrid delivery mode.

In one embodiment, the external control device is configured for, in response to a toggling actuation of the control element, directing the neuromodulator to switch back and forth between the super-threshold delivery mode and the sub-threshold delivery mode. In another embodiment, the external control device is configured for, in response to the single actuation of the control element, selecting between a pre-existing super-threshold modulation program and a pre-existing sub-threshold modulation program, for directing the neuromodulator to operate in the super-threshold delivery mode in order to deliver the electrical modulation energy in accordance with the super-threshold modulation program, and for directing the neuromodulator to operate in the sub-threshold delivery mode in order to deliver the electrical modulation energy in accordance with the sub-threshold modulation program. In still another embodiment, the external control device is configured for, in response to the single actuation of the control element, deriving a new modulation program from a pre-existing modulation program, for directing the neuromodulator to operate in the super-threshold delivery mode in order to deliver the electrical modulation energy in accordance with one of the new modulation program and the pre-existing modulation program, and for directing the neuromodulator to operate in the sub-threshold delivery mode in order to deliver the electrical modulation energy in accordance with the other of the new modulation program and the pre-existing modulation program.

In accordance with an eighth aspect of the present inventions, a method of providing therapy to a patient using an implantable neuromodulator implanted within the patient and an external control device is provided. The method comprises operating the neuromodulator in one of a super-threshold delivery mode and a sub-threshold delivery mode, and switching operation of the neuromodulator to the other of the super-threshold delivery mode and the sub-threshold delivery mode. The neuromodulator delivers electrical modulation energy to the patient when in the super-threshold delivery mode that provides super-threshold therapy to the patient (e.g., at a pulse rate less than 1500 Hz, and more specifically, less than 500 Hz; or at a pulse width greater than 100 µs, and more specifically greater than 200 µs), and delivers electrical modulation energy to the patient when in the sub-threshold delivery mode that provides sub-threshold therapy to the patient (e.g., at a pulse rate greater than 1500 Hz, and more specifically, greater than 2500 Hz; or at a pulse width less than 100 µs, and more specifically less than 50 µs). If the patent suffers from chronic pain in a body region, paresthesia may be perceived by the patient in the body region when the modulation energy is delivered to the patient when the neuromodulator is in the super-threshold delivery mode. The method optionally comprises switching operation of the neuromodulator to a hybrid delivery mode. In this case, the neuromodulator delivers electrical modulation energy to the patient when in the hybrid delivery mode that provides both super-threshold and sub-threshold therapy to the patient.

One method further comprises switching operation of the neuromodulator back and forth between the super-threshold delivery mode and the sub-threshold delivery mode. Another method further comprises deriving a new modulation program from a pre-existing modulation program, in which case, the neuromodulator delivers the electrical modulation energy to the patient in accordance with the pre-existing modulation program when in the one of the super-threshold delivery mode and the sub-threshold delivery mode, and delivers the electrical modulation energy to the patient in accordance with the new modulation program when in the other of the super-threshold delivery mode and the sub-threshold delivery mode.

In accordance with a ninth aspect of present inventions, an external control device for programming an implantable neuromodulator coupled to an electrode array implanted within a patient is provided. The external control device comprises a user interface configured for receiving input from a user, telemetry circuitry configured for communicating with the neuromodulator, and controller/processor circuitry configured for, in response to the user input, deriving a new modulation program from a pre-existing modulation program, and directing the neuromodulator to deliver modulation energy in accordance with the new modulation program. The pre-existing modulation program is one of a super-threshold modulation program (e.g., at a pulse rate less than 1500 Hz, and more specifically, less than 500 Hz; or at a pulse width greater than 100 µs, and more specifically greater than 200 µs) and a sub-threshold modulation program (e.g., at a pulse rate greater than 1500 Hz, and more specifically, greater than 2500 Hz; or at a pulse width less than 100 µs, and more specifically less than 50 µs), and the new modulation program is the other of the super-threshold modulation program and the sub-threshold modulation program. The external control device may further comprise a housing containing the user interface, the telemetry circuitry, and the controller/processor circuitry. In an optional embodiment, controller/processor circuitry is configured for, in response to another user input, deriving another new modulation program from the pre-existing modulation program, and directing the neuromodulator to deliver modulation energy in accordance with the other new modulation program. The other new modulation program comprises a hybrid modulation program.

In one embodiment, the controller/processor circuitry is configured for deriving the new modulation program from the pre-existing modulation program by computing a pulse amplitude value as a function of the pulse amplitude value of the pre-existing modulation program and including the computed pulse amplitude value in the new modulation program. The function of the pulse amplitude value may be a percentage of the pulse amplitude value. For example, the percentage may be in the range of 30%-70% if the new modulation program is the sub-threshold modulation program, and in the range of 150%-300% if the new modulation program is the super-threshold modulation program, More specifically, the percentage may be in the range of 40%-60% if the new modulation program is the sub-threshold modulation program, and in the range of 175%-250% if the new modulation program is the super-threshold modulation program. As another example, the function of the pulse amplitude value may be one of a difference between the pulse amplitude and a constant and a summation of the pulse amplitude and the constant.

In accordance with a tenth aspect of the present inventions, a neuromodulation system is provided. The neuromodulation system comprises an electrode array and an implantable neuromodulator coupled to the electrode array. The neuromodulator is configured for being selectively placed between a super-threshold delivery mode that delivers electrical modulation energy to the electrode array configured for providing super-threshold therapy to a patient (e.g., at a pulse rate less than 1500 Hz, and more specifically, less than 500 Hz; or at a pulse width greater than 100 µs, and more specifically greater than 200 µs), and a sub-threshold delivery mode that delivers electrical modulation energy to the electrode array configured for providing sub-threshold therapy to the patient (e.g., at a pulse rate greater than 1500 Hz, and more specifically, greater than 2500 Hz; or at a pulse width less than 100 µs, and more specifically less than 50 µs).

The neuromodulation system further comprises an external control device configured for, in response to a user input, deriving a new modulation program from a pre-existing modulation program, and directing the neuromodulator to deliver modulation energy in accordance with the new modulation program, wherein the pre-existing modulation program is one of a super-threshold modulation program and a sub-threshold modulation program, and the new modulation program is the other of the super-threshold modulation program and the sub-threshold modulation program. In an optional embodiment, the external control device is configured for, in response to another user input, deriving another new modulation program from the pre-existing modulation program, and directing the neuromodulator to deliver modulation energy to the electrode array in accordance with the other new modulation program. The other new modulation program comprises a hybrid modulation program.

In one embodiment, the external control device is configured for deriving the new modulation program from the pre-existing modulation program by computing a pulse amplitude value as a function of the pulse amplitude value of the pre-existing modulation program and including the computed pulse amplitude value in the new modulation program. The function of the pulse amplitude value may be a percentage of the pulse amplitude value. For example, the percentage may be in the range of 30%-70% if the new modulation program is the sub-threshold modulation program, and in the range of 150%-300% if the new modulation program is the super-threshold modulation program, More specifically, the percentage may be in the range of 40%-60% if the new modulation program is the sub-threshold modulation program, and in the range of 175%-250% if the new modulation program is the super-threshold modulation program. As another example, the function of the pulse amplitude value may be one of a difference between the pulse amplitude and a constant and a summation of the pulse amplitude and the constant.

In accordance with an eleventh aspect of the present invention, a method of providing therapy to a patient is provided. The method comprises delivering modulation energy to the patient in accordance with a pre-existing modulation program, thereby providing one of super-threshold therapy (e.g., at a pulse rate less than 1500 Hz, and more specifically, less than 500 Hz; or at a pulse width greater than 100 µs, and more specifically greater than 200 µs) and sub-threshold therapy to the patient (e.g., at a pulse rate greater than 1500 Hz, and more specifically, greater than 2500 Hz; or at a pulse width less than 100 µs, and more specifically less than 50 µs), deriving a new modulation program from the pre-existing modulation program, and delivering modulation energy to the patient in accordance with the new modulation program, thereby providing the other of super-threshold therapy and sub-threshold therapy to the patient. If the patent suffers from chronic pain in a body region, paresthesia may be perceived by the patient in the body region when the modulation energy is delivered to the patient to provide the super-threshold therapy to the patient. An optional method comprises deriving another new modulation program from the pre-existing modulation program, and directing the neuromodulator to deliver modulation energy in accordance with the other new modulation program. The other new modulation program comprises a hybrid modulation program.

In one method, the new modulation program is derived from the pre-existing modulation program by computing a pulse amplitude value as a function of the pulse amplitude value of the pre-existing modulation program and including the computed pulse amplitude value in the new modulation program. The function of the pulse amplitude value may be a percentage of the pulse amplitude value. For example, the percentage may be in the range of 30%-70% if the new modulation program is the sub-threshold modulation program, and in the range of 150%-300% if the new modulation program is the super-threshold modulation program. More specifically, the percentage may be in the range of 40%-60% if the new modulation program is the sub-threshold modulation program, and in the range of 175%-250% if the new modulation program is the super-threshold modulation program. As another example, the function of the pulse amplitude value may be one of a difference between the pulse amplitude and a constant and a summation of the pulse amplitude and the constant.

In accordance with a twelfth aspect of the present inventions, an external control device for programming an implantable neuromodulator coupled to an electrode array implanted within a patient is provided. The external control device comprises a user interface, telemetry circuitry configured for communicating with the neuromodulator, and controller/processor circuitry configured for, in response to input into the user interface, directing the neuromodulator via the telemetry circuitry to deliver super-threshold electrical modulation energy in accordance with a super-threshold modulation parameter set (e.g., defining a pulse rate less than 1500 Hz, and more specifically, less than 500 Hz; or defining a pulse width greater than 100 µs, and more specifically greater than 200 µs), and sub-threshold electrical modulation energy in accordance with a sub-threshold modulation parameter set (e.g., defining a pulse rate greater than 1500 Hz, and more specifically, greater than 2500 Hz; or defining a pulse width less than 100 µs, and more specifically less than 50 µs). The super-threshold modulation parameter set and the sub-threshold modulation parameter set are contained in a hybrid modulation program. The super-threshold modulation parameter set may define a first amplitude value, and the sub-threshold modulation parameter set may define a second amplitude value less than the first amplitude value. For example, the second amplitude value may be in the range of 30%-70% of the first amplitude value, and more specifically, in the range of 40%-60% of the first amplitude value. The external control device may further comprise a housing containing the user interface, the telemetry circuitry, and the controller/processor circuitry.

In one embodiment, the controller/processor circuitry is configured for directing the neuromodulator to simultaneously deliver the super-threshold electrical modulation energy to a first set of the electrodes, and the sub-threshold electrical modulation energy to a second set of electrodes different from the first electrode set. In another embodiment, the controller/processor circuitry is configured for directing the neuromodulator to concurrently deliver the super-threshold electrical modulation energy as a super-threshold electrical pulse train in a first timing channel, and the sub-threshold electrical modulation energy as a sub-threshold electrical pulse train in a second timing channel, such that the pulses of the respective electrical pulse trains do not overlap. In still another embodiment, the controller/processor circuitry is configured for directing the neuromodulator to alternately burst the super-threshold electrical modulation energy on and off, and to alternately burst the sub-threshold electrical modulation energy on and off, such that the bursts of the super-threshold electrical modulation energy and the bursts of the sub-threshold electrical modulation energy are interleaved with each other.

In accordance with a thirteenth aspect of the present inventions, a neuromodulation system comprises an electrode array, an implantable neuromodulator coupled to the electrode array, and an external control device configured for directing the neuromodulator to deliver super-threshold electrical modulation energy in accordance with a super-threshold modulation parameter set (e.g., defining a pulse rate less than 1500 Hz, and more specifically, less than 500 Hz; or defining a pulse width greater than 100 µs, and more specifically greater than 200 µs), and sub-threshold electrical modulation energy in accordance with a sub-threshold modulation parameter set (e.g., defining a pulse rate greater than 1500 Hz, and more specifically, greater than 2500 Hz; or defining a pulse width less than 100 µs, and more specifically less than 50 µs). The super-threshold modulation parameter set and the sub-threshold modulation parameter set are contained in a hybrid modulation program. The super-threshold modulation parameter set may define a first amplitude value, and the sub-threshold modulation parameter set may define a second amplitude value less than the first amplitude value. For example, the second amplitude value may be in the range of 30%-70% of the first amplitude value, and more specifically, in the range of 40%-60% of the first amplitude value.

In one embodiment, the external control device is configured for directing the neuromodulator to simultaneously deliver the super-threshold electrical modulation energy to a first set of the electrodes, and the sub-threshold electrical modulation energy to a second set of electrodes different from the first electrode set. In another embodiment, the external control device is configured for directing the neuromodulator to concurrently deliver the super-threshold electrical modulation energy as a super-threshold electrical pulse train in a first timing channel, and the sub-threshold electrical modulation energy as a sub-threshold electrical pulse train in a second timing channel, such that the pulses of the respective electrical pulse trains do not overlap. In still another embodiment, the external control device is configured for directing the neuromodulator to alternately burst the super-threshold electrical modulation energy on and off, and to alternately burst the sub-threshold electrical modulation energy on and off, such that the bursts of the super-threshold electrical modulation energy and the bursts of the sub-threshold electrical modulation energy are interleaved with each other.

In accordance with a fourteenth aspect of the present invention, a method of providing therapy to a patient is provided. The method comprises delivering super-threshold electrical modulation energy to tissue of the patient in accordance with a super-threshold modulation parameter set, thereby providing super-threshold therapy to the patient (e.g., by defining a pulse rate less than 1500 Hz, and more specifically, less than 500 Hz; or defining a pulse width greater than 100 µs, and more specifically greater than 200 µs), and delivering sub-threshold electrical modulation energy to the tissue of the patient in accordance with a sub-threshold modulation parameter set, thereby providing sub-threshold therapy to the patient (e.g., by defining a pulse rate greater than 1500 Hz, and more specifically, greater than 2500 Hz; or defining a pulse width less than 100 µs, and more specifically less than 50 µs). The super-threshold modulation parameter set and the sub-threshold modulation parameter set are contained in a hybrid modulation program. The super-threshold modulation parameter set may define a first amplitude value, and the sub-threshold modulation parameter set may define a second amplitude value less than the first amplitude value. For example, the second amplitude value may be in the range of 30%-70% of the first amplitude value, and more specifically, in the range of 40%-60% of the first amplitude value. If the patient suffers from chronic pain in a body region, paresthesia may be perceived by the patient in the body region in response to the delivery of the super-threshold modulation energy to the tissue, and paresthesia may not be perceived by the patient in the body region in response to the delivery of the sub-threshold modulation energy to the tissue.

In one method, the super-threshold electrical modulation energy and the sub-threshold electrical modulation energy are simultaneously delivered to a respective first set of electrodes and a second set of electrodes different from the first electrode set. In another method, the super-threshold electrical modulation energy and the sub-threshold electrical modulation energy are concurrently delivered in a respective first timing channel and a second timing channel as electrical pulse trains, such that the pulses of the respective electrical pulse trains do not overlap. In still another method, the super-threshold electrical modulation energy is alternately burst on and off, and the sub-threshold electrical modulation energy is alternately burst on and off, such that the bursts of the super-threshold electrical modulation energy and the bursts of the sub-threshold electrical modulation energy are interleaved with each other.

In accordance with a fifteenth aspect of the present invention, an implantable rechargeable neuromodulator for use with a patient is provided. The neuromodulator comprises a plurality of electrical terminals configured for being coupled to an array of electrodes, and modulation output circuitry coupled to the plurality of electrical terminals. The modulation output circuitry is configured for being selectively operated in a sub-threshold delivery mode for delivering electrical modulation energy to the electrode array to provide sub-threshold therapy to the patient, and a super-threshold delivery mode for delivering electrical modulation energy to the electrode array to provide super-threshold therapy to the patient.

The neuromodulator further comprises a battery configured for storing energy for the modulation output circuitry, monitoring circuitry configured for monitoring a battery capacity level of the battery, and controller/processor circuitry configured for operating the modulation output circuitry in the sub-threshold delivery mode (e.g., by directing the modulation output circuitry to deliver the electrical modulation energy at a pulse rate greater than 1500 Hz, and more specifically, greater than 2500 Hz; or by directing the modulation output circuitry to deliver the electrical modulation energy at a pulse width less than 100 µs, and more specifically less than 50 µs), comparing the battery capacity level to a threshold (e.g., 50% of full battery capacity or 25% of full battery capacity), and switching the modulation output circuitry from the sub-threshold delivery mode to the super-threshold delivery mode (e.g., by directing the modulation output circuitry to deliver the electrical modulation energy at a pulse rate less than 1500 Hz, and more specifically, less than 500 Hz; or by directing the modulation output circuitry to deliver the electrical modulation energy at a pulse width greater than 100 µs, and more specifically greater than 200 µs) if the battery capacity level is less than the threshold.

In one embodiment, the controller/processor circuitry is configured for directing the modulation output circuitry to deliver the electrical modulation energy at a first pulse amplitude value during the sub-threshold delivery mode, and for directing the modulation output circuitry to deliver the electrical modulation energy at a second pulse amplitude value greater than the first pulse amplitude value during the super-threshold delivery mode (e.g., in the range of 150%-300% of the first pulse amplitude value, and more specifically in the range of 175%-250% of the first pulse amplitude value). In another embodiment, the controller/processor circuitry is configured for directing the modulation output circuitry to continue operating in the sub-threshold delivery mode if the battery capacity level is not less than the threshold. The neuromodulator may further comprise a housing containing the telemetry circuitry and the controller/processor circuitry.

In accordance with a sixteenth aspect of the present inventions, a neuromodulation system comprises an electrode array and an implantable rechargeable neuromodulator coupled to the electrode array. The neuromodulator configured for being operated in a sub-threshold delivery mode for delivering electrical modulation energy to the electrode array to provide sub-threshold therapy to the patient (e.g., by delivering the electrical modulation energy at a pulse rate greater than 1500 Hz, and more specifically, greater than 2500 Hz; or by delivering the electrical modulation energy at a pulse width less than 100 µs, and more specifically less than 50 µs), and a super-threshold delivery mode for delivering electrical modulation energy to the electrode array to provide super-threshold therapy to the patient (e.g., by delivering the electrical modulation energy at a pulse rate less than 1500 Hz, and more specifically, less than 500 Hz; or by delivering the electrical modulation energy at a pulse width greater than 100 µs, and more specifically greater than 200 µs).

The neuromodulation system further comprises controller/processor circuitry configured for directing the neuromodulator to operate in the sub-threshold delivery mode, for comparing the battery capacity level to a threshold (e.g., 50% of full battery capacity or 25% of full battery capacity), and for directing the neuromodulator to switch from the sub-threshold delivery mode to the super-threshold delivery mode if the battery capacity level is less than the threshold.

In one embodiment, the controller/processor circuitry is configured for directing the neuromodulator to deliver the electrical modulation energy at a first pulse amplitude value during the sub-threshold delivery mode, and for directing the neuromodulator to deliver the electrical modulation energy at a second pulse amplitude value greater than the first pulse amplitude value during the super-threshold delivery mode (e.g., in the range of 150%-300% of the first pulse amplitude value, and more specifically in the range of 175%-250% of the first pulse amplitude value). In another embodiment, the controller/processor circuitry is configured for directing the neuromodulator to continue operating in the sub-threshold delivery mode if the battery capacity level is not less than the threshold.

In accordance with a seventeenth aspect of the present inventions, a method of providing therapy to a patient using a rechargeable neuromodulator implanted within the patient is provided. The method comprises delivering sub-threshold electrical modulation energy from the neuromodulator to tissue of the patient, thereby providing sub-threshold therapy to the patient (e.g., by delivering the electrical modulation energy at a pulse rate greater than 1500 Hz, and more specifically, greater than 2500 Hz; or by delivering the electrical modulation energy at a pulse width less than 100 µs, and more specifically less than 50 µs), measuring a battery capacity level of the neuromodulator, and comparing the measured battery capacity level to a threshold (e.g., 50% of full battery capacity or 25% of full battery capacity).

The method further comprises delivering super-threshold electrical modulation energy from the neuromodulator to the tissue if the battery capacity level is less than the threshold, thereby providing super-threshold therapy to the patient, and recharging the neuromodulator in response to the delivery of the super-threshold electrical modulation energy from the neuromodulator to the tissue (e.g., by delivering the electrical modulation energy at a pulse rate less than 1500 Hz, and more specifically, less than 500 Hz; or by delivering the electrical modulation energy at a pulse width greater than 100 µs, and more specifically greater than 200 µs). If the patient suffers from chronic pain in a body region, paresthesia may be perceived by the patient in the body region in response to the delivery of the super-threshold modulation energy to the tissue, and paresthesia may not be perceived by the patient in the body region in response to the delivery of the sub-threshold modulation energy to the tissue.

In one method, the sub-threshold electrical modulation energy is delivered at a first pulse amplitude value, and the super-threshold electrical modulation energy is delivered at a second pulse amplitude value greater than the first pulse amplitude value (e.g., in the range of 150%-300% of the first pulse amplitude value, and more specifically in the range of 175%-250% of the first pulse amplitude value).

In accordance with an eighteenth aspect of the present inventions, an external control device for programming an implantable neuromodulator coupled to an electrode array implanted within a patient is provided. The external control device comprises a user interface including a control element, and telemetry circuitry configured for communicating with the neuromodulator. The external control device further comprises controller/processor circuitry configured for directing the neuromodulator via the telemetry circuitry to deliver super-threshold electrical modulation energy to the electrode array in accordance with a super-threshold modulation parameter set, and sub-threshold electrical modulation energy to the electrode array in accordance with a sub-threshold modulation parameter set. The super-threshold modulation parameter set and the sub-threshold modulation parameter set are contained in a hybrid modulation program.

The controller/processor circuitry is further configured for, in response to an event (e.g., a user action of a second control element on the user interface, a signal indicating migration of the implanted electrode array within the patient, a temporal occurrence), directing the neuromodulator via the telemetry circuitry to deliver electrical modulation energy to the electrode array at incrementally increasing amplitude values. In one embodiment, the user interface includes a second control element, and the event is a user actuation of the second control element.

The controller/processor circuitry is further configured for automatically computing, in response to the actuation of the control element, a decreased amplitude value as a function of one of the incrementally increased amplitude values (e.g., the last incrementally increased amplitude value), and directing the neuromodulator via the telemetry circuitry to deliver electrical modulation energy to the electrode array at the computed amplitude value. In one embodiment, the computed function is a percentage (e.g., in the range of 30%-70%, and more specifically, in the range of 40%-60%) of the one incrementally increased amplitude value. In another embodiment, the computed function is a difference between the one incrementally increased amplitude value and a constant.

In one embodiment, the controller/processing circuitry is configured for directing the neuromodulator via the telemetry circuitry to resume delivery of the super-threshold electrical modulation energy to the electrode array in accordance with the super-threshold modulation parameter set. The super-threshold modulation parameter set and the sub-threshold modulation parameter set with the computed amplitude value are contained in a new hybrid modulation program.

In another embodiment, user interface is further configured for receiving user input when the patient perceives paresthesia in response to the delivered sub-threshold electrical modulation energy of the incrementally adjusted amplitude values, in which case, the controller/processing circuitry is configured for selecting the one of the incrementally adjusted amplitude values as the perception threshold based on received user input. In still another embodiment, the neuromodulator is further configured for sensing at least one evoked compound action potential (eCAP) in a population of neurons at a target tissue site in response to the delivered sub-threshold electrical modulation energy of the incrementally adjusted amplitude values, in which case, the controller/processing circuitry is configured for selecting the one of the incrementally adjusted amplitude values as the perception threshold based on the at least one sensed eCAP.

The external control device may further comprise a housing containing the user interface, the telemetry circuitry, and the controller/processor circuitry. If the electrical modulation energy comprises an electrical pulse train, each of the incrementally increased amplitude values and the computed amplitude value may be a pulse amplitude value.

In accordance with a nineteenth aspect of the present inventions, a neuromodulation system is provided. The neuromodulation system comprises an electrode array and an implantable neuromodulator (which may be implantable) coupled to the electrode array. The neuromodulation system further comprises an external control device configured for directing the neuromodulator to deliver super-threshold electrical modulation energy to the electrode array in accordance with a super-threshold modulation parameter set, and sub-threshold electrical modulation energy to the electrode array in accordance with a sub-threshold modulation parameter set. The super-threshold modulation parameter set and the sub-threshold modulation parameter set are contained in a hybrid modulation program.

The external control device is further configured for, in response to an event (e.g., another user input, a signal indicating migration of the implanted electrode array within the patient, or a temporal occurrence, directing the neuromodulator to deliver electrical modulation energy to the electrode array at incrementally increasing amplitude values, automatically computing a decreased amplitude value as a function of one of the incrementally increased amplitude values (e.g., the last incrementally increased amplitude value), and directing the neuromodulator to deliver electrical modulation energy to the electrode array at the computed amplitude value. In one embodiment, the computed function is a percentage (e.g., in the range of 30%-70%, and more specifically, in the range of 40%-60%) of the one incrementally increased amplitude value. In another embodiment, the computed function is a difference between the one incrementally increased amplitude value and a constant. If the electrical modulation energy comprises an electrical pulse train, each of the incrementally increased amplitude values and the computed amplitude value may be a pulse amplitude value.

In one embodiment, the external control device is further configured for receiving user input when the patient perceives paresthesia in response to the delivered sub-threshold electrical modulation energy of the incrementally adjusted amplitude values, and selecting the one of the incrementally adjusted amplitude values as the perception threshold based on received user input. In another embodiment, the neuromodulation system further comprises monitoring circuitry configured for sensing at least one evoked compound action potential (eCAP) in a population of neurons at a target tissue site in response to the delivered sub-threshold electrical modulation energy of the incrementally adjusted amplitude values, in which case, the external control device may be configured for selecting the one of the incrementally adjusted amplitude values as the perception threshold based on the at least one sensed eCAP.

In accordance with a twentieth aspect of the present inventions, a method of providing therapy to a patient is provided. The method comprises delivering super-threshold electrical modulation energy to tissue of the patient in accordance with a super-threshold modulation parameter set, thereby providing super-threshold therapy to the patient, and delivering sub-threshold electrical modulation energy to the tissue of the patient in accordance with a sub-threshold modulation parameter set, thereby providing sub-threshold therapy to the patient. The super-threshold modulation parameter set and the sub-threshold modulation parameter set are contained in a hybrid modulation program. The method further comprises automatically ceasing, in response to an event, delivery of the super-threshold electrical modulation energy to the tissue.

The method further comprises delivering electrical modulation energy to the patient at a series of incrementally increasing amplitude values relative to the programmed amplitude value until the patient perceives paresthesia. If the patient suffers from chronic pain in a body region, the paresthesia may be perceived by the patient in the body region.

The method further comprises automatically computing a decreased amplitude value as a function of one of the series of incrementally increased amplitude values (e.g., the last incrementally increased amplitude value) at which the delivered electrical modulation caused the patient to perceive the paresthesia, and delivering electrical modulation energy to the target tissue site of the patient at the computed amplitude value, thereby providing therapy to the patient without the perception of paresthesia. In one method, the computed function is a percentage (e.g., in the range of 30%-70%, and more specifically, in the range of 40%-60%) of the one incrementally increased amplitude value. In another method, the computed function is a difference between the one incrementally increased amplitude value and a constant.

If the delivered electrical modulation energy comprises an electrical pulse train, each of the programmed amplitude value, incrementally increased amplitude value, and computed amplitude value may be a pulse amplitude value. One method further comprises resuming delivery of the super-threshold electrical modulation energy to the tissue in accordance with the super-threshold modulation parameter set. The super-threshold modulation parameter set and the sub-threshold modulation parameter set with the computed amplitude value are contained in a new hybrid modulation program. Another method further comprises sensing at least one evoked compound action potential (eCAP) in a population of neurons at a target tissue site in response to the delivered sub-threshold electrical pulse train of the incrementally adjusted amplitude values, and selecting the one of the incrementally adjusted amplitude values as the perception threshold based on the sensed eCAP(s). In another method, the electrical modulation energy is delivered from at least one electrode implanted in the patient to the target tissue site at the programmed amplitude value, the electrode (s) migrates relative to the target tissue site when the electrical modulation energy is delivered to the target tissue site at the programmed amplitude value, and the series of amplitude values are generated after the at least one electrode migrates relative to the target tissue site.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 13 is a plan view of a user interface of the CP of FIG. 11 for programming the IPG of FIG. 3 in an electronic trolling programming mode;

DETAILED DESCRIPTION OF THE EMBODIMENTS

The description that follows relates to a spinal cord modulation (SCM) system. However, it is to be understood that the while the invention lends itself well to applications in SCM, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
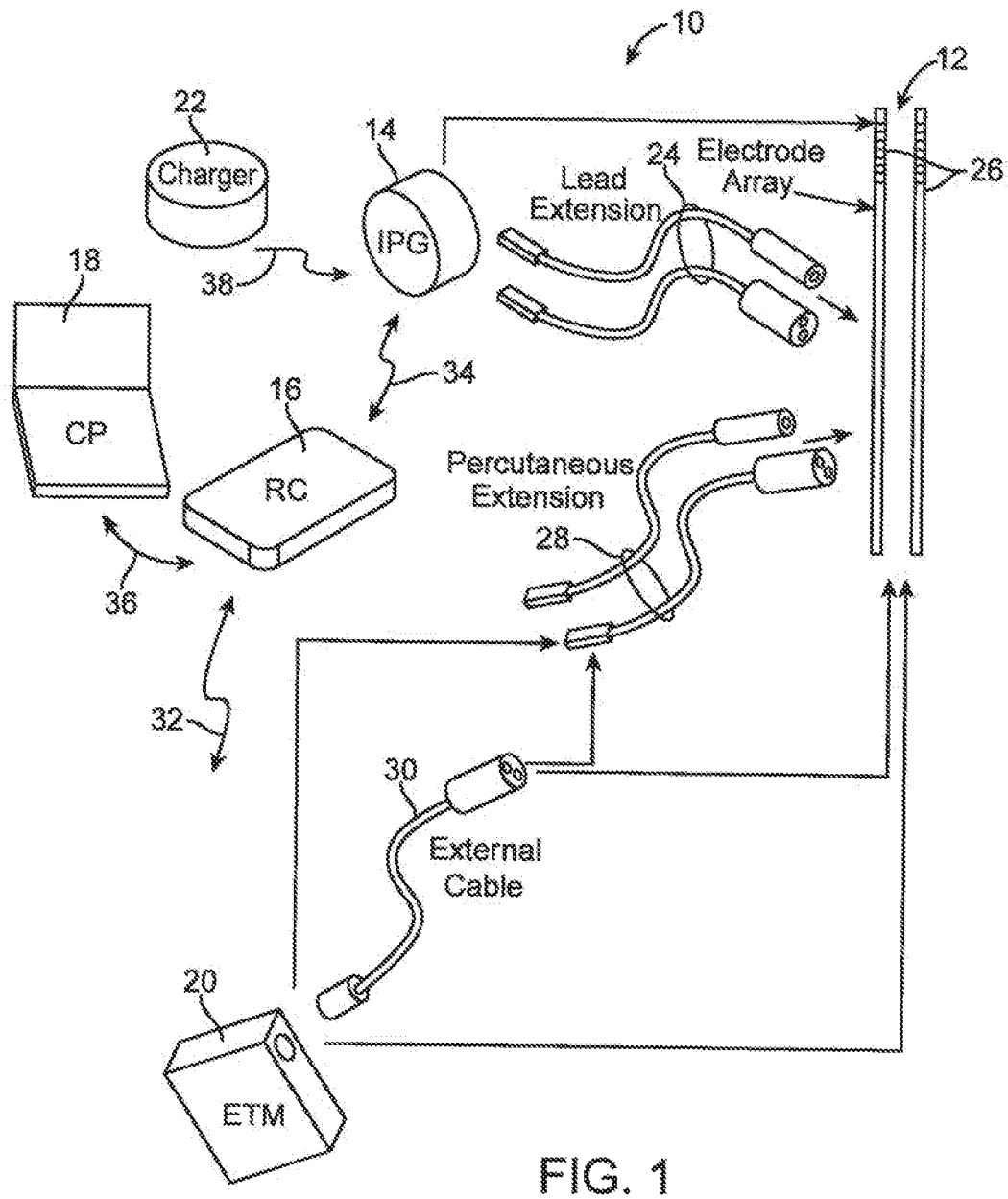
FIG. 1 is a plan view of a Spinal Cord Modulation (SCM) system constructed in accordance with one embodiment of the present inventions.

Turning first to FIG. 1, an exemplary SCM system 10 generally includes a plurality (in this case, two) of implantable neuromodulation leads 12, an implantable pulse generator (IPG) 14, an external remote controller RC 16, a clinician's programmer (CP) 18, an external trial modulator (ETM) 20, and an external charger 22.

The IPG 14 is physically connected via one or more percutaneous lead extensions 24 to the neuromodulation leads 12, which carry a plurality of electrodes 26 arranged in an array. In the illustrated embodiment, the neuromodulation leads 12 are percutaneous leads, and to this end, the electrodes 26 are arranged in-line along the neuromodulation leads 12. The number of neuromodulation leads 12 illustrated is two, although any suitable number of neuromodulation leads 12 can be provided, including only one. Alternatively, a surgical paddle lead in can be used in place of one or more of the percutaneous leads. As will be described in further detail below, the IPG 14 includes pulse generation circuitry that delivers electrical modulation energy in the form of a pulsed electrical waveform (i.e., a temporal series of electrical pulses) to the electrode array 26 in accordance with a set of modulation parameters.

The ETM 20 may also be physically connected via the percutaneous lead extensions 28 and external cable 30 to the neuromodulation leads 12. The ETM 20, which has similar pulse generation circuitry as the IPG 14, also delivers electrical modulation energy in the form of a pulse electrical waveform to the electrode array 26 accordance with a set of modulation parameters. The major difference between the ETM 20 and the IPG 14 is that the ETM 20 is a non-implantable device that is used on a trial basis after the neuromodulation leads 12 have been implanted and prior to implantation of the IPG 14, to test the responsiveness of the modulation that is to be provided. Thus, any functions described herein with respect to the IPG 14 can likewise be performed with respect to the ETM 20. For purposes of brevity, the details of the ETM 20 will not be described herein. Details of exemplary embodiments of ETM are disclosed in U.S. Pat. No. 6,895,280, which is expressly incorporated herein by reference.

The RC 16 may be used to telemetrically control the ETM 20 via a bi-directional RF communications link 32. Once the IPG 14 and neuromodulation leads 12 are implanted, the RC 16 may be used to telemetrically control the IPG 14 via a bi-directional RF communications link 34. Such control allows the IPG 14 to be turned on or off and to be programmed with different modulation parameter sets. The IPG 14 may also be operated to modify the programmed modulation parameters to actively control the characteristics of the electrical modulation energy output by the IPG 14. As will be described in further detail below, the CP 18 provides clinician detailed modulation parameters for programming the IPG 14 and ETM 20 in the operating room and in follow-up sessions.

The CP 18 may perform this function by indirectly communicating with the IPG 14 or ETM 20, through the RC 16, via an IR communications link 36. Alternatively, the CP 18 may directly communicate with the IPG 14 or ETM 20 via an RF communications link (not shown). The clinician detailed modulation parameters provided by the CP 18 are also used to program the RC 16, so that the modulation parameters can be subsequently modified by operation of the RC 16 in a stand-alone mode (i.e., without the assistance of the CP 18).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present. For purposes of brevity, the details of the external charger 22 will not be described herein. Details of exemplary embodiments of the external charger are disclosed in U.S. Pat. No. 6,895,280, which is expressly incorporated herein by reference.

Figure 2:
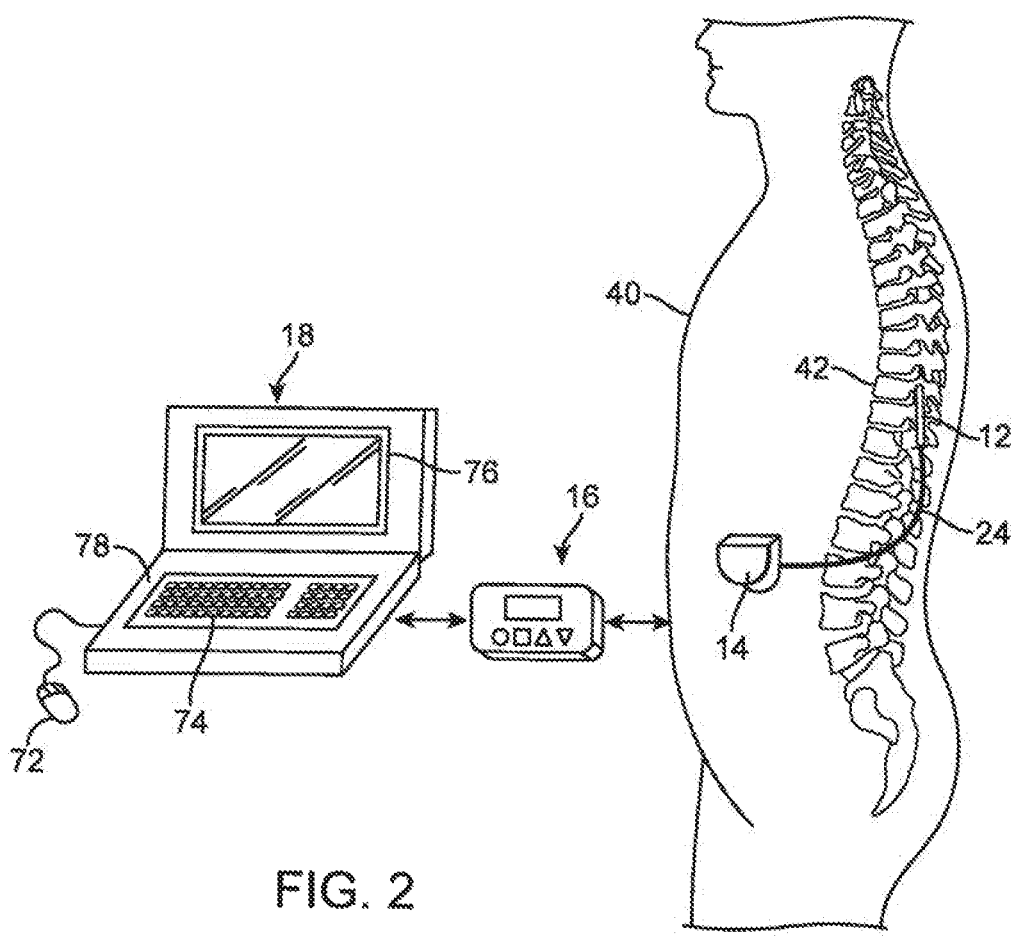
FIG. 2 is a plan view of the SCM system of FIG. 1 in use with a patient.

As shown in FIG. 2, the neuromodulation leads 12 are implanted within the spinal column 42 of a patient 40. The preferred placement of the neuromodulation leads 12 is adjacent, i.e., resting upon, the spinal cord area to be modulated. Due to the lack of space near the location where the neuromodulation leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the neuromodulation leads 12. As there shown, the CP 18 communicates with the IPG 14 via the RC 16.

Figure 3:
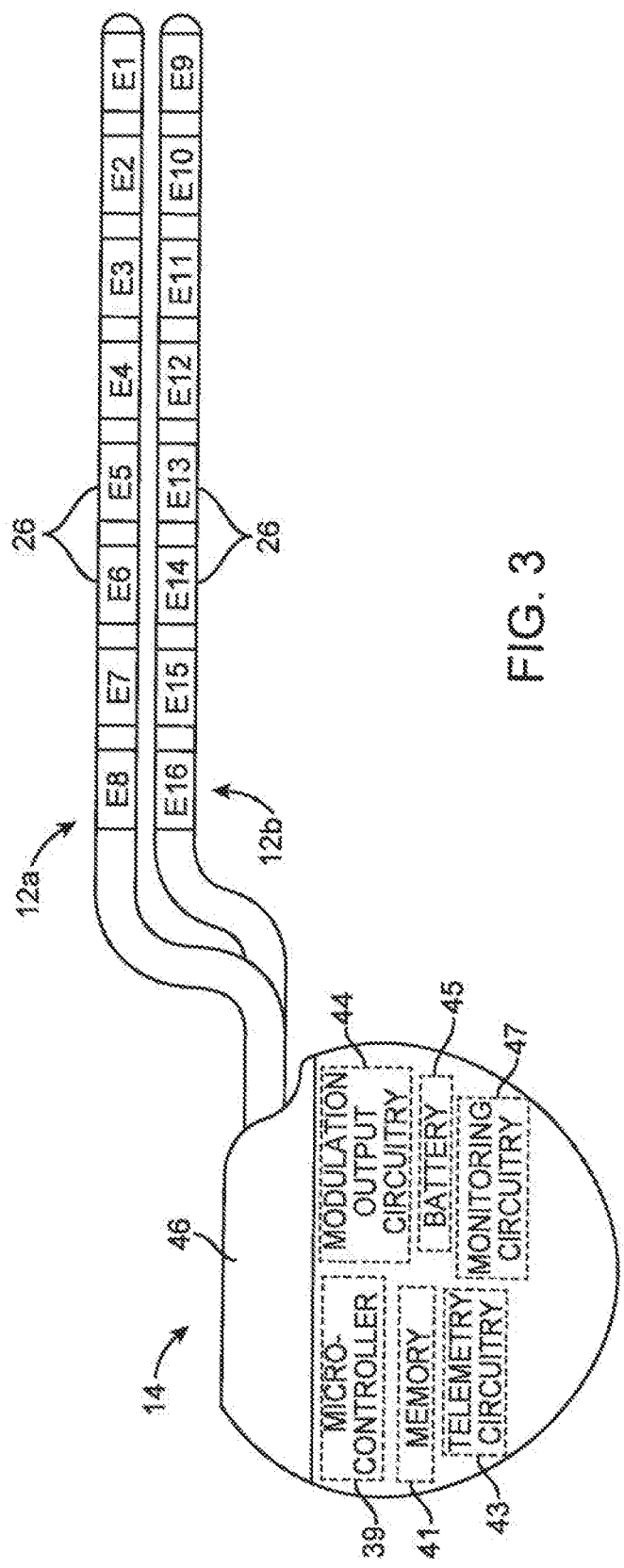
FIG. 3 is a profile view of an implantable pulse generator (IPG) and percutaneous leads used in the SCM system of FIG. 1.

Referring now to FIG. 3, the external features of the neuromodulation leads 12 and the IPG 14 will be briefly described. One of the neuromodulation leads 12a has eight electrodes 26 (labeled E1-E8), and the other neuromodulation lead 12b has eight electrodes 26 (labeled E9-E16). The actual number and shape of leads and electrodes will, of course, vary according to the intended application. The IPG 14 comprises an outer case 44 for housing the electronic and other components (described in further detail below), and a connector 46 to which the proximal ends of the neuromodulation leads 12 mates in a manner that electrically couples the electrodes 26 to the electronics within the outer case 44. The outer case 44 is composed of an electrically conductive, biocompatible material, such as titanium, and forms a hermetically sealed compartment wherein the internal electronics are protected from the body tissue and fluids. In some cases, the outer case 44 may serve as an electrode.

The IPG 14 comprises electronic components, such as a controller/processor (e.g., a microcontroller) 39, memory 41, a battery 43, telemetry circuitry 45, monitoring circuitry 47, modulation output circuitry 49, and other suitable components known to those skilled in the art. The microcontroller 39 executes a suitable program stored in memory 41, for directing and controlling the neuromodulation performed by IPG 14. Telemetry circuitry 45, including an antenna (not shown), is configured for receiving programming data (e.g., the operating program and/or modulation parameters) from the RC 16 and/or CP 18 in an appropriate modulated carrier signal, which the programming data is then stored in the memory (not shown). The telemetry circuitry 45 is also configured for transmitting status data to the RC 16 and/or CP 18 in an appropriate modulated carrier signal. The battery 43, which may be a rechargeable lithium-ion or lithium-ion polymer battery, provides operating power to IPG 14. The monitoring circuitry 47 is configured for monitoring the present capacity level of the battery 43.

The modulation output circuitry 49 provides electrical modulation energy in the form of a pulsed electrical waveform via electrical terminals (not shown) respectively to the electrodes 26 in accordance with a set of modulation parameters programmed into the IPG 14. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the modulation on duration X and modulation off duration Y).

Electrical modulation will occur between two (or more) activated electrodes, one of which may be the IPG case 44. Modulation energy may be transmitted to the tissue in a monopolar or multipolar (e.g., bipolar, tripolar, etc.) fashion. Monopolar modulation occurs when a selected one of the lead electrodes 26 is activated along with the case of the IPG 14, so that modulation energy is transmitted between the selected electrode 26 and case. Bipolar modulation occurs when two of the lead electrodes 26 are activated as anode and cathode, so that modulation energy is transmitted between the selected electrodes 26. For example, electrode E3 on the first lead 12a may be activated as an anode at the same time that electrode E11 on the second lead 12b is activated as a cathode. Tripolar modulation occurs when three of the lead electrodes 26 are activated, two as anodes and the remaining one as a cathode, or two as cathodes and the remaining one as an anode. For example, electrodes E4 and E5 on the first lead 12a may be activated as anodes at the same time that electrode E12 on the second lead 12b is activated as a cathode.

Any of the electrodes E1-E16 and case electrode may be assigned to up to k possible groups or timing "channels." in one embodiment, k may equal four. The timing channel identifies which electrodes are selected to synchronously source or sink current to create an electric field in the tissue to be modulated. Amplitudes and polarities of electrodes on a channel may vary. In particular, the electrodes can be selected to be positive (sourcing current), negative (sinking current), or off (no current) polarity in any of the k timing channels.

Figure 4:
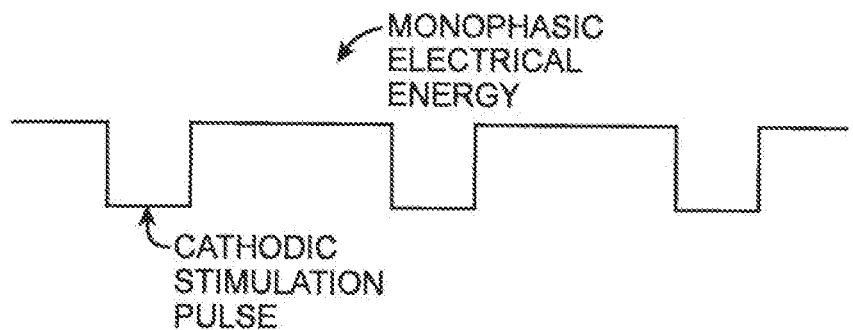
FIG. 4 is a plot of monophasic cathodic electrical modulation energy.

The modulation energy may be delivered between a specified group of electrodes as monophasic electrical energy or multiphasic electrical energy. As illustrated in FIG. 4, monophasic electrical energy takes the form of an electrical pulse train that includes either all negative pulses (cathodic), or alternatively all positive pulses (anodic).

Figure 5A:
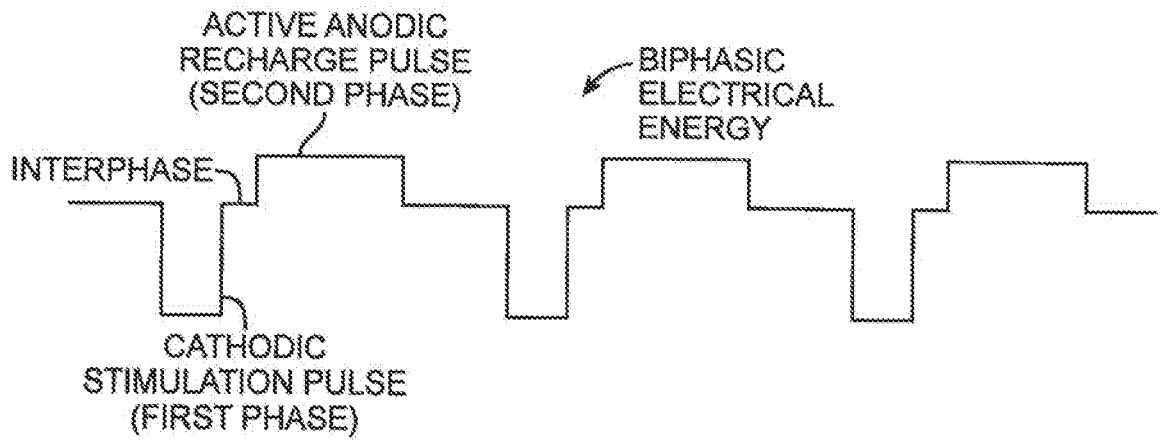
FIG. 5a is a plot of biphasic electrical modulation energy having a cathodic modulation pulse and an active charge recovery pulse.
Figure 5B:
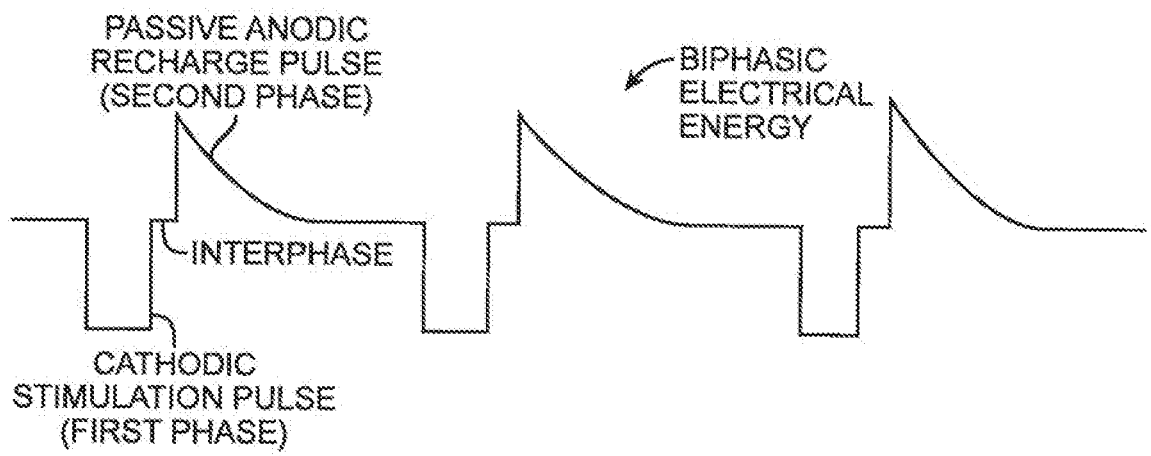
FIG. 5b is a plot of biphasic electrical modulation energy having a cathodic modulation pulse and a passive charge recovery pulse.

Multiphasic electrical energy includes a series of pulses that alternate between positive and negative. For example, as illustrated in FIGS. 5a and 5b, multiphasic electrical energy may include a series of biphasic pulses, with each biphasic pulse including a cathodic (negative) modulation phase and an anodic (positive) charge recovery pulse phase that is generated after the modulation phase to prevent direct current charge transfer through the tissue, thereby avoiding electrode degradation and cell trauma. That is, charge is conveyed through the electrode-tissue interface via current at an electrode during a modulation period (the length of the modulation phase), and then pulled back off the electrode-tissue interface via an oppositely polarized current at the same electrode during a recharge period (the length of the charge recovery phase).

The second phase may be an active charge recovery phase (FIG. 5a), wherein electrical current is actively conveyed through the electrode via current or voltage sources, or the second phase may be a passive charge recovery phase (FIG. 5b), wherein electrical current is passively conveyed through the electrode via redistribution of the charge flowing from coupling capacitances present in the circuit. Using active recharge, as opposed to passive recharge, allows faster recharge, while avoiding the charge imbalance that could otherwise occur. Another electrical pulse parameter in the form of an interphase can define the time period between the pulses of the biphasic pulse (measured in microseconds). Although the modulation and charge recovery phases of the biphasic pulses illustrated in FIGS. 5a and 5b are cathodic and anodic, respectively, it should be appreciated that the modulation and charge recovery pulses of biphasic pulses may be anodic and cathodic, respectively, depending upon the desired therapeutic result.

In the illustrated embodiment, IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other neuromodulators that may be used with the invention include neuromodulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

It should be noted that rather than an IPG, the SCM system 10 may alternatively utilize an implantable receiver-modulator (not shown) connected to the neuromodulation leads 12. In this case, the power source, e.g., a battery, for powering the implanted receiver, as well as control circuitry to command the receiver-modulator, will be contained in an external controller inductively coupled to the receiver-modulator via an electromagnetic link. Data/power signals are transcutaneously coupled from a cable-connected transmission coil placed over the implanted receiver-modulator. The implanted receiver-modulator receives the signal and generates the modulation in accordance with the control signals.

More significant to some of the present inventions, the IPG 14 may be operated in either a super-threshold delivery mode, a sub-threshold delivery mode, and a hybrid delivery mode.

Figure 6A:
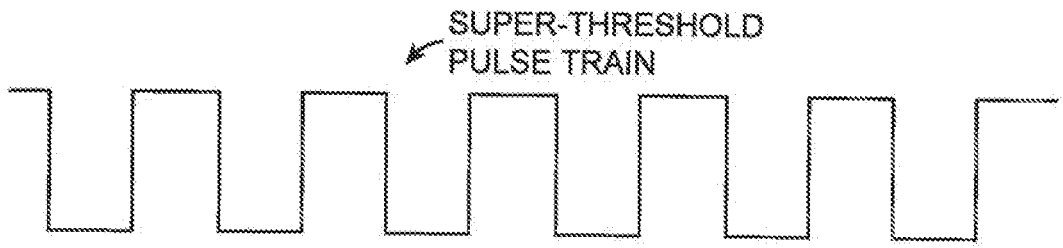
FIG. 6a is a timing diagram of a sub-threshold pulse train delivered by the IPG of FIG. 3 to an electrode.

While in the super-threshold delivery mode, the IPG 14 is configured for delivering electrical modulation energy that provides super-threshold therapy to the patient (in this case, causes the patient to perceive paresthesia). For example, as shown in FIG. 6a, an exemplary super-threshold pulse train may be delivered at a relatively high pulse amplitude (e.g., 5 ma), a relatively low pulse rate (e.g., less than 1500 Hz, preferably less than 500 Hz), and a relatively high pulse width (e.g., greater than 100 µs, preferably greater than 200 µs). Although the super-threshold pulse train is illustrated as a monophasic cathodic pulse train, it should be appreciated that the super-threshold pulse train is preferably biphasic.

Figure 6B:
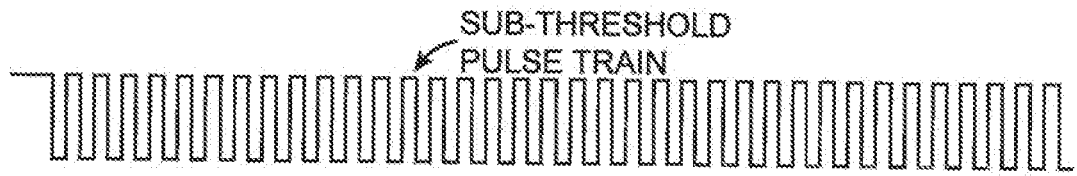
FIG. 6b is a timing diagram of a super-threshold pulse train delivered by the IPG of FIG. 3 to an electrode.

While in the sub-threshold delivery mode, the IPG 14 is configured for delivering electrical modulation energy that provides sub-threshold therapy to the patient (in this case, does not cause the patient to perceive paresthesia). For example, as shown in FIG. 6*b*, an exemplary sub-threshold pulse train may be delivered at a relatively low pulse amplitude (e.g., 2.5 ma), a relatively high pulse rate (e.g., greater than 1500 Hz, preferably greater than 2500 Hz), and a relatively low pulse width (e.g., less than 100 μs, preferably less than 50 μs). Although the sub-threshold pulse train is illustrated as a monophasic cathodic pulse train, it should be appreciated that the sub-threshold pulse train is preferably biphasic with an active charge recovery pulse, as will be described in further detail below.

Figure 6C:
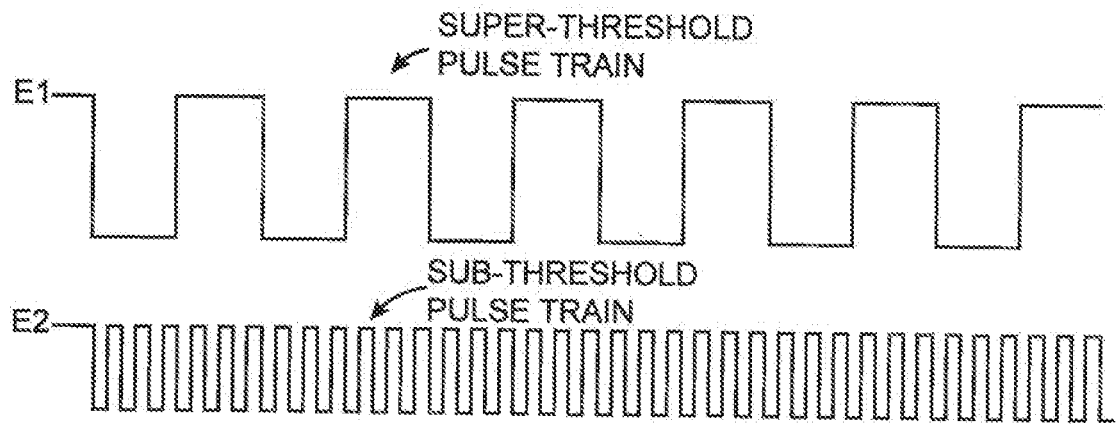
FIG. 6c is a timing diagram of a sub-threshold pulse train and a super-threshold pulse train delivered by the IPG of FIG. 3 to different electrodes.

While in the hybrid delivery mode, the IPG 14 is configured for delivered electrical modulation energy that both provides super-threshold therapy and sub-threshold therapy to the patient. In one embodiment, the super-threshold modulation energy and sub-threshold energy is simultaneously delivered to different sets of electrodes within a single timing channel. Preferably, the different sets of electrodes have no common electrode, so that there is no conflict between the different energies. For example, as shown in FIG. 6*c*, an exemplary super-threshold pulse train may be delivered to electrode E1, while an exemplary sub-threshold pulse train may be delivered to electrode E2. Because the super-threshold pulse train and the sub-threshold pulse train are delivered to different electrodes, the pulses of the respective pulse trains may overlap in time.

Figure 6D:
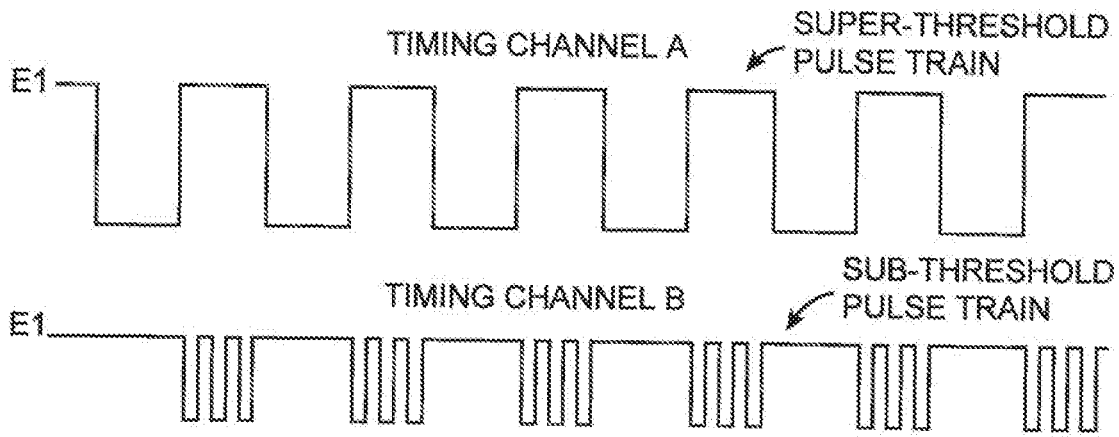
FIG. 6d is a timing diagram of a sub-threshold pulse train and a super-threshold pulse train delivered by the IPG of FIG. 3 during two timing channels to two different electrodes.

In another embodiment, the super-threshold modulation energy and sub-threshold therapy is concurrently delivered to a common set of electrodes within respective timing channels, which are combined into a modulation program. For example, as shown in FIG. 6*d*, an exemplary super-threshold pulse train may be delivered to electrode E1 in timing channel A (coverage area A), and a sub-threshold pulse train may be delivered to electrode E1 in timing channel B (coverage area B), such that the pulses of the respective super-threshold pulse train and sub-threshold pulse train are interleaved with each other without temporal overlap.

Figure 6E:
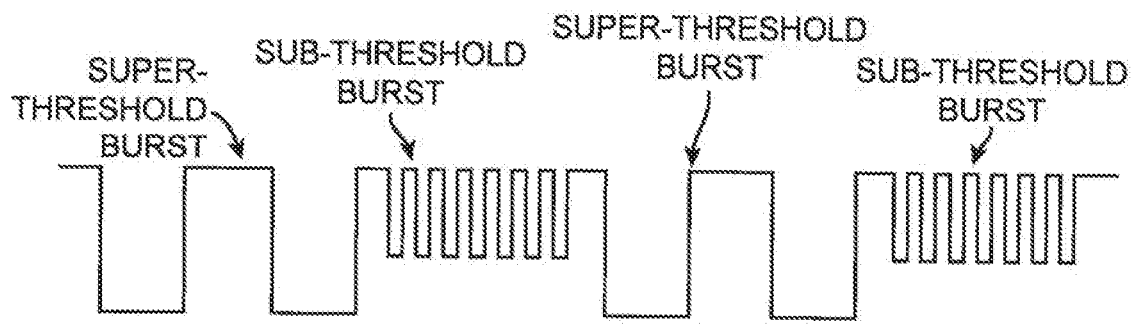
FIG. 6e is a timing diagram of a pulse train with alternating super-threshold and sub-threshold bursts delivered by the IPG of FIG. 3.
Figure 6F:
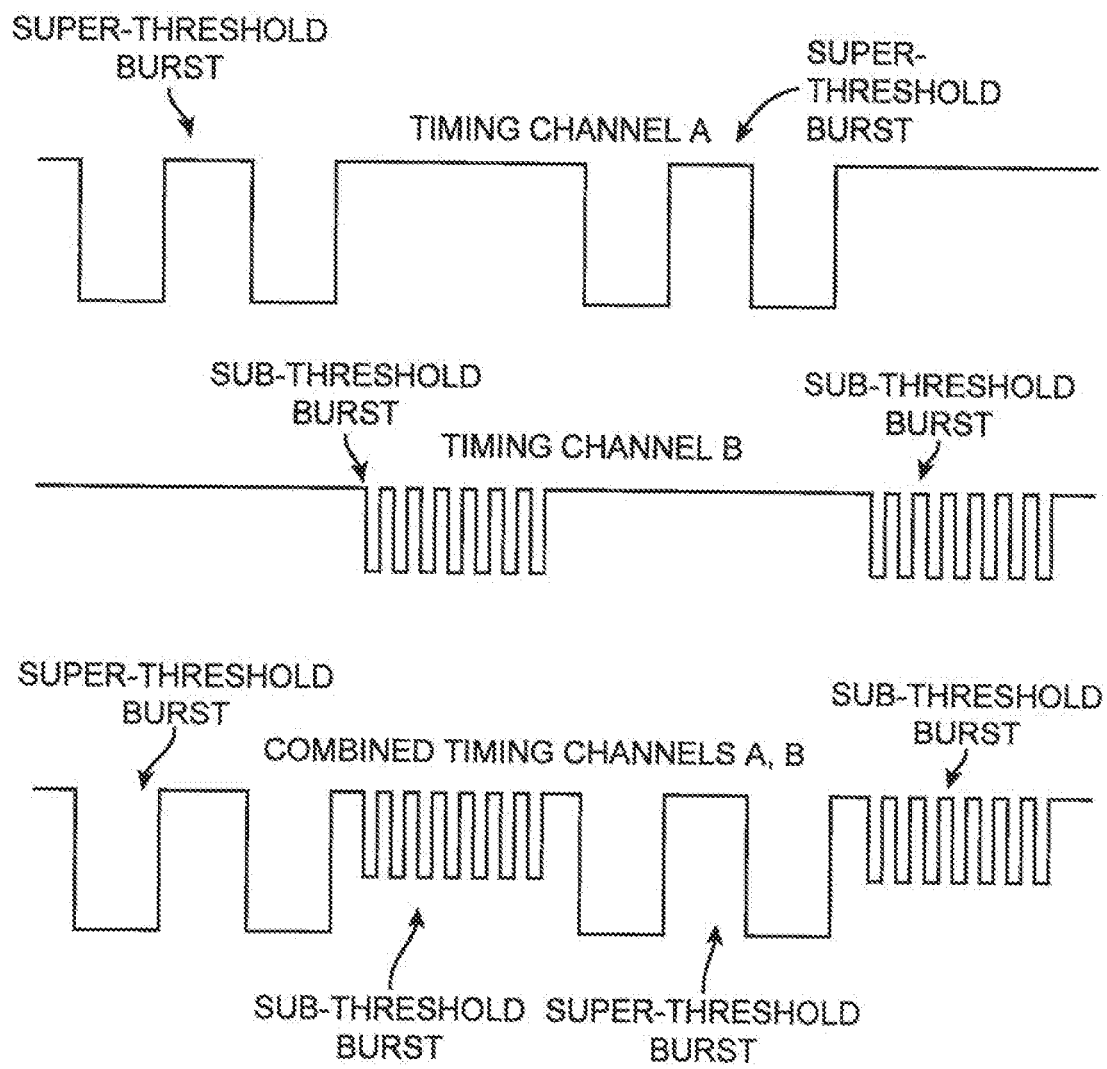
FIG. 6f is a timing diagram of a bursted super-threshold pulse train and a bursted sub-threshold pulse train delivered by the IPG of FIG. 3 during two timing channels.

In still another embodiment, the super-threshold modulation energy and sub-threshold modulation energy can be respectively bursted on and off within a single timing channel or multiple timing channels. For example, as shown in FIG. 6*e*, an exemplary super-threshold pulse train may be repeatedly bursted on and off, with the exemplary sub-threshold pulse train being bursted on when the super-threshold pulse train has been bursted off, and bursted off when the super-threshold pulse train has been bursted on. Thus, the super-threshold pulse train and sub-threshold pulse train will be alternately bursted on and off (i.e., the super-threshold pulse train will be bursted on and then off, the sub-threshold pulse train will be bursted on and then off, the super-threshold pulse train will then be bursted on and then off, the sub-threshold pulse train will be bursted on and then off, and so on). Alternatively, an exemplary super-threshold pulse train may be repeatedly bursted on and off in a first timing channel A (coverage area A), and an exemplary super-threshold pulse train may be repeatedly bursted on and off in a second timing channel B (coverage area B), such that an alternating super-threshold pulse train and sub-threshold pulse train results, as illustrated in FIG. 6*f*. In either event, the bursts of the super-threshold pulse train and the bursts of the subthreshold pulse train will be interleaved with each other.

In any event, the delivery of modulation energy during the hybrid delivery mode exploits the advantages of both the super-threshold therapy and the sub-threshold therapy. For example, because they rely on different mechanisms for pain relief, the delivery of both super-threshold modulation energy and sub-threshold modulation energy to the same general region of the patient may provide therapy that is more efficacious then either can do alone.

Also significant to some of the present inventions, assuming that the IPG 14 is currently operating in the sub-threshold delivery mode, it alerts the patient when the battery capacity level of the IPG 14 is about to be depleted. In particular, the microcontroller 39 is configured for comparing the battery capacity level obtained from the monitoring circuitry 47 to a threshold previously stored within the memory 41, and switching the modulation output circuitry 49 from the sub-threshold delivery mode to the super-threshold (or alternatively, the hybrid) delivery mode if the battery capacity level is less than the threshold, thereby alerting the user to recharge the IPG 14.

As one example, the threshold may be 50% of the full capacity of the battery 43. As another example, the threshold may be 25% of the full capacity of the battery 43. Ultimately, the value of the threshold will be selected to trade-off between providing maximum use from the battery prior to recharge, and allowing the user sufficient time to recharge the IPG 14 before the battery is fully depleted. The microcontroller 39 is configured for automatically switching the modulation output circuitry 49 from the sub-threshold mode to the super-threshold delivery mode (or alternatively the hybrid delivery mode) upon determination that the battery capacity level falls below the threshold. In the case where the battery capacity level does not fall below the threshold, the microcontroller 39 is configured for maintaining the modulation output circuitry 49 within the sub-threshold delivery mode.

It should be appreciated that although the IPG 14 is described as being the device that performs the controlling and processing functions for alerting the user that it needs to be recharged, the controlling and processing functions can be implemented in an external control device (e.g., the RC 16), which can place the IPG 14 between the super-threshold delivery mode, sub-threshold delivery mode, and hybrid delivery mode, as will be described in further detail below.

Figure 7:
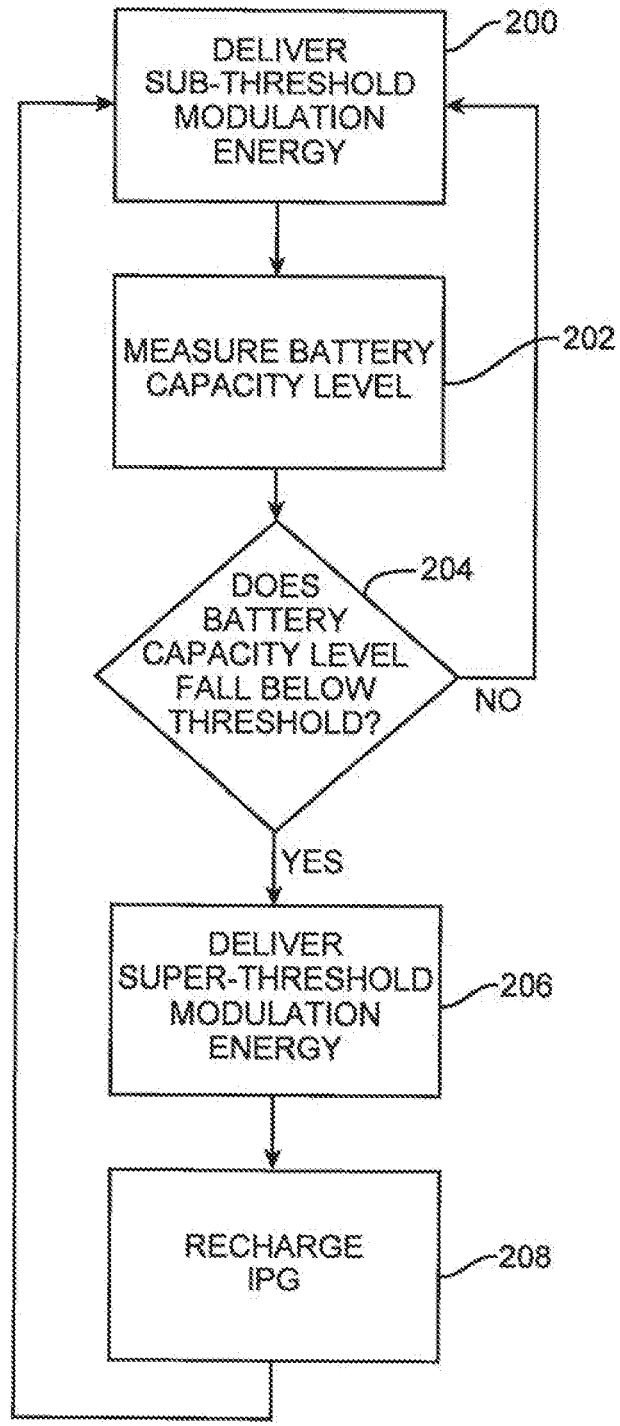
FIG. 7 is a flow diagram illustrating one method performed by the IPG of FIG. 3 to remind a user to recharge the IPG.

Referring now to FIG. 7, one of method of alerting the user to recharge the IPG 14 will be described. First, the IPG 14 delivers sub-threshold electrical modulation energy to the electrode array 26 implanted within spinal cord tissue, thereby providing sub-threshold therapy to the patient (step 200). In the instant case, paresthesia will not be perceived by the patient in the body region corresponding to the pain in response to the delivery of the sub-threshold modulation energy to the electrode array 26. Next, the battery capacity level of the IPG 14 is measured (step 202), and compared to the predetermined threshold (204). If the battery capacity level is not less than the threshold, the IPG 14 continues to deliver the sub-threshold electrical modulation energy to the electrode 26, thereby maintaining sub-threshold therapy to the patient (step 200). If the battery capacity level is less than the threshold, super-threshold electrical modulation energy is delivered from the IPG 14 to the spinal cord tissue, thereby providing super-threshold therapy to the patient (step 206). In the instant case, paresthesia will be perceived by the patient in the body region corresponding to the pain in response to the delivery of the sub-threshold modulation energy to the electrode array 26, thereby alerting the patient that the IPG 14 needs to be recharged. The external charger 22 is then used to conventionally recharge the IPG 14 (step 208).

Figure 8:
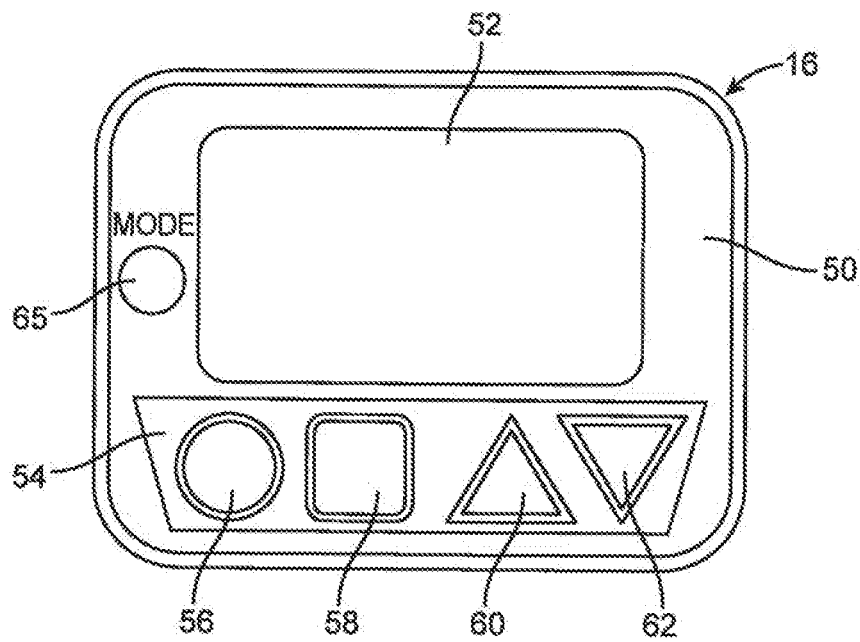
FIG. 8 is front view of a remote control (RC) used in the SCM system of FIG. 1.

Referring now to FIG. 8, one exemplary embodiment of an RC 16 will now be described. As previously discussed, the RC 16 is capable of communicating with the IPG 14, CP 18, or ETS 20. The RC 16 comprises a casing 50, which houses internal componentry (including a printed circuit board (PCB)), and a lighted display screen 52 and button pad 54 carried by the exterior of the casing 50. In the illustrated embodiment, the display screen 52 is a lighted flat panel display screen, and the button pad 54 comprises a membrane switch with metal domes positioned over a flex circuit, and a keypad connector connected directly to a PCB. In an optional embodiment, the display screen 52 has touchscreen capabilities. The button pad 54 includes a multitude of buttons 56, 58, 60, and 62, which allow the IPG 14 to be turned ON and OFF, provide for the adjustment or setting of modulation parameters within the IPG 14, and provide for selection between screens.

In the illustrated embodiment, the button 56 serves as an ON/OFF button that can be actuated to turn the IPG 14 ON and OFF. The button 58 serves as a select button that can be actuated to switch the RC 16 between screen displays and/or parameters. The buttons 60 and 62 serve as up/down buttons that can be actuated to increment or decrement any of modulation parameters of the pulsed electrical train generated by the IPG 14, including pulse amplitude, pulse width, and pulse rate. For example, the selection button 58 can be actuated to place the RC 16 in a "Pulse Amplitude Adjustment Mode," during which the pulse amplitude can be adjusted via the up/down buttons 60, 62, a "Pulse width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons can be provided for each modulation parameter. Rather than using up/down buttons, any other type of actuator, such as a dial, slider bar, or keypad, can be used to increment or decrement the modulation parameters.

Figure 9:
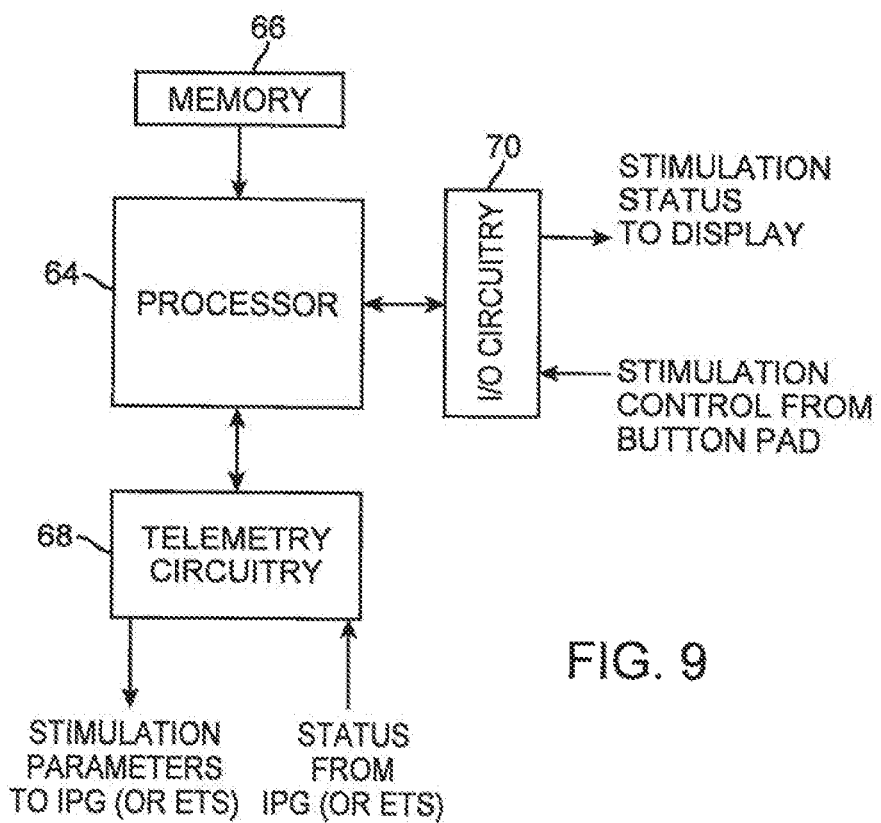
FIG. 9 is a block diagram of the internal components of the RC of FIG. 8.

Referring to FIG. 9, the internal components of an exemplary RC 16 will now be described. The RC 16 generally includes a controller/processor 64 (e.g., a microcontroller), memory 66 that stores an operating program for execution by the controller/processor 64, as well as modulation parameter sets; input/output circuitry, and in particular, telemetry circuitry 68 for outputting modulation parameters to the IPG 14 or otherwise directing the IPG 14 to deliver modulation energy in accordance with the modulation parameters, and receiving status information from the IPG 14; and input/output circuitry 70 for receiving modulation control signals from the button pad 54 or other control elements and transmitting status information to the display screen 52 (shown in FIG. 8). Further details of the functionality and internal componentry of the RC 16 are disclosed in U.S. Pat. No. 6,895,280, which has previously been incorporated herein by reference.

More significant to the present inventions, to allow the user to easily and quickly select between the different modes, the RC 16 comprises a modulation selection control element 65, which in the illustrated embodiment, takes the form of a button. The modulation selection control element 65 may be repeatedly actuated to toggle the IPG 14 between the super-threshold, sub-threshold, and hybrid delivery modes. For example, the modulation selection control element 65 may be actuated once to switch the IPG 14 from the super-threshold delivery mode to the sub-threshold delivery mode, actuated once again to switch the IPG 14 from the sub-threshold delivery mode to the hybrid delivery mode, actuated once again to switch the IPG 14 from the hybrid delivery mode back to the super-threshold delivery mode, and so forth. Of course, the order of the mode selection can be changed. For example, the modulation selection control element 65 may be actuated once to switch the IPG 14 from the sub-threshold delivery mode to the super-threshold delivery mode, actuated once again to switch the IPG 14 from the super-threshold delivery mode to the hybrid delivery mode, actuated once again to switch the IPG 14 from the hybrid delivery mode back to the sub-threshold delivery mode, and so forth. In any event, each of the modulation delivery modes can be selected by toggling the modulation selection control element 65.

The different modulation programs that are utilized by the IPG 14 when operating in the different delivery modes may be generated in any one of a variety of manners. For example, if the IPG 14 and/or RC 16 are pre-programmed via the CP 18 (described in further detail below) with a pre-existing super-threshold modulation program, a pre-existing sub-threshold modulation program, and a pre-existing hybrid modulation program, the RC 16 simply selects one of these pre-existing modulation programs in response to the actuation of the modulation selection control element 65. In this case, the RC 16 may identify which of the pre-existing modulation programs correspond to the respective super-threshold, sub-threshold, and hybrid programs based on the characteristics of the modulation parameter set or sets defined by these programs, or the user may identify and label each pre-existing modulation program as either a super-threshold, sub-threshold, or hybrid modulation program when generating these modulation programs with the CP 18.

In the case where a pre-existing modulation program does not exist for one or more of the super-threshold, sub-threshold, and hybrid delivery modes, the RC 16, in response to actuation of either the modulation selection control element 65 or a different control element, may generate a new modulation program from one or more of the pre-existing modulation programs.

In the case where only a super-threshold modulation program exists, the RC 16 may quickly derive a sub-threshold modulation program from the pre-existing super-threshold modulation program. In particular, the RC 16 may substitute one or more of the electrical pulse parameter values (pulse amplitude, pulse rate, pulse width) of the pre-existing super-threshold modulation program with electrical pulse parameter values that are consistent with sub-threshold therapy. For example, the RC 16 may compute a new pulse amplitude value as function of the super-threshold pulse amplitude value. The computed function may be, e.g., a percentage (preferably in the range of 30%-70%, and more preferably in the range of 40%-60%) of the super-threshold pulse amplitude value, or a difference between the super-threshold pulse amplitude value and a constant (e.g., 1 mA). The RC 16 may select a relatively high pulse rate value (e.g., greater than 1500 Hz) as new pulse rate value and/or a relatively low pulse width value (e.g., less than 100 µs) for the new sub-threshold modulation program. The RC 16 may also compute a new fractionalized electrode combination from the fractionalized electrode combination defined in the pre-existing super-threshold modulation program (e.g., by transforming from anodic to cathodic modulation, or vice versa, or transforming from monopolar modulation to multipolar modulation, or vice versa). However, the locus of the electrical field that would result from delivering modulation energy in accordance with the pre-existing super-threshold program should be maintained in the new sub-threshold modulation program. As described in further detail below with respect to the CP 18, this can be accomplished with the use of virtual target poles.

In the case where only a sub-threshold modulation program exists, the RC 16 may quickly derive a super-threshold modulation program from the pre-existing sub-threshold modulation program. In particular, the RC 16 may substitute one or more of the electrical pulse parameters values (pulse amplitude, pulse rate, pulse width) of the pre-existing sub-threshold modulation program with electrical pulse parameter values that are consistent with super-threshold therapy. For example, the RC 16 may compute a new pulse amplitude value as function of the super-threshold pulse amplitude value. The computed function may be, e.g., a percentage (preferably in the range of 150% to 300%, and more preferably in the range of 175%-250%) of the sub-threshold pulse amplitude value, or a summation of the sub-threshold pulse amplitude value and a constant (e.g., 1 mA). The RC 16 may select a relatively low pulse rate value (e.g., less than 1500 Hz) as new pulse rate value and/or a relatively high pulse width value (e.g., greater than 100 µs) for the new sub-threshold modulation program. The RC 16 may also compute a new fractionalized electrode combination from the fractionalized electrode combination defined in the pre-existing sub-threshold modulation program (e.g., by transforming from anodic to cathodic modulation, or vice versa, or transforming from monopolar modulation to multipolar modulation, or vice versa). However, the locus of the electrical field that would result from delivering modulation energy in accordance with the pre-existing sub-threshold program should be maintained in the new super-threshold modulation program. As described in further detail below with respect to the CP 18, this can be accomplished with the use of virtual target poles.

In the case where only a hybrid modulation program exists, the RC 16 can simply copy the modulation parameters of super-threshold component of the hybrid modulation program to a new super-threshold modulation program (to the extent that one is needed), and/or copy the modulation parameters of the sub-threshold component of the hybrid modulation program to a new sub-threshold modulation program (to the extent that one is needed). In the case where both the super-threshold program and the sub-threshold program exist, the RC 16 can combine the modulation parameters of these programs together to define a new hybrid modulation program (to the extent that one is needed). Or, if only one of the super-threshold modulation program and a sub-threshold modulation program exists, it and a modulation program derived from the other of the super-threshold modulation program and sub-threshold modulation program, and combined into the new hybrid modulation program.

Also significant to some of the present inventions, in response to a particular event, the RC 16, assuming that the IPG 14 is currently programmed to deliver sub-threshold therapy to the patient (e.g., a sub-threshold modulation program or a hybrid modulation program), initiates calibration of the sub-threshold therapy that may have fallen outside of the therapeutic range due to the migration of the modulation lead(s) 12 relative to a target tissue site in the patient. Migration of the modulation lead(s) 12 may alter the coupling efficiency between the modulation lead(s) 12 and the target tissue site. A decreased coupling efficiency may cause the sub-threshold therapy to fall below the therapeutic range and result in ineffective therapy, whereas an increased coupling efficiency may cause the sub-threshold therapy to rise above the therapeutic range and result in the perception of paresthesia or otherwise inefficient energy consumption. The particular event that triggers calibration of the sub-threshold therapy may be a user actuation of a control element located on the RC 16 (e.g., one of the buttons on the button pad 54 or a dedicated button), a sensor signal indicating that one or more of the neuromodulation leads 12 has migrated relative to a target site in the patient, or a temporal occurrence, such as an elapsed time from a previous calibration procedure, a time of day, day of the week, etc.

Once the sub-threshold calibration is initiated, the RC 16 is configured for directing the IPG 14 to deliver the modulation energy to the electrodes 26 at incrementally increasing amplitude values (e.g., at a 0.1 mA step size). The RC 16 may be configured for automatically incrementally increasing the amplitude of the electrical pulse train delivered by the IPG 14 without further user intervention or may be configured for incrementally increasing the amplitude of the electrical pulse train delivered by the IPG 14 each time the user actuates a control element, such as the up button 60. Preferably, the other modulation parameters, such as the electrode combination, pulse rate, and pulse width are not altered during the incremental increase of the amplitude. Thus, the only modulation parameter of the sub-threshold modulation program that is altered is the pulse amplitude.

The RC 16 is configured for prompting the user via the display 52 or speaker (not shown) to actuate a control element, such as a specified button on the button pad 54 or another dedicated button (not shown), once paresthesia is perceived by the patient. In response to this user input, the RC 16 is configured for automatically computing a decreased amplitude value as a function of the last incrementally increased amplitude value that caused the patient to perceive paresthesia, and modifying the sub-threshold modulation program stored in the IPG 14, such that the modulation energy is delivered to the electrodes 26 in accordance with this modified modulation program at this computed amplitude value. Alternatively, rather than relying on user input, the RC 16 may be configured for automatically computing the decreased amplitude value in response to a sensed physiological parameter indicative of super-threshold stimulation of the neural tissue (e.g., evoked compound action potentials (eCAPs) sensed by the IPG 14 at one or more electrodes 26 as a result of the delivery of the modulation energy). Further details on eCAPs are disclosed in U.S. Provisional Patent Application Ser. No. 61/768,295, entitled "Neurostimulation system and method for automatically adjusting stimulation and reducing energy requirements using evoked action potential," which is expressly incorporated herein by reference.

In any event, the function of the last incrementally increased amplitude value is designed to ensure that the modulation energy subsequently delivered to the patient at the computed amplitude value falls within the sub-threshold therapy range. For example, the computed function may be a percentage (preferably in the range of 30%-70%, and more preferably in the range of 40%-60%) of the last incrementally increased amplitude value. As another example, the computed function may a difference between the last incrementally increased amplitude value and a constant (e.g., 1 mA).

It should be appreciated that if calibration is initiated when the IPG 14 is being operated in the hybrid delivery mode such that the delivered electrical modulation energy comprises both super-threshold electrical pulse train(s) and sub-threshold electrical pulse train(s), the super-threshold electrical pulse train (or trains) is automatically suspended temporarily such that calibration is conducted only based on the remaining sub-threshold electrical pulse train. For example, referring back to the hybrid delivery mode illustrated in FIG. 6c, when calibration is initiated, delivery of the super-threshold pulse train to electrode E1 is stopped, and the sub-threshold pulse train is delivered to electrode E2 at incrementally increasing amplitude values until the perception threshold is determined and a decreased amplitude is computed based on the perception threshold as the sub-threshold amplitude value, as described above.

In another example, referring back to FIG. 6d, when calibration is initiated, delivery of the super-threshold pulse train to electrode E1 is stopped, and the calibration process is continued using the sub-threshold pulse train delivered to electrode E1. Referring to FIG. 6e, when calibration is initiated, the illustrated super-threshold bursts are stopped, such that the calibration process is continued only based on the sub-threshold bursts of the hybrid modulation program. Referring to FIG. 6f, when calibration is initiated, the super-threshold pulse train of timing channel A is stopped, such that the calibration process is continued only based on the sub-threshold pulse train of timing channel B.

Once the calibration process is completed and the sub-threshold amplitude is computed, as discussed above, the hybrid delivery mode is resumed such that electrical energy is delivered in accordance to both the original super-threshold pulse train and the sub-threshold pulse train having the calibrated sub-threshold amplitude.

It should also be appreciated that, in a preferred embodiment, the RC 16 may be configured for storing the computed sub-threshold amplitude resulting from each calibration process. This is significant because it provides the user important metrics regarding the sub-threshold therapy that may allow the user to modify modulation parameters of the sub-threshold pulse train more intelligently at a later programming session.

Figure 10:
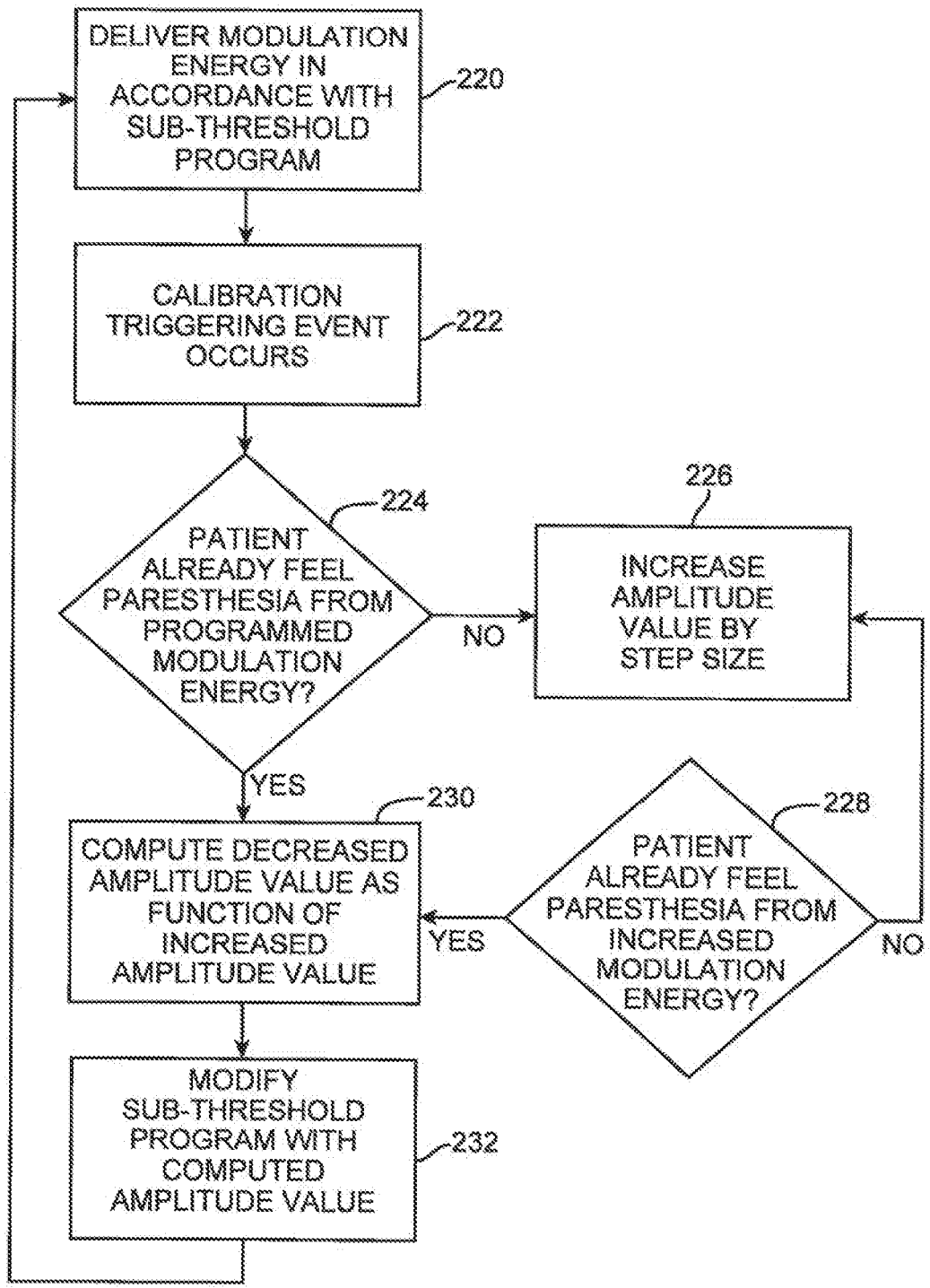
FIG. 10 is a flow diagram illustrating one method performed by the RC of FIG. 8 to calibrate the sub-threshold therapy provided by the IPG of FIG. 3.

Referring now to FIG. 10, one method of using the RC 16 to calibrate the sub-threshold therapy will now be described. First, the RC 16 is operated to direct the IPG 14 to deliver electrical modulation energy to a target tissue site of the patient in accordance with a sub-threshold modulation program stored within the IPG 14, thereby providing therapy to the patient without the perception of paresthesia (step 220). Next, a calibration triggering event occurs (step 222). Such triggering input can be a user input, a detected migration of one or more of the modulation leads relative to the target tissue site, or a temporal occurrence. Next, it is determined whether the patient perceives paresthesia in the region of pain as a result of the delivery of the modulation energy in accordance with the unmodified sub-threshold modulation program (step 204).

If the patient does not currently perceive paresthesia in the region of pain at step 204, the RC 16 increases the programmed amplitude value by a step size, and directs the IPG 14 to deliver electrical modulation energy to the patient at the increased amplitude value (step 226). Next, it is determined whether the patient perceives paresthesia in the region of pain as a result of the delivery of the modulation energy at the increased amplitude value (step 228). If the patient does not perceive paresthesia in the region of pain at step 228, the RC 16 returns to step 226 to again increase the programmed amplitude value by a step size, and direct the IPG 14 to deliver electrical modulation energy to the patient at the increased amplitude value.

If the patient perceived paresthesia in the region of pain at step 224 or step 228, the RC 16 computes a decreased amplitude value as a function of the last incrementally increased amplitude value at which the delivered electrical modulation caused the patient to perceive the paresthesia in the region of pain (step 230). Such computation can be performed in response to a user input, or alternatively, sensing a physiological parameter indicating that the patient is perceiving paresthesia. As described above, such function can be, e.g., a percentage of the last incrementally increased amplitude value or a difference between the last incrementally increased amplitude value and a constant. The RC 16 then modifies the sub-threshold modulation program with the computed amplitude value (step 232), and returns to step 220 to direct the IPG 14 to deliver electrical modulation energy to a target tissue site of the patient in accordance with a modified sub-threshold modulation program, thereby providing therapy to the patient without the perception of paresthesia.

Thus, it can be appreciated that the sub-threshold calibration technique ensures that any intended sub-threshold therapy remains within an efficacious and energy efficient therapeutic window that may otherwise fall outside of this window due to environmental changes, such as lead migration or even posture changes or patient activity. Although the sub-threshold calibration technique has been described with respect to sub-threshold therapy designed to treat chronic pain, it should be appreciated that this calibration technique can be utilized to calibrate any sub-threshold therapy provided to treat a patient with any disorder where the perception of paresthesia may be indicative of efficacious treatment of the disorder. Furthermore, although the sub-threshold calibration technique has been described as being performed in the RC 16, or should be appreciated that this technique could be performed in the CP 18, or even the IPG 14. If performed by the IPG 14, any user input necessary to implement the sub-threshold calibration technique can be communicated from the RC 16 to the IPG 14 via the telemetry circuitry 68. In the case, where no user input is necessary, e.g., if super-threshold stimulation is detected at one or more of the electrodes 26 in lieu of patient feedback of paresthesia, the IPG 14 may implement the sub-threshold calibration technique without any communication with the RC 16.

As briefly discussed above, the CP 18 greatly simplifies the programming of multiple electrode configurations, allowing the user (e.g., the physician or clinician) to readily determine the desired modulation parameters to be programmed into the IPG 14, as well as the RC 16. Thus, modification of the modulation parameters in the programmable memory of the IPG 14 after implantation is performed by a user using the CP 18, which can directly communicate with the IPG 14 or indirectly communicate with the IPG 14 via the RC 16. That is, the CP 18 can be used by the user to modify operating parameters of the electrode array 26 near the spinal cord.

As shown in FIG. 2, the overall appearance of the CP 18 is that of a laptop personal computer (PC), and in fact, may be implemented using a PC that has been appropriately configured to include a directional-programming device and programmed to perform the functions described herein. Alternatively, the CP 18 may take the form of a mini-computer, personal digital assistant (PDA), etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum modulation parameters to be determined based on patient feedback and for subsequently programming the IPG 14 with the optimum modulation parameter.

To allow the user to perform these functions, the CP 18 includes a user input device (e.g., a mouse 72 and a keyboard 74), and a programming display screen 76 housed in a case 78. It is to be understood that in addition to, or in lieu of, the mouse 72, other directional programming devices may be used, such as a trackball, touchpad, joystick, or directional keys included as part of the keys associated with the keyboard 74.

In the illustrated embodiment described below, the display screen 76 takes the form of a conventional screen, in which case, a virtual pointing device, such as a cursor controlled by a mouse, joy stick, trackball, etc., can be used to manipulate graphical objects on the display screen 76. In alternative embodiments, the display screen 76 takes the form of a digitizer touch screen, which may either passive or active. If passive, the display screen 76 includes detection circuitry (not shown) that recognizes pressure or a change in an electrical current when a passive device, such as a finger or non-electronic stylus, contacts the screen. If active, the display screen 76 includes detection circuitry that recognizes a signal transmitted by an electronic pen or stylus. In either case, detection circuitry is capable of detecting when a physical pointing device (e.g., a finger, a non-electronic stylus, or an electronic stylus) is in close proximity to the screen, whether it be making physical contact between the pointing device and the screen or bringing the pointing device in proximity to the screen within a predetermined distance, as well as detecting the location of the screen in which the physical pointing device is in close proximity. When the pointing device touches or otherwise is in close proximity to the screen, the graphical object on the screen adjacent to the touch point is "locked" for manipulation, and when the pointing device is moved away from the screen the previously locked object is unlocked. Further details discussing the use of a digitizer screen for programming are set forth in U.S. Provisional Patent Application Ser. No. 61/561,760, entitled "Technique for Linking Electrodes Together during Programming of Neurostimulation System," which is expressly incorporated herein by reference.

Figure 11:
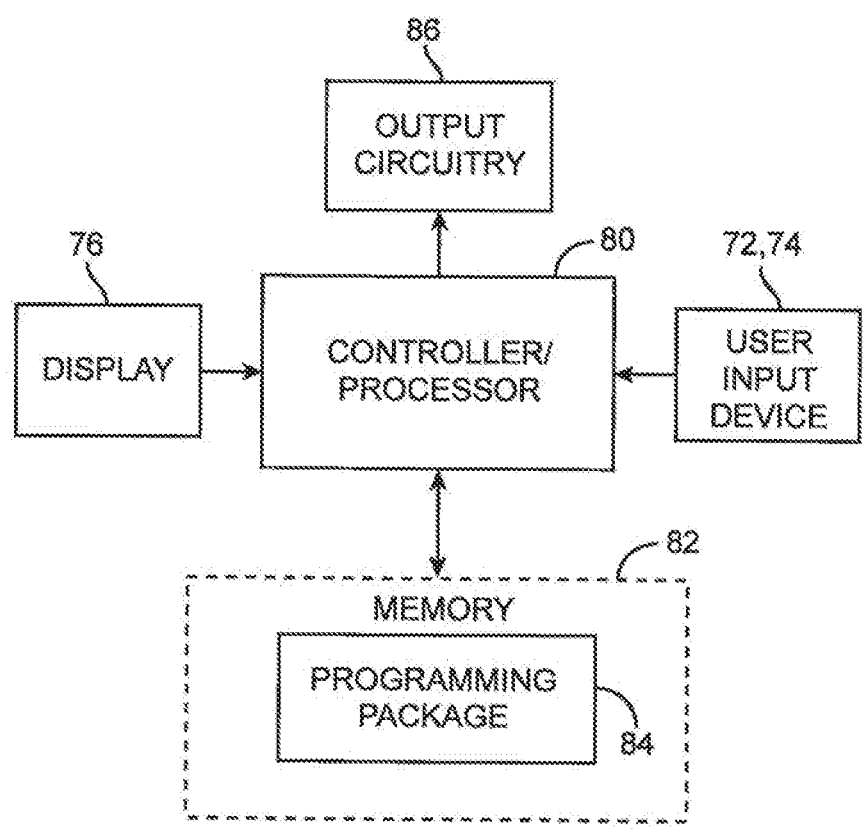
FIG. 11 is a block diagram of the internal components of a clinician's programmer (CP) used in the SCM system of FIG. 1.

As shown in FIG. 11, the CP 18 includes a controller/processor 80 (e.g., a central processor unit (CPU)) and memory 82 that stores a modulation programming package 84, which can be executed by the controller/processor 80 to allow the user to program the IPG 14, and RC 16. The CP 18 further includes an output circuitry 86 for downloading modulation parameters to the IPG 14 and RC 16 and for uploading modulation parameters already stored in the memory 66 of the RC 16 or memory of the IPG 14. In addition, the CP 18 further includes a user input device 88 (such as the mouse 72 or keyboard 74) to provide user commands. Notably, while the controller/processor 80 is shown in FIG. 11 as a single device, the processing functions and controlling functions can be performed by a separate controller and processor. Thus, it can be appreciated that the controlling functions described below as being performed by the CP 18 can be performed by a controller, and the processing functions described below as being performed by the CP 18 can be performed by the processor.

Execution of the programming package 84 by the controller/processor 80 provides a multitude of display screens (not shown) that can be navigated through via use of the mouse 72. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical modulation energy output by the neuromodulation leads 12, and select and program the IPG 14 with modulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steeling Navigator," and U.S. patent application Ser. No. 12/614,942, entitled "System and Method for Determining Appropriate Steering Tables for Distributing Modulation energy Among Multiple Neuromodulation Electrodes," which are expressly incorporated herein by reference. Execution of the programming package 84 provides a user interface that conveniently allows a user to program the IPG 14.

Figure 12:
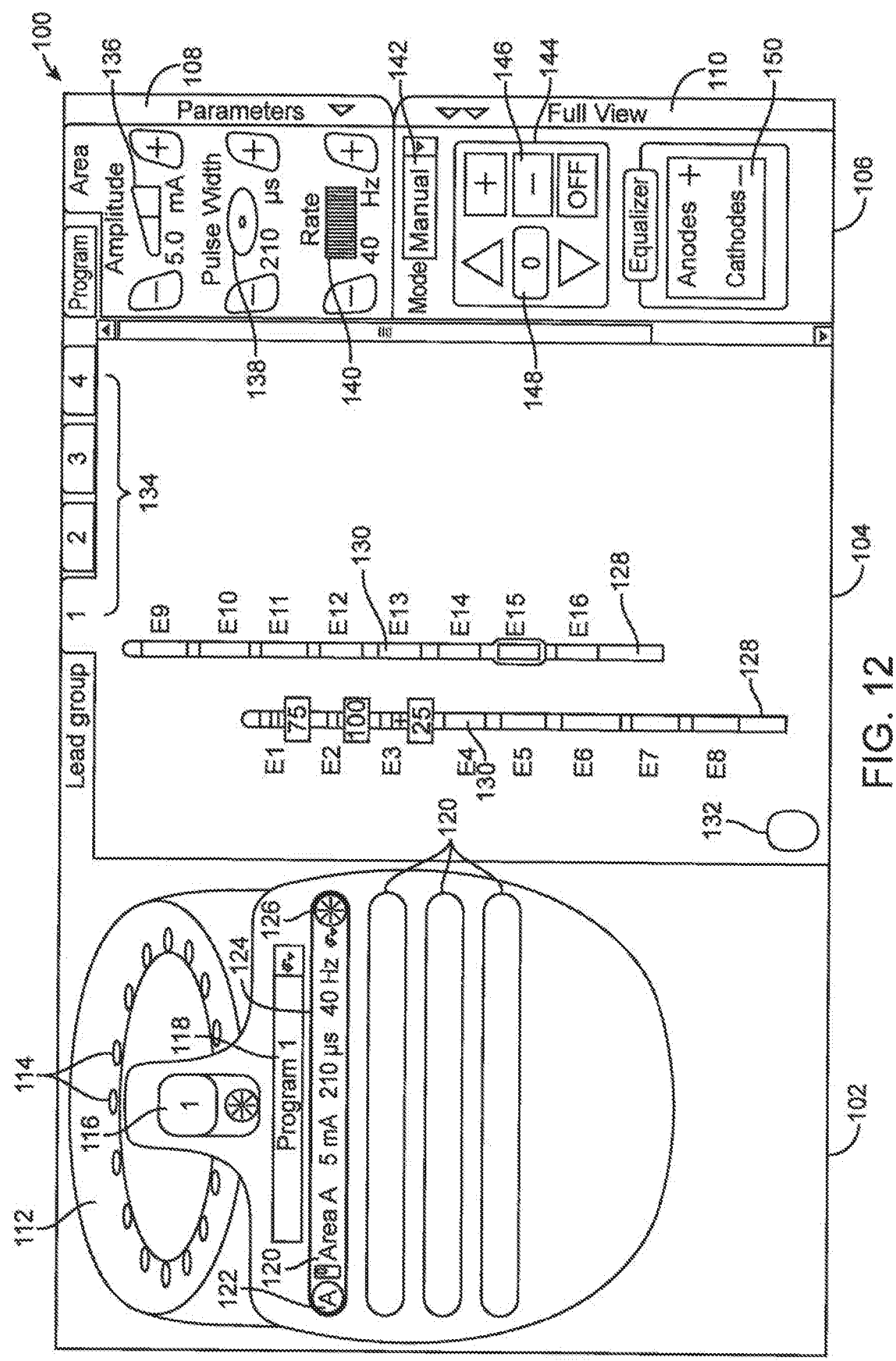
FIG. 12 is a plan view of a user interface of the CP of FIG. 11 for programming the IPG of FIG. 3 in a manual programming mode.

Referring first to FIG. 12, a graphical user interface (GUI) 100 that can be generated by the CP 18 to allow a user to program the IPG 14 will be described. In the illustrated embodiment, the GUI 100 comprises three panels: a program selection panel 102, a lead display panel 104, and a modulation parameter adjustment panel 106. Some embodiments of the GUI 100 may allow for closing and expanding one or both of the lead display panel 102 and the parameter adjustment panel 106 by clicking on the tab 108 (to show or hide the parameter adjustment panel 106) or the tab 110 (to show or hide the full view of both the lead selection panel 104 and the parameter adjustment panel 106).

The program selection panel 102 provides information about modulation programs and coverage areas that have been, or may be, defined for the IPG 14. In particular, the program selection panel 102 includes a carousel 112 on which a plurality of modulation programs 114 (in this case, up to sixteen) may be displayed and selected. The program selection panel 102 further includes a selected program status field 116 indicating the number of the modulation program 114 that is currently selected (any number from "1" to "16"). In the illustrated embodiment, program 1 is the only one currently selected, as indicated by the number "1" in the field 116. The program selection panel 102 further comprises a name field 118 in which a user may associate a unique name to the currently selected modulation program 114. In the illustrated embodiment, currently selected program 1 has been called "lower back," thereby identifying program 1 as being the modulation program 114 designed to provide therapy for lower back pain.

The program selection panel 102 further comprises a plurality of coverage areas 120 (in this case, up to four) with which a plurality of modulation parameter sets can respectively be associated to create the currently selected modulation program 114 (in this case, program 1). Each coverage area 120 that has been defined includes a designation field 122 (one of letters "A"-"D"), and an electrical pulse parameter field 124 displaying the electrical pulse parameters, and specifically, the pulse amplitude, pulse width, and pulse rate, of the modulation parameter set associated with the that coverage area. In this example, only coverage area A is defined for program 1, as indicated by the "A" in the designation field 122. The electrical pulse parameter field 124 indicates that a pulse amplitude of 5 mA, a pulse width of 210 μs, and a pulse rate of 40 Hz has been associated with coverage area A.

Each of the defined coverage areas 120 also includes a selection icon 126 that can be alternately actuated to activate or deactivate the respective coverage area 120. When a coverage area is activated, an electrical pulse train is delivered from the IPG 14 to the electrode array 26 in accordance with the modulation parameter set associated with that coverage area. Notably, multiple ones of the coverage areas 120 can be simultaneously activated by actuating the selection icons 126 for the respective coverage areas. In this case, multiple electrical pulse trains are concurrently delivered from the IPG 14 to the electrode array 26 during timing channels in an interleaved fashion in accordance with the respective modulation parameter sets associated with the coverage areas 120. Thus, each coverage area 120 corresponds to a timing channel.

To the extent that any of the coverage areas 120 have not been defined (in this case, three have not been defined), they include text "click to add another program area"), indicating that any of these remaining coverage areas 120 can be selected for association with a modulation parameter set. Once selected, the coverage area 120 will be populated with the designation field 122, electrical pulse parameter field 124, and selection icon 126.

The lead display panel 104 includes graphical leads 128, which are illustrated with eight graphical electrodes 130 each (labeled electrodes E1-E8 for the first lead 128 and electrodes E9-E16 for second lead 128). The lead display panel 104 also includes a graphical case 132 representing the case 44 of the IPG 14. The lead display panel 104 further includes lead group selection tabs 134 (in this case, four), any of which can be actuated to select one of four groups of graphical leads 128. In this case, the first lead group selection tab 134 has been actuated, thereby displaying the two graphical leads 128 in their defined orientation. In the case where additional leads 12 are implanted within the patient, they can be associated with additional lead groups.

The parameters adjustment panel 106 also includes a pulse amplitude adjustment control 136 (expressed in milliamperes (mA)), a pulse width adjustment control 138 (expressed in microseconds (μs)), and a pulse rate adjustment control 140 (expressed in Hertz (Hz)), which are displayed and actuatable in all the programming modes. Each of the controls 136-140 includes a first arrow that can be actuated to decrease the value of the respective modulation parameter and a second arrow that can be actuated to increase the value of the respective modulation parameter. Each of the controls 136-140 also includes a display area for displaying the currently selected parameter. In response to the adjustment of any of electrical pulse parameters via manipulation of the graphical controls in the parameter adjustment panel 106, the controller/processor 80 generates a corresponding modulation parameter set (with a new pulse amplitude, new pulse width, or new pulse rate) and transmits it to the IPG 14 via the telemetry circuitry 86 for use in delivering the modulation energy to the electrodes 26.

The parameter adjustment panel 106 includes a pull-down programming mode field 142 that allows the user to switch between a manual programming mode, an electronic trolling programming mode, a navigation programming mode, an exploration programming mode, and a sub-threshold programming mode. Each of these programming modes allows a user to define a modulation parameter set for the currently selected coverage area 120 of the currently selected program 114 via manipulation of graphical controls in the parameter adjustment panel 106 described above, as well as the various graphical controls described below. In the illustrated embodiment, when switching between programming modes via actuation of the programming mode field 142, the last electrode configuration with which the 14 was programmed in the previous programming mode is converted into another electrode configuration, which is used as the first electrode configuration with which the IPG 14 is programmed in the subsequent programming mode.

The electronic trolling programming mode and navigation programming mode are designed to allow a user to determine one or more efficacious modulation parameter sets for providing super-threshold therapy to the patient, whereas the exploration programming mode and sub-threshold programming mode are designed to allow the user to determine one or more efficacious modulation parameter sets for providing sub-threshold therapy to the patient. In particular, the electronic trolling programming mode is designed to quickly sweep the electrode array using a limited number of electrode configurations to gradually steer an electrical field relative to the modulation leads until the targeted modulation site is located. Using the electrode configuration determined during the electronic trolling programming mode as a starting point, the navigation programming mode is designed to use a wide number of electrode configurations to shape the electrical field, thereby fine tuning and optimization the modulation coverage for patient comfort. Both the electronic trolling mode and navigation programming mode rely on immediate feedback from the patient in response to the sensation of paresthesia relative to the region of the body in which the patient experiences pain. Like the electronic trolling programming mode, the exploration programming mode is designed to quickly sweep the electrode array using a limited number of electrode configurations to gradually steer an electrical field relative to the modulation leads until the targeted modulation site is located. Like the electronic trolling mode, the exploration programming mode relies on immediate feedback from the patient in response to the sensation of paresthesia relative to the region of the body in which the patient experiences pain. However, unlike the electronic trolling programming mode, navigation programming mode, and exploration programming mode, the sub-threshold programming mode cannot rely on immediate feedback from the patient due to the lack of paresthesia experience by the patient during sub-threshold modulation. Instead, the sub-threshold programming mode uses a transformation of the electrode configuration determined during the exploration programming mode to provide efficacious sub-threshold modulation to the determined target site of the patient.

As shown in FIG. 12, the manual programming mode has been selected. In the manual programming mode, each of the electrodes 130 of the graphical leads 128, as well as the graphical case 132, may be individually selected, allowing the clinician to set the polarity (cathode or anode) and the magnitude of the current (percentage) allocated to that electrode 130, 132 using graphical controls located in an amplitude/polarity area 144 of the parameter adjustment panel 106.

In particular, a graphical polarity control 146 located in the amplitude/polarity area 144 includes a "+" icon, a "−" icon, and an "OFF" icon, which can be respectively actuated to toggle the selected electrode 130, 132 between a positive polarization (anode), a negative polarization (cathode), and an off-state. An amplitude control 148 in the amplitude/polarity area 144 includes an arrow that can be actuated to decrease the magnitude of the fractionalized current of the selected electrode 130, 132, and an arrow that can be actuated to increase the magnitude of the fractionalized current of the selected electrode 130, 132. The amplitude control 148 also includes a display area that indicates the adjusted magnitude of the fractionalized current for the selected electrode 134. The amplitude control 148 is preferably disabled if no electrode is visible and selected in the lead display panel 104. In response to the adjustment of fractionalized electrode combination via manipulation of the graphical controls in the amplitude/polarity area 144, the controller/processor 80 generates a corresponding modulation parameter set (with a new fractionalized electrode combination) and transmits it to the IPG 14 via the telemetry circuitry 86 for use in delivering the modulation energy to the electrodes 26.

In the illustrated embodiment, electrode E2 has been selected as a cathode to which 100% of the cathodic current has been allocated, and electrodes E1 and E3 have been respectively selected as anodes to which 25% and 75% of the anodic current has been respectively allocated. Electrode E15 is shown as being selected to allow the user to subsequently allocate the polarity and fractionalized electrical current to it via the graphical controls located in the amplitude/polarity area 144. Although the graphical controls located in the amplitude/polarity area 144 can be manipulated for any of the electrodes, a dedicated graphical control for selecting the polarity and fractionalized current value can be associated with each of the electrodes, as described in U.S. Patent Publication No. 2012/0290041, entitled "Neurostimulation System with On-Effector Programmer Control," which is expressly incorporated herein by reference.

The parameters adjustment panel 106, when the manual programming mode is selected, also includes an equalization control 150 that can be actuated to automatically equalize current allocation to all electrodes of a polarity selected by respective "Anode +" and "Cathode −" icons. Unlike the other programming modes described in further detail below, the ranges of pulse rates and pulse widths of the modulation parameter sets defined during the manual programming mode are not limited to those known to result in only one of super-threshold therapy and sub-threshold therapy. For example, the lower limit of the pulse amplitude may be as low as 0.1 mA, wherein as the upper limit of the pulse amplitude may be as high as 20 mA. The lower limit of the pulse width may be as low as 2 µs, whereas the upper limit of the pulse width may be as high as 1000 µs. For example, the lower limit of the pulse rate may be as low as 1 Hz, whereas the upper limit of the pulse rate may be as high as 50 KHz. In the illustrated embodiment, a pulse amplitude of 5 mA, a pulse width of 210 µs, and a pulse rate of 40 Hz have been selected. Thus, during the manual programming mode, the selected coverage area 120 of the selected program 114 can be programmed with a modulation parameter set designed to either deliver super-threshold therapy or sub-threshold therapy to the patient.

Figure 13:
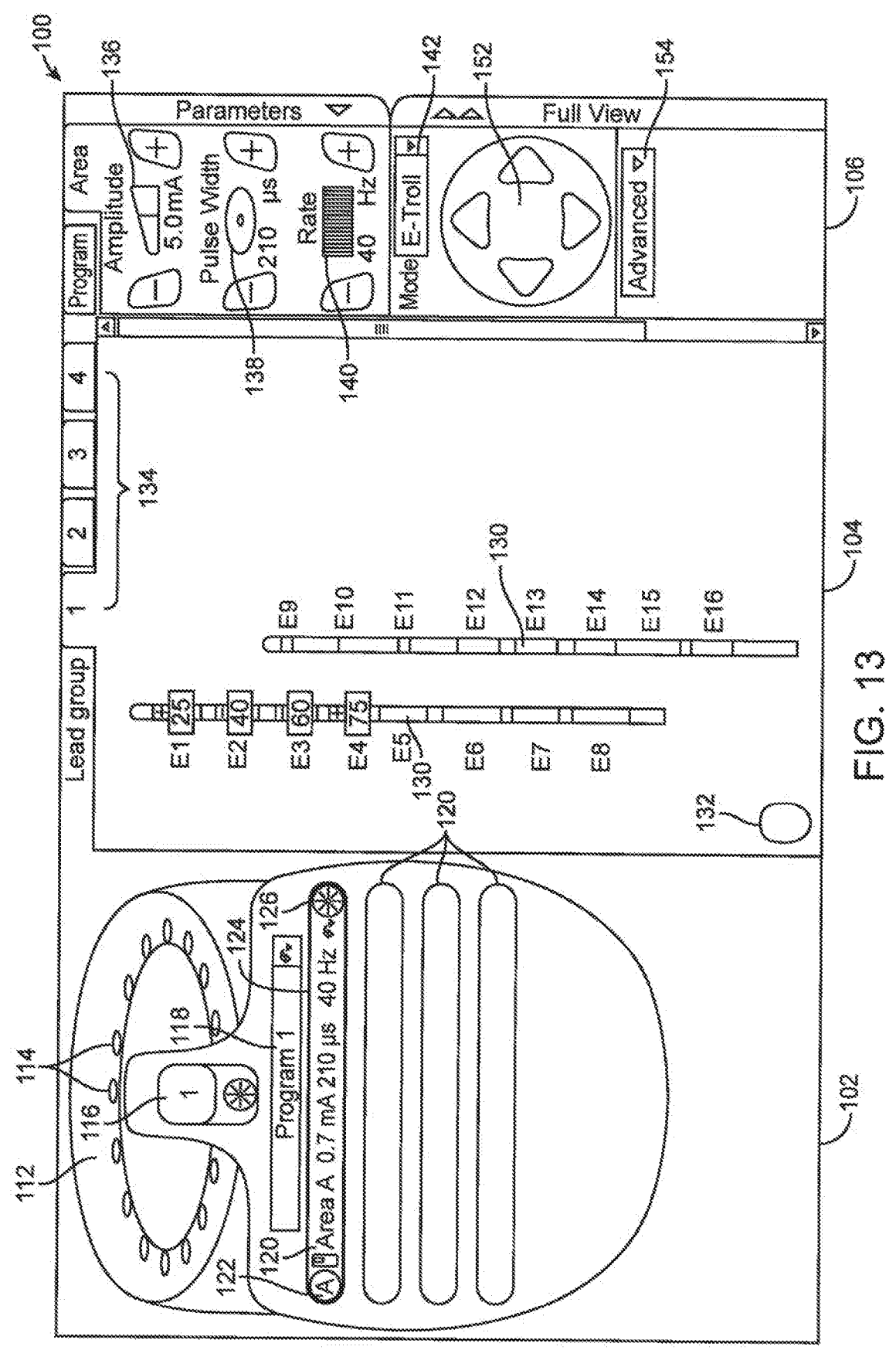

As shown in FIG. 13, the electronic trolling programming mode has been selected. In this mode, the electrodes 130 illustrated in the lead display panel 104 that were individually selectable and configurable in manual programming mode are used for display only and are not directly selectable or controllable. Instead of an amplitude/polarity area 144, the parameter selection panel 106 includes a steering array of arrows 152 that allows steering the electrical field up, down, left, or right relative to the electrodes 26. In the illustrated embodiment, the electrical current is steered by panning a virtual multipole (i.e., the virtual multipole is moved relative to the actual electrodes 26 without changing the basic configuration (focus (F) and upper anode percentage (UAP)) of the virtual multipole), and computing the electrical amplitude values needed for the actual electrodes 26 to emulate the virtual multipole. In the illustrated embodiment, fractionalized cathodic currents of 40% and 60% have been respectively computed for electrodes E2 and E3, and fractionalized anodic currents of 25% and 75% have been computed for electrodes E1 and E4. In response to the steeling of the electrical current via manipulation of the steering array of arrows 152, the controller/processor 80 generates a series of modulation parameter sets (with different fractionalized electrode combination) and transmits them to the IPG 14 via the telemetry circuitry 86 for use in delivering the modulation energy to the electrode array 26 in a manner that steers the locus of the resulting electrical field relative to the electrode array 26.

In the illustrated embodiment, the virtual multipole used in the electronic trolling programming mode is a bipole or tripole that includes a modulating cathode (i.e., cathodic modulation is providing during the electronic trolling programming mode). Furthermore, the ranges of pulse rates and pulse widths of the modulation parameter sets defined during the electronic trolling programming mode are limited to those known to result in super-threshold therapy (e.g., causing paresthesia) assuming a nominal pulse amplitude. For example, the lower limit value of the pulse width may be 100 µs, and the upper limit of the pulse rate may be 1500 Hz. In the illustrated embodiment, a pulse amplitude of 5 mA, a pulse width of 210 µs, and a pulse rate of 40 Hz have been selected.

Figure 14:
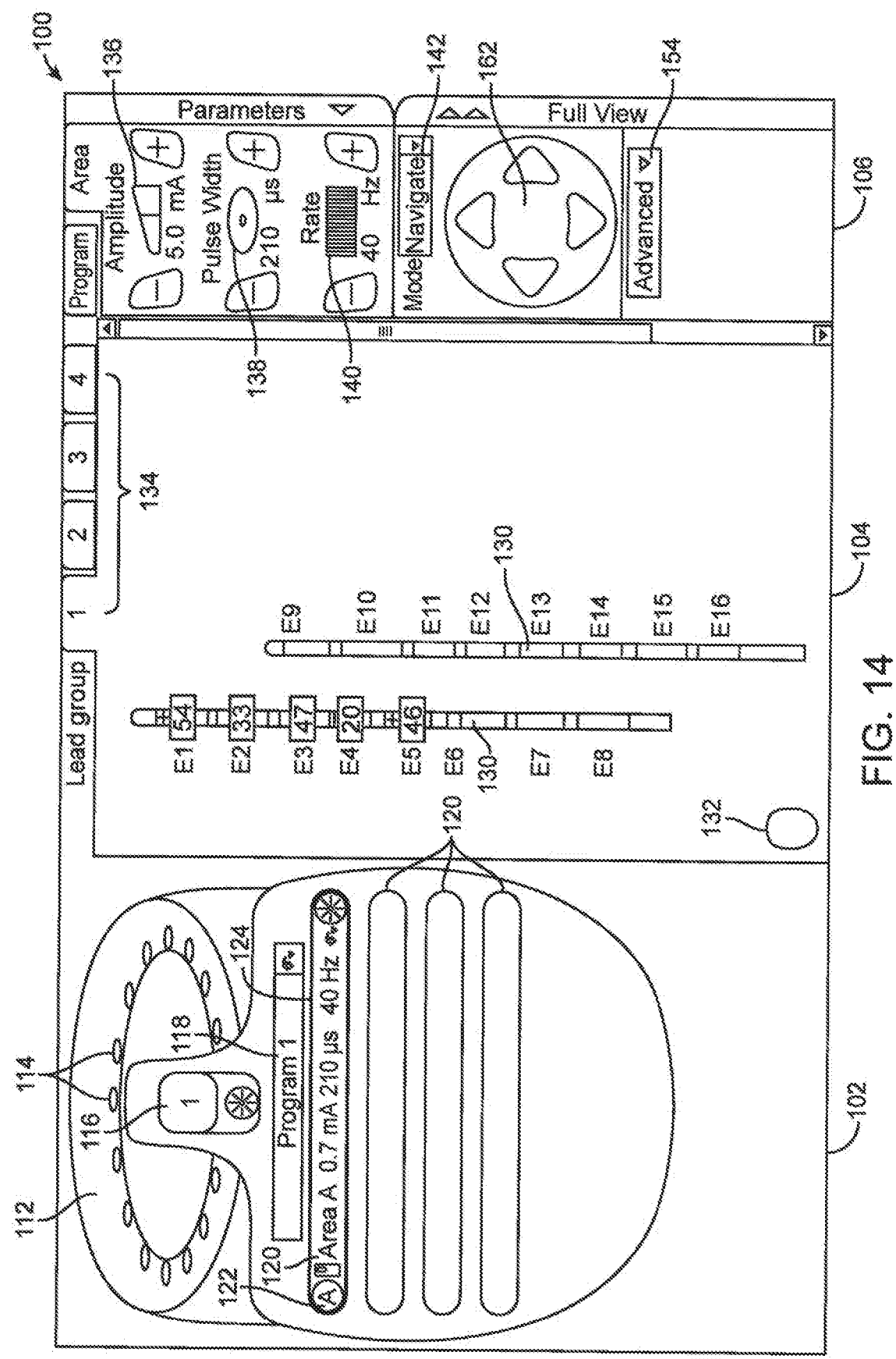
FIG. 14 is a plan view of a user interface of the CP of FIG. 11 for programming the IPG of FIG. 3 in a navigation programming mode.

As shown in FIG. 14, the navigation programming mode has been selected. As in the electronic trolling programming mode, the electrodes illustrated in the lead display panel 104 that were individually selectable and configurable in manual programming mode are used for display only and are not directly selectable or controllable in the navigation programming mode, and instead of an amplitude/polarity area 144, the parameter selection panel 106 includes a steering array of arrows 162 that allows steering the electrical field up, down, left, or right relative to the electrodes 26. In the illustrated embodiment, the electrical current is steered by weaving one or more anodes around the cathode of the virtual multipole as the cathode is displaced relative to the electrode array 26, and computing the electrical amplitude values needed for the electrodes 26 to emulate the virtual multipole. In the illustrated embodiment, fractionalized cathodic currents of 33%, 47%, and 20% have been respectively computed for electrodes E2, E3, and E4, and fractionalized anodic currents of 54% and 46% have been respectively computed for electrodes E1 and E5. In response to the steering of the electrical current via manipulation of the steering array of arrows 162, the controller/processor 80 generates a series of modulation parameter sets (with different fractionalized electrode combination) and transmits them to the IPG 14 via the telemetry circuitry 86 for use in delivering the modulation energy to the electrode array 26 in a manner that steers the locus of the resulting electrical field relative to the electrode array 26.

As with the electronic trolling programming mode, the virtual multipole used in the navigation programming mode is a bipole or tripole that includes a modulating cathode (i.e., cathodic modulation is providing during the navigation programming mode). Furthermore, the ranges of pulse rates and pulse widths of the modulation parameter sets defined during the electronic trolling programming mode are limited to those known to result in super-threshold therapy (e.g., causing paresthesia) assuming a nominal pulse amplitude. For example, the lower limit value of the pulse width may be 100 µs, and the upper limit of the pulse rate may be 1500

Hz. In the illustrated embodiment, a pulse amplitude of 5 mA, a pulse width of 210 µs, and a pulse rate of 40 Hz have been selected.

Further details discussing the use of panning a virtual multipole during the electronic trolling programming mode and weaving a virtual multipole during the navigation programming mode, as well as seamlessly switching between the manual programming mode, electronic trolling programming mode, and navigation programming mode, are described in U.S. patent application Ser. No. 13/715,751, entitled "Seamless Integration of Different Programming Modes for a Neuromodulation device Programming System," which is expressly incorporated herein by reference.

Figure 15:
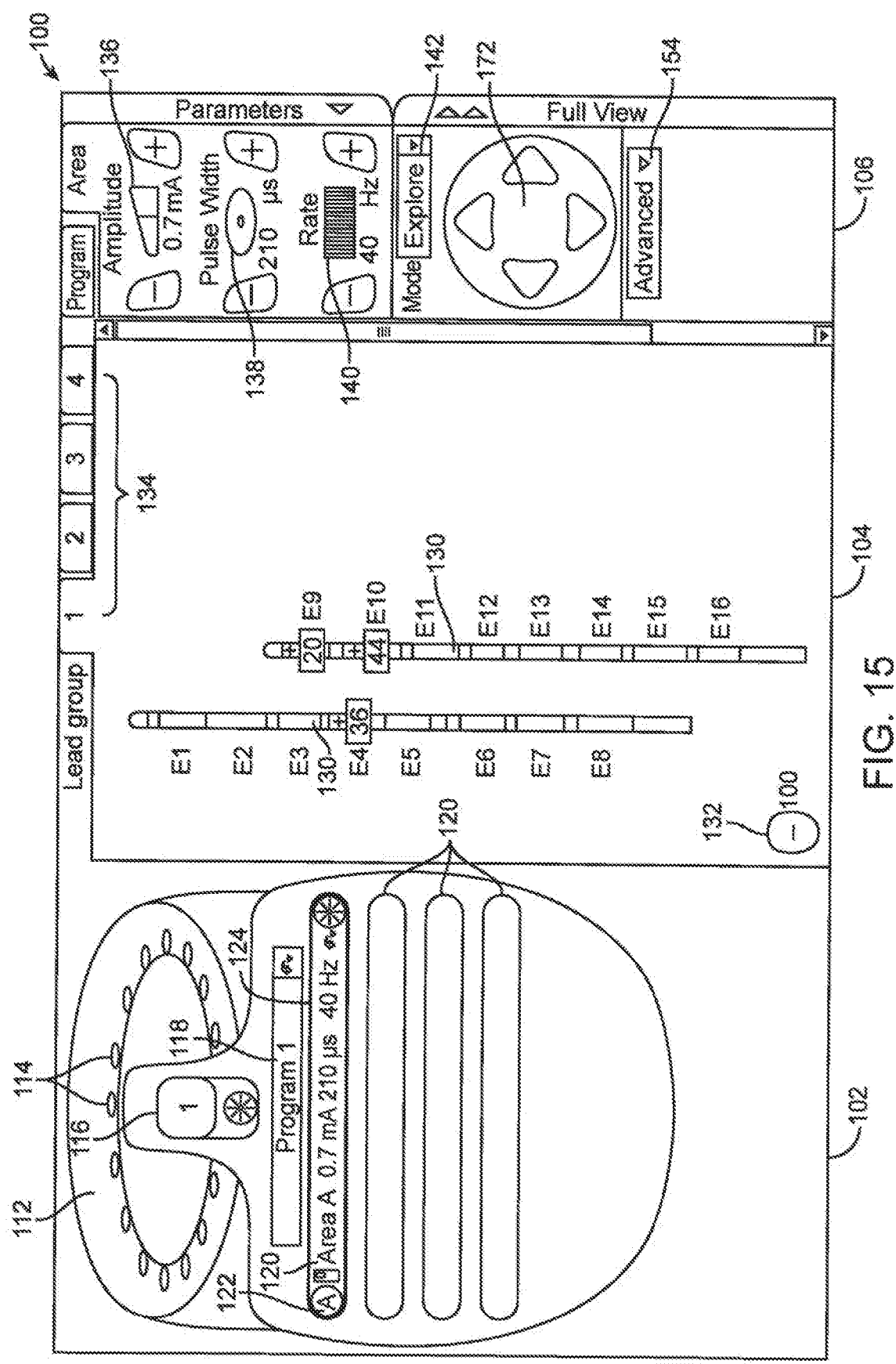
FIG. 15 is a plan view of a user interface of the CP of FIG. 11 for programming the IPG of FIG. 3 in an exploration programming mode.

As shown in FIG. 15, the exploration programming mode has been selected. As in the electronic trolling programming mode, the electrodes illustrated in the lead display panel 104 that were individually selectable and configurable in manual programming mode are used for display only and are not directly selectable or controllable in the navigation programming mode, and instead of an amplitude/polarity area 144, the parameter selection panel 106 includes a steering array of arrows 172 that allows steering the electrical field up, down, left, or right relative to the electrodes 26. In the illustrated embodiment, the electrical current is steered by panning a virtual monopole and computing the electrical amplitude values needed for the actual electrodes 26 to emulate the virtual multipole. In the illustrated embodiment, a fractionalized cathodic current of 100% has been computed for the case electrode, and fractionalized anodic currents of 36%, 20%, and 44% have been respectively computed for electrodes E4, E9, and E10. In response to the steering of the electrical current via manipulation of the steering array of arrows 172, the controller/processor 80 generates a series of modulation parameter sets (with different fractionalized electrode combinations) and transmits them to the IPG 14 via the telemetry circuitry 86 for use in delivering the modulation energy to the electrode array 26 in a manner that steers the locus of the resulting electrical field relative to the electrode array 26.

In the illustrated embodiment, the virtual monopole used in the exploration programming mode includes a primary modulating anode (i.e., anodic modulation is providing during the exploration programming mode), because it is believed that the delivery of anodic electrical current to the spinal cord tissue, and in particular the neural network of the dorsal horn (as described in U.S. patent application Ser. No. 13/843,102, filed Mar. 15, 2013, now issued as U.S. Pat. No. 9,002,459 and entitled "Method for Selectively Modulating Neural Elements in the Dorsal Horn," which is expressly incorporated herein by reference) provides sub-threshold pain relief to the patient, although it is possible that the delivery of cathodic electrical current to the spinal cord tissue may be therapeutic as well.

It should also be noted that utilization of a virtual monopole ensures that the neural tissue of interest is only targeted by anodic electrical current. In contrast, if a virtual bipole or tripole were to be utilized, one or more virtual cathodes would necessarily be located adjacent the targeted neural tissue of interest, which may confound the proper location of the virtual anode by inadvertently contributing to the paresthesia experienced by the patient. Furthermore, the electrical current delivered to the patient during the exploration programming mode is biphasic pulse waveform having a passive cathodic charge recovery phase, thereby minimizing the possibility that the cathodic charge recovery phase inadvertently contributes to the paresthesia experienced by the patient. Furthermore, like in the electronic trolling and navigation programming modes, the ranges of pulse rates and pulse widths of the modulation parameter sets defined during the exploration programming mode are limited to those known to result in super-threshold therapy (e.g., causing paresthesia) assuming a nominal pulse amplitude. For example, the lower limit value of the pulse width may be 100 µs, and the upper limit of the pulse rate may be 1500 Hz. In the illustrated embodiment, a pulse amplitude of 3.9 mA, a pulse width of 250 µs, and a pulse rate of 100 Hz have been selected.

Figure 16:
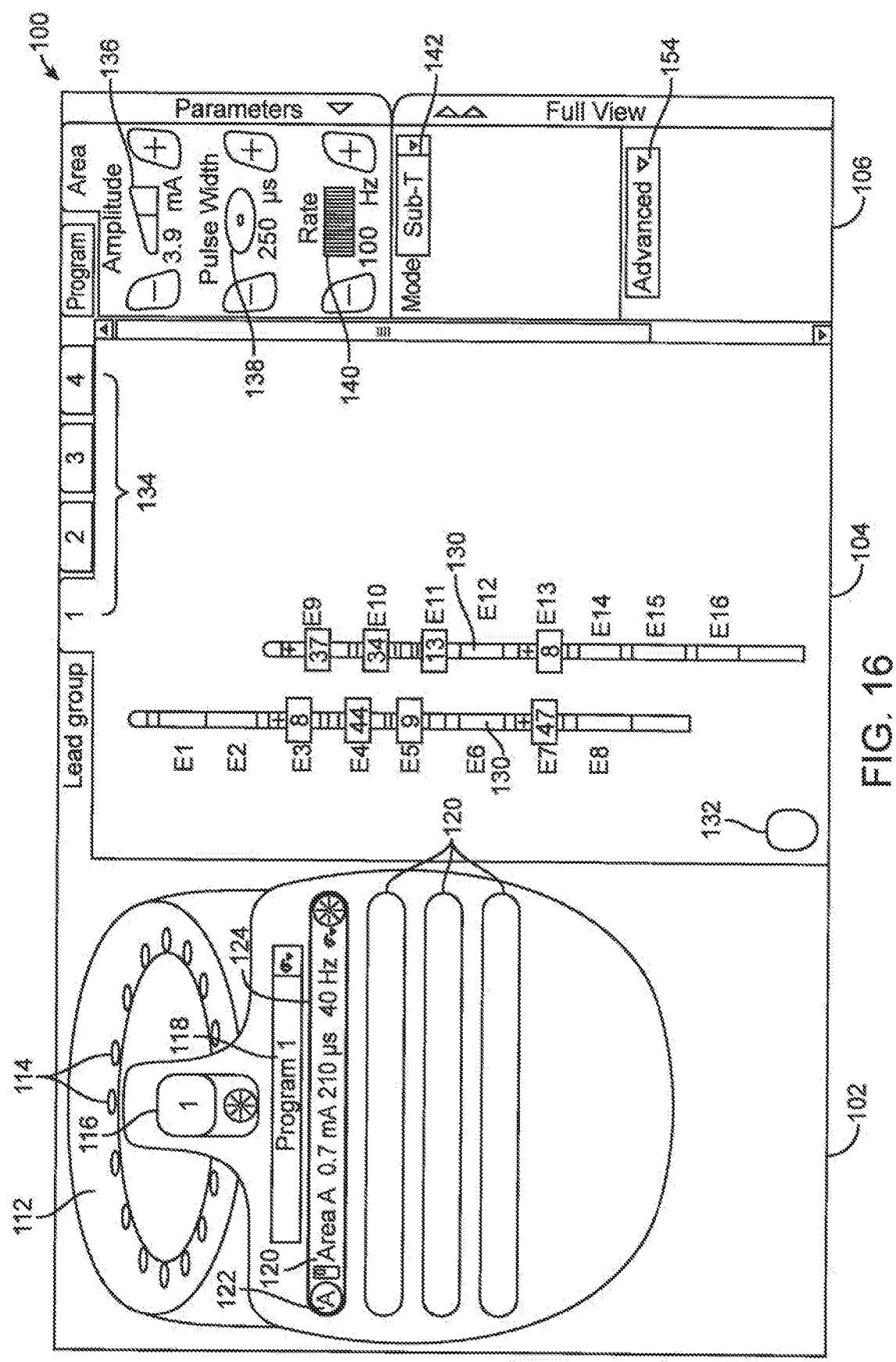
FIG. 16 is a plan view of a user interface of the CP of FIG. 11 for programming the IPG of FIG. 3 in a sub-threshold programming mode.

As shown in FIG. 16, the sub-threshold programming mode has been selected. As in the electronic trolling programming mode, the electrodes illustrated in the lead display panel 104 that were individually selectable and configurable in manual programming mode are used for display only and are not directly selectable or controllable in the navigation programming mode. The parameter selection panel 106 has neither the amplitude/polarity area 144 nor a steering array of arrows, since no paresthesia will presumably be perceived by the patient. Alternatively, the parameter selection panel 106 may have a steering array of arrows in order to adjust the locus of modulation.

In any event, the controller/processor 80 transforms the last virtual anodic monopole defined during the exploration programming mode into a virtual cathodic multipole (i.e., a virtual multiple having a primary modulating cathode). For example, the cathode of the virtual cathodic multipole can be placed at the location of the anode of the previously defined virtual anodic multiple relative to the electrode array 26, and a (focus (F) and upper anode percentage (UAP)) of the virtual cathodic multipole can be assumed (e.g., a focus of two (i.e., double the electrode spacing) and a UAP of zero (i.e., a virtual bipole)).

Although the exploration programming mode is specifically designed to find the target site for sub-threshold modulation, in an optional embodiment, the controller/processor 80 may transform the last virtual cathodic multipole defined by either of the electronic trolling programming mode or navigation programming mode into the virtual cathodic multipole. In this case, the anode of the virtual anodic multipole can be placed at the location of the cathode of the virtual cathodic multipole, and the cathode(s) of the virtual anodic multipole can be placed at the location(s) of the anode(s) of the virtual cathodic multipole relative to the electrode array 26. In another optional embodiment, the controller/processor 80 may transform the last fractionalized electrode combination defined by the manual programming mode into the virtual cathodic multipole. In this case, the controller/processor 80 may transform the manually generated fractionalized electrode combination into a virtual cathodic multipole in the manner described in U.S. patent application Ser. No. 13/715,751, which has previously been expressly incorporated herein by reference. Thus, it can be appreciated that the manual programming mode, electronic trolling programming mode, navigation programming mode, and exploration programming mode can be seamlessly switched to the sub-threshold programming mode.

In any event, the controller/processor 80 then computes amplitude values needed for the actual electrodes 26 to emulate the virtual cathodic multipole. In the illustrated embodiment, fractionalized cathodic currents of 44%, 9%, 34%, and 13% have been respectively computed for electrodes E4, E5, E12, and E13, and fractionalized anodic currents of 8%, 47%, 37%, and 8% have been respectively computed for electrodes E3, E7, E15, and E16. In the illustrated embodiment, the virtual multipole used in the sub-threshold programming mode is a biphasic pulsed waveform having an active cathodic charge recovery phase, although the biphasic pulse waveform may alternative have an active anodic charge recovery phase. In either case, the biphasic pulsed waveform will have an anodic phase that will modulate the neural tissue.

The controller/processor 80 also automatically modifies the electrical pulse parameters previously defined in the graphical controls 136-140 of the parameter adjustment panel 106 during the exploration programming mode (or alternatively, the manual programming mode, electronic trolling programming mode, or navigation programming mode) to predetermined values that ensure sub-threshold modulation. For example, in the illustrated embodiment, the pulse amplitude was reduced from 3.9 mA to 2.3 mA, the pulse width was decreased from 210 µs to 40 µs, and the pulse rate was increased from 100 Hz to 2 KHz. In general, it is preferred that the super-threshold pulse amplitude used in the exploration programming mode be reduced by 30%-70% to obtain the sub-threshold pulse amplitude in order to ensure efficacious sub-threshold therapy. Furthermore, although the sub-threshold programming mode allows the user to modify the pulse amplitude, pulse width, and pulse rate via manipulation of the graphical controls 136-140 of the parameter adjustment panel 106, the ranges of the pulse amplitudes, pulse rates, and pulse widths of the modulation parameter sets defined during the exploration programming mode are limited to those known to result in sub-threshold therapy (e.g., not causing paresthesia). For example, the upper limit value of the pulse amplitude may be 5 mA, the upper limit value of the pulse width may be 100 µs, and the lower limit of the pulse rate may be 1500 Hz.

Figure 17:
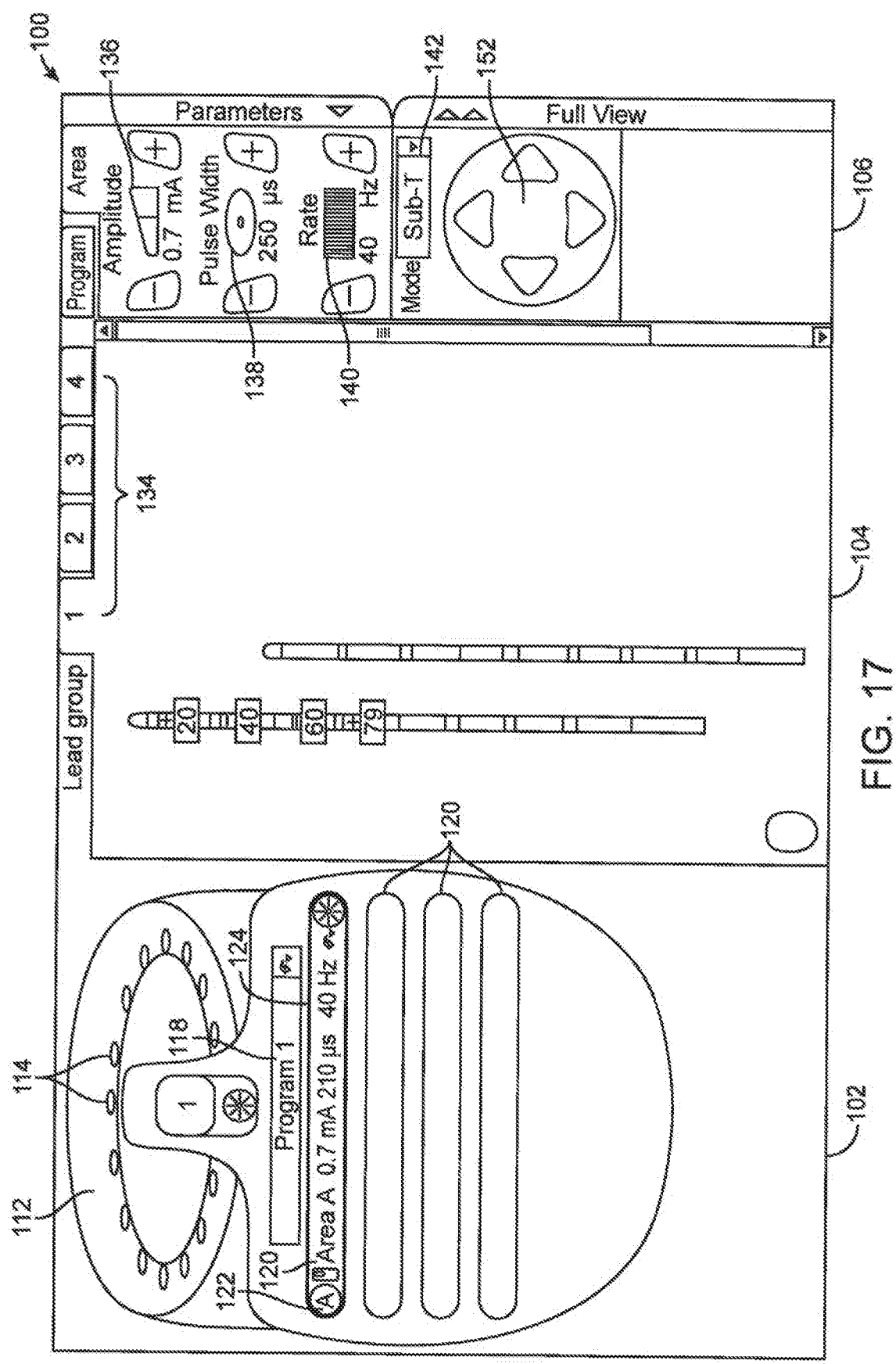
FIG. 17 is a plan view of the user interface of FIG. 13, particularly showing the expansion of the Advanced Tab into resolution and focus controls.

In any of the semi-automated modes (i.e., the electronic trolling programming mode, navigation programming mode, or exploration programming mode), the parameter adjustment panel 106 includes an advanced tab 154, as shown in FIGS. 13-16, which when actuated, hides the lead display panel 104 and provides access to a resolution control 156 and a focus control 158, as shown in FIG. 17. The resolution control 156 allows changing the modulation adjustment resolution. In one embodiment, three possible settings of mine, Medium, and Coarse may be chosen. The resolution control 156 has a "+" icon and a "−" icon that can be used to adjust the resolution. The resolution control 156 also includes a display element that graphically displays the current resolution level. When the resolution is set to Fine, each change caused by use of the steering array makes less of a change to the electrode configuration than when the resolution is set to Medium or Coarse. The focus control 158 allows changing the modulation focus by displacing the anode(s) and cathode of the virtual multipole toward each other to increase the focus, or displacing the anode(s) and cathode of the virtual multipole away from each other to decrease the focus. The focus control 158 has a "+" icon and a "−" icon that can be used to adjust the focus. The focus control 158 also includes a display element that graphically displays the current focus level. Notably, the focus control 158 is only available in the electronic trolling programming mode and navigation programming mode, since the exploration programming mode utilizes a virtual monopole that assumes an infinite distance between the anode and cathode of the virtual multipole.

Thus, it can be appreciated from the foregoing that the controller/processor 80 is capable of deriving a modulation parameter set (fractionalized electrode combination, pulse amplitude, pulse width, and/or pulse rate) for the sub-threshold programming mode from a modulation parameter set previously determined during the exploration programming mode (or alternatively, the manual programming mode, electronic programming mode, and/or navigation programming mode). The electrical field that results from the delivery of the electrical energy to the electrode array 26 in accordance with the new modulation parameter set defined for the sub-threshold programming mode will have a locus that is the same as the locus of the electrical field resulting from the conveyance of the electrical energy to the plurality of electrodes in accordance with the last modulation parameter set defined for the exploration programming mode (or alternatively, the manual programming mode, electronic programming mode, and/or navigation programming mode).

Figure 18:
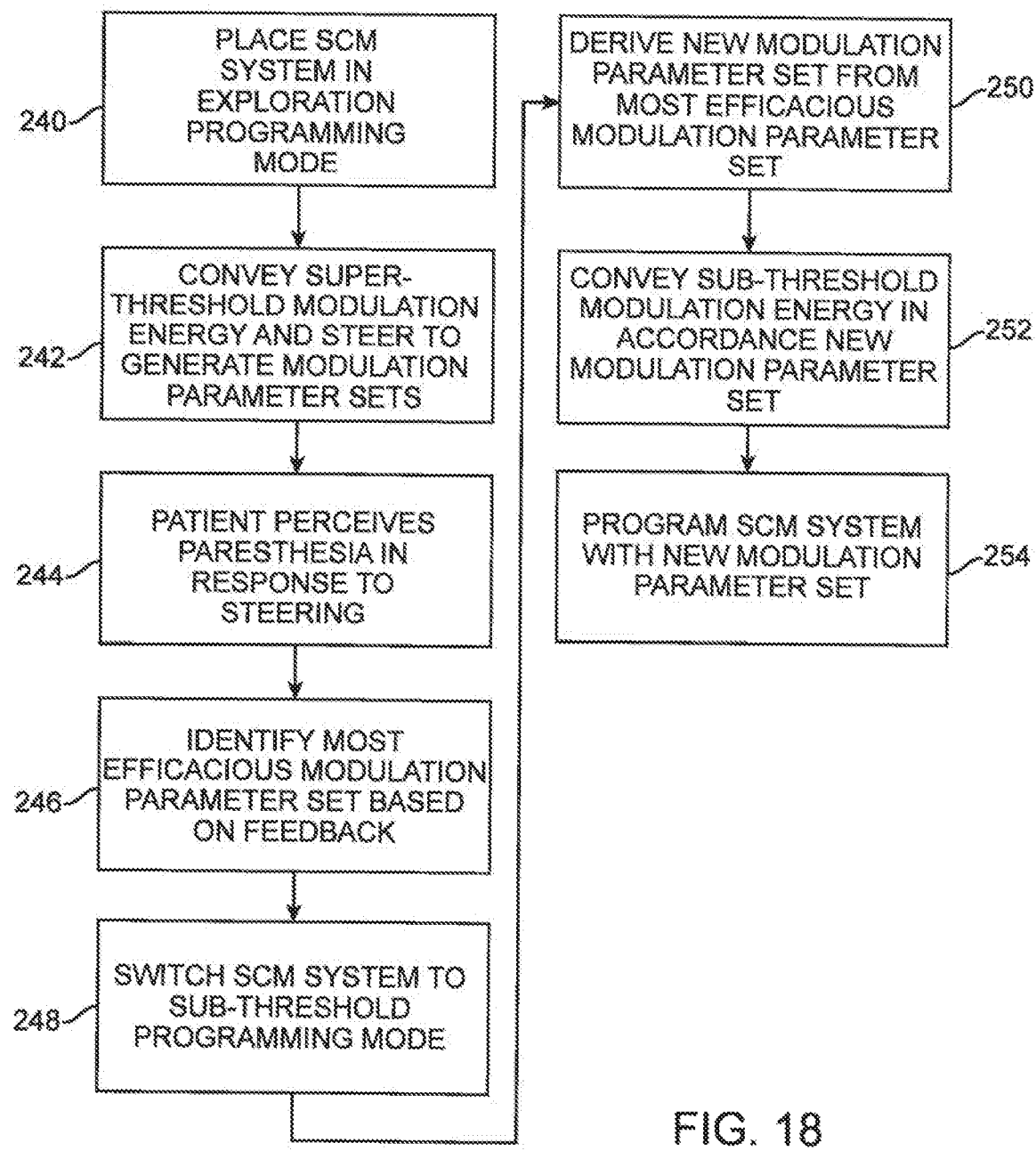
FIG. 18 is a flow diagram illustrating steps for using the CP of FIG. 11 to program the IPG of FIG. 3 to provide sub-threshold therapy to a patient to treat chronic pain.

Having described the structure and function of the CP 18, one method of using it to provide sub-threshold therapy to the patient to treat chronic pain will now be described with reference to FIG. 18. First, the SCM system 10 is placed in the exploration programming mode (step 240). Then, the SCM system 10 is operated to convey electrical modulation energy to the spinal cord tissue of the patient in accordance with a series of modulation parameter sets, such that the locus of the resulting electrical field is gradually displaced relative to the tissue (e.g., by manipulating the steering array 172 as discussed above) (step 242). Preferably, each of the modulation parameter sets defines electrical pulse parameters likely to cause the patient to perceive paresthesia. For example, each of the modulation parameter sets can define a pulse rate less than 1500 Hz and/or a pulse width greater than 100 µs. The conveyed electrical modulation energy may be monopolar in nature, and may be monophasic or biphasic (with a passive charge recovery phase), such that the polarity of the electrical energy mostly likely to provide sub-threshold therapy can be isolated, which in this case, is the anodic portion of the electrical energy. The modulation parameter sets can be created using the aforementioned virtual poles. In particular, a series of virtual poles relative to the tissue may be defined by panning a virtual pole across the electrodes, and amplitude values for electrode combinations that respectively emulate the series of virtual poles can then be computed.

The patient perceives paresthesia in response to the conveyance of the electrical modulation energy to the tissue in accordance with at least one of the modulation parameter sets (step 244). For example, if the patient experiences pain in a bodily region, such as the lower back, the electrical modulation energy conveyed in accordance with at least one of the modulation parameter sets may cause the patient to perceive paresthesia in the lower back. The modulation parameter set that results in the most efficacious therapy based on feedback from the patient may then be identified (step 246).

Next, the SCM system 10 is switched to the sub-threshold programming mode (step 248). In response, a new modulation parameter set is automatically derived from the previously identified modulation parameter set (step 250). The new modulation parameter set preferably defines electrical pulse parameters likely to cause the patient to not perceive paresthesia. For example, each of the modulation parameter sets can define a pulse rate greater than 1500 Hz and/or a pulse width less than 100 µs. The derived modulation parameter set can be created using the aforementioned virtual poles. In particular, a virtual pole relative to the tissue may be defined, and amplitude values for the electrode combination that respectively emulates the virtual poles can then be computed.

The SCM system 10 is then operated to convey electrical modulation energy to the spinal cord tissue of the patient in accordance with new modulation parameter set, thereby creating an electrical field having a locus relative to the spinal cord tissue that is the same as the locus of the electrical field associated with the identified modulation parameter set, and without causing the patient to perceive paresthesia (step 252). The conveyed electrical modulation energy preferably has an anodic component. For example, the conveyed electrical modulation energy may be bipolar in nature and be biphasic (with an active charge recovery phase). Lastly, the SCM system 10 is programmed with the new modulation parameter set (step 254).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neuromodulation system comprising: an external control device for programming an implantable neuromodulator coupled to an electrode array implanted within a patient, wherein the external control device comprises:
   a user interface configured for receiving at least one user input;
   telemetry circuitry configured for communicating with the neuromodulator; and
   controller/processor circuitry configured for responding to the at least one user input by instructing the neuromodulator to deliver super-threshold modulation, including determining a super-threshold modulation parameter set for the super-threshold modulation that is effective in treating pain, determining a sub-threshold modulation parameter set for sub-threshold modulation based on the super-threshold modulation parameter set, and instructing the neuromodulator to deliver the sub-threshold modulation to treat the pain, wherein the super-threshold modulation parameter set and the sub-threshold modulation parameter set have different pulse rates,
   wherein the determining the sub-threshold modulation parameter set includes computing a pulse amplitude value for the sub-threshold modulation parameter set as a percentage within a range of 30% to 70% of the pulse amplitude value of the super-threshold modulation parameter set.

2. The neuromodulation system of claim 1, wherein the super-threshold modulation parameter set and the sub-threshold modulation parameter set have different pulse widths.

3. The neuromodulation system of claim 1, wherein the super-threshold modulation parameter set has a pulse width value greater than 200 µs.

4. The neuromodulation system of claim 1, wherein the super-threshold modulation parameter set defines an active recharge for the super-threshold modulation.

5. The neuromodulation system of claim 1, wherein the super-threshold modulation parameter set and the sub-threshold modulation parameter set provide different electrode fractionalizations.

6. The system of claim 1, wherein the implantable neuromodulator includes a spinal cord stimulator (SCS) to deliver spinal cord stimulation.

7. A method of providing therapy to a patient using a neuromodulation system that includes an external control device and an implantable neuromodulator, comprising responding to at least one user input through a user interface of the external control device to perform a process, including:
   instructing the neuromodulator to deliver modulation energy to the patient including determining a super-threshold modulation parameter set for the super-threshold modulation that is effective in treating pain;
   determining a sub-threshold modulation parameter set for sub-threshold modulation based on the super-threshold modulation parameter set; and
   instructing the neuromodulator to deliver the sub-threshold modulation to treat the pain, wherein the super-threshold modulation parameter set and the sub-threshold modulation parameter set have different pulse rates,
   wherein the determining the sub-threshold modulation parameter set includes computing a pulse amplitude value for the sub-threshold modulation parameter set as a percentage within a range of 30% to 70% of the pulse amplitude value of the super-threshold modulation parameter set.

8. The method of claim 7, wherein the super-threshold modulation parameter set defines an active recharge.

9. The method of claim 7, wherein the super-threshold modulation parameter set and the sub-threshold modulation parameter set provide different electrode fractionalizations.

10. The method of claim 7, wherein the super-threshold modulation parameter set and the sub-threshold modulation parameter set have different pulse widths.

11. The method of claim 7, wherein the super-threshold modulation parameter set has a pulse width value greater than 200 µs.

12. The method of claim 7, wherein the implantable neuromodulator includes a spinal cord stimulator (SCS) to deliver spinal cord stimulation.

13. A non-transitory machine-readable medium including instructions, which when executed by a machine, cause the machine to perform a process, comprising responding to at least one user input through a user interface to perform a process, including:
   instructing a neuromodulator to deliver modulation energy to the patient including determining a super-threshold modulation parameter set for the super-threshold modulation that is effective in treating pain;
   determining a sub-threshold modulation parameter set for sub-threshold modulation based on the super-threshold modulation parameter set, wherein the super-threshold modulation parameter set and the sub-threshold modulation parameter set have different pulse rates; and
   instructing the neuromodulator to deliver the sub-threshold modulation to treat the pain,
   wherein the determining the sub-threshold modulation parameter set includes computing a pulse amplitude value for the sub-threshold modulation parameter set as a percentage within a range of 30% to 70% of the pulse amplitude value of the super-threshold modulation parameter set.

14. The non-transitory machine-readable medium of claim 13, wherein the super-threshold modulation parameter set defines an active recharge.

15. The non-transitory machine-readable medium of claim 13, wherein the super-threshold modulation parameter set and the sub-threshold modulation parameter set provide different electrode fractionalizations.

16. The non-transitory machine-readable medium of claim 13, wherein the super-threshold modulation parameter set and the sub-threshold modulation parameter set have different pulse widths.

17. The non-transitory machine-readable medium of claim 13, wherein the super-threshold modulation parameter set has a pulse width value greater than 200 µs.

18. The non-transitory machine-readable medium of claim 13, wherein the implantable neuromodulator includes a spinal cord stimulator (SCS) to deliver spinal cord stimulation.

* * * * *